US008193230B2

(12) United States Patent
Wallace et al.

(10) Patent No.: US 8,193,230 B2
(45) Date of Patent: *Jun. 5, 2012

(54) COMPOSITIONS COMPRISING N3 ALKYLATED BENZIMIDAZOLE DERIVATIVES AS MEK INHIBITORS AND METHODS OF USE THEREOF

(75) Inventors: Eli M. Wallace, Boulder, CO (US); Joseph P. Lyssikatos, Piedmont, CA (US); Allison L. Marlow, Boulder, CO (US); T. Brian Hurley, Boulder, CO (US)

(73) Assignee: Array Biopharma Inc., Boulder, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/824,547

(22) Filed: Jun. 28, 2010

(65) Prior Publication Data

US 2010/0260714 A1    Oct. 14, 2010

Related U.S. Application Data

(63) Continuation of application No. 12/050,827, filed on Mar. 18, 2008, now Pat. No. 7,777,050, which is a continuation of application No. 11/061,336, filed on Feb. 18, 2005, now Pat. No. 7,425,637, which is a continuation of application No. 10/387,879, filed on Mar. 13, 2003, now abandoned.

(60) Provisional application No. 60/364,007, filed on Mar. 13, 2002.

(51) Int. Cl.
A61K 31/4184 (2006.01)

(52) U.S. Cl. ........................................................ 514/394

(58) Field of Classification Search .................... 514/394
See application file for complete search history.

(56) References Cited

U.S. PATENT DOCUMENTS

| | | | |
|---|---|---|---|
| 5,128,356 A | 7/1992 | Naka et al. |
| 5,216,003 A | 6/1993 | Vasquez et al. |
| 5,250,554 A | 10/1993 | Naka et al. |
| 5,525,625 A | 6/1996 | Bridges et al. |
| 5,750,545 A | 5/1998 | Akahoshi et al. |
| 5,972,980 A | 10/1999 | Cornicelli et al. |
| 6,255,494 B1 | 7/2001 | Britton et al. |
| 6,310,060 B1 | 10/2001 | Barrett et al. |
| 6,440,966 B1 | 8/2002 | Barrett et al. |
| 6,455,582 B1 | 9/2002 | Tecle |
| 6,469,004 B1 | 10/2002 | Barrett et al. |
| 6,506,798 B1 | 1/2003 | Barrett et al. |
| 6,534,503 B1 | 3/2003 | Dines et al. |
| 6,545,030 B1 | 4/2003 | Barrett et al. |
| 6,696,440 B1 | 2/2004 | Bridges et al. |
| 6,740,649 B2 | 5/2004 | Ott et al. |
| 6,803,362 B2 | 10/2004 | Carruthers et al. |
| 6,821,963 B2 | 11/2004 | Barrett et al. |
| 6,891,066 B2 | 5/2005 | Rewcastle et al. |
| 6,960,614 B2 | 11/2005 | Barrett et al. |
| 7,001,905 B2 | 2/2006 | Biwersi et al. |
| 7,030,119 B1 | 4/2006 | Barrett et al. |
| 7,067,532 B2 | 6/2006 | Boyle et al. |
| 7,102,009 B2 | 9/2006 | Patel et al. |
| 7,160,915 B2 | 1/2007 | Barrett et al. |
| 7,235,537 B2 | 6/2007 | Wallace et al. |
| 2003/0078428 A1 | 4/2003 | Barrett et al. |
| 2003/0092748 A1 | 5/2003 | Barrett et al. |
| 2003/0224500 A1 | 12/2003 | Ohren et al. |
| 2004/0039208 A1 | 2/2004 | Chen et al. |
| 2004/0058934 A1 | 3/2004 | Carruthers et al. |
| 2004/0127395 A1 | 7/2004 | Desai et al. |
| 2004/0186111 A1 | 9/2004 | Sun et al. |
| 2005/0272740 A1 | 12/2005 | Dorsch et al. |
| 2007/0004713 A1 | 1/2007 | Barlaam et al. |

FOREIGN PATENT DOCUMENTS

| | | |
|---|---|---|
| EP | 0639573 A1 | 2/1995 |
| EP | 0694535 A1 | 1/1996 |
| EP | 1321518 A1 | 6/2003 |
| JP | 2000204077 | 7/2000 |
| WO | 9503286 A1 | 2/1995 |
| WO | 9843960 A1 | 10/1998 |
| WO | 9901421 A1 | 1/1999 |
| WO | 9901426 A1 | 1/1999 |
| WO | 0040235 A2 | 7/2000 |
| WO | 0040235 A3 | 7/2000 |
| WO | 0040237 A1 | 7/2000 |
| WO | 0041505 A2 | 7/2000 |
| WO | 0041994 A1 | 7/2000 |
| WO | 0042002 A1 | 7/2000 |
| WO | 0042003 A1 | 7/2000 |
| WO | 0042022 A1 | 7/2000 |
| WO | 0042029 A1 | 7/2000 |
| WO | 0068201 A1 | 11/2000 |
| WO | 0105390 A2 | 1/2001 |
| WO | 0105391 A2 | 1/2001 |

(Continued)

OTHER PUBLICATIONS

Golub et al., Science, vol. 286, Oct. 15, 1999, pp. 531-537.*

Brognard, et al., "Variable apoptotic response of NSCLC cells to inhibition of the MEK/ERK pathway by small molecules or dominant negative mutants", Cell Death and Differentiation (2002), 893-904, vol. 9.

Katsanakis, et al., "The Progression in the Mouse Skin Carcinogenesis Model Correlates with ERK1/2 Signaling", Molecular Medicine, (2002) 624-637, 8(10).

Murphy, et al., "Pancreatic cancer cells require an EGF receptor-mediated autocrine pathway for proliferation in serum-free conditions", British Journal of Cancer (2001), 926-935, 84(7).

(Continued)

Primary Examiner — Laura L. Stockton
(74) Attorney, Agent, or Firm — John R. Moore, Esq.; Sarah S. Mastous; Viksins Harris & Padys PLLP

(57) ABSTRACT

Disclosed are pharmaceutical compositions comprising 6-(4-bromo-2-fluorophenylamino)-7-fluoro-3-methyl-3H-benzoimidazole-5-carboxylic acid (2-hydroxy-ethoxy)-amide, or a pharmaceutically acceptable salt thereof. Also disclosed are methods of using such compositions for inhibiting abnormal cell growth or treating hyperproliferative diseases in mammals.

4 Claims, No Drawings

FOREIGN PATENT DOCUMENTS

| WO | 0105392 A2 | 1/2001 |
|---|---|---|
| WO | 0105393 A2 | 1/2001 |
| WO | 0121634 A1 | 3/2001 |
| WO | 0168619 A1 | 9/2001 |
| WO | 0206213 A2 | 1/2002 |
| WO | 0218319 A1 | 3/2002 |
| WO | 0244166 A1 | 6/2002 |
| WO | 03054180 A1 | 7/2003 |
| WO | 03062191 A1 | 7/2003 |
| WO | 2005009975 A2 | 2/2005 |

OTHER PUBLICATIONS

Boucher, et al., "MEK/ERK Signaling Pathway Regulates the Expression of Bcl-2, Bcl-XL, and Mcl-1 and Promotes Survival of Human Pancreatic Cancer Cells", Journal of Cellular Biochemistry, (2000), 355-369, 79.

Fukazawa, et al., "Mitogen-activated Protein/Extracellular Signal-regulated Kinase Kinase (MEK) Inhibitors Restore Anoikis Sensitivity in Human Breast Cancer Cell Lines with a Constitutively Activated Extracellular-regulated Kinase (ERK) Pathway", Molecular Cancer Therapeutics, (2002), 303-309, vol. 1.

Hermanto, et al., "Inhibition of Mitogen-activated Protein Kinase Kinase Selectively Inhibits Cell Proliferation in Human Breast Cancer Cells Displaying Enhanced Insulin-like Growth Factor I-mediated Mitogen-activated Protein Kinase Activation", Cell Growth & Differentiation, (2000), 655-664, vol. 11, December.

Hu, et al., "Cytotoxicity induced by manipulation of signal transduction pathway is associated with down-regulation of Bcl-2 but not Mcl-1 in MCF-7 human breast cancer", Breast Cancer Research and Treatment, (2001), 11-20, 70.

Simon, "PD 098059, an inhibitor of ERK1 activation, attenuates the in vivo invasiveness of head and neck squamous cell carcinoma", British Journal of Cancer (1999), 1412-1419, 80(9).

Sebolt-Leopold, et al., "Blockade of the MAP kinase pathway suppresses growth of colon tumors in vivo", Nature Medicine (1999), 810-816, 5(7).

Ge, et al., "U0126, a mitogen-activated protein kinase kinase inhibitor, inhibits the invasion of human A375 melanoma cells", Cancer Letters (2002), 133-140, vol. 179.

Kang, et al., "Role of Ras/ERK-dependent pathway in the erythroid differentiaction of K562 cells", Experimental and Molecular Medicine (1999), 76-82, vol. 31.

Milella, et al., "Therapeutic targeting of the MEK/MAPK signal transduction module in acute myeloid leukemia", The Journal of Clinical Investigation, (2001), 851-859, 108(6).

Qiao, et al., "Pharmacologic Inhibitors of the Mitogen Acativated Protein Kinase Cascade Have the Potential to Interact with Ionizing Radiation Exposure to Induce Cell Death in Carcinoma Cells by Multiple Mechanisms", Cancer Biology & Therapy, (2002), 168-176, 1(2).

Mackeigan, et al., "Inactivation of the Antiapoptotic Phosphatidylinositol 3-Kinase-Akt Pathway by the Combined Treatment of Taxol and Mitogen-activated Protein Kinase Kinase Inhibition", Clinical Cancer Research (2002), 2091-2099, vol. 8.

Dry, et al., "Transcriptional Pathway Signatures Predict MEK Addiction and Response to Selumetinib (AZD6244)", Molecular and Cellular Pathobiology, (2010), 2264-2273, 70(6).

Little, et al., "Amplification of the Driving Oncogene, KRAS or BRAF, Underpins Acquired Resistance to MEK1/2 Inhibitors in Colorectal Cancer Cells", Sci Signal, (2011), Mar. 29;4(166):ra17.

Gopal, et al., "Basal and Treatment-Induced Activation of AKT mediates Resistance to Cell Death by AZD6244 (ARRY-142886) in Braf-Mutant Human Cutaneous melanoma Cells", Cancer Research, (2010), 8736-8747, 70(21).

\* cited by examiner

COMPOSITIONS COMPRISING N3 ALKYLATED BENZIMIDAZOLE DERIVATIVES AS MEK INHIBITORS AND METHODS OF USE THEREOF

CROSS-REFERENCE TO RELATED APPLICATION

This application is a Continuation of U.S. application Ser. No. 12/050,827, filed Mar. 18, 2008, now issued as U.S. Pat. No. 7,777,050, which is a Continuation of U.S. application Ser. No. 11/061,336, filed Feb. 18, 2005, now U.S. Pat. No. 7,425,637, which is a Continuation of U.S. application Ser. No. 10/387,879, filed Mar. 13, 2003, now abandoned, which claims priority to U.S. Application No. 60/364,007, filed Mar. 13, 2002, each of which is incorporated herein by reference in its entirety.

BACKGROUND OF THE INVENTION

1. Field of the Invention

This invention relates to a series of alkylated (1H-Benzoimidazol-5-yl)-(4-substituted-phenyl)-amine derivatives that are useful in the treatment of hyperproliferative diseases, such as cancer and inflammation, in mammals. This invention also relates to a method of using such compounds in the treatment of hyperproliferative diseases in mammals, especially humans, and to pharmaceutical compositions containing such compounds.

2. Summary of the Related Art

Cell signaling through growth factor receptors and protein kinases is an important regulator of cell growth, proliferation and differentiation. In normal cell growth, growth factors, through receptor activation (i.e., PDGF or EGF and others), activate MAP kinase pathways. One of the most important and most well understood MAP kinase pathways involved in normal and uncontrolled cell growth is the Ras/Raf kinase pathway. Active GTP-bound Ras results in the activation and indirect phosphorylation of Raf kinase. Raf then phosphorylates MEK1 and 2 on two serine residues (S218 and S222 for MEK1 and S222 and S226 for MEK2) (Ahn, et al., *Methods in Enzymology* 2001, 332, 417-431). Activated MEK then phosphorylates its only known substrates, the MAP kinases, ERK1 and 2. ERK phosphorylation by MEK occurs on Y204 and T202 for ERK1 and Y185 and T183 for ERK2 (Ahn, et al., 2001, supra). Phosphorylated ERK dimerizes and then translocates to the nucleus where it accumulates (Khokhlatchev et al., *Cell* 1998, 93, 605-615). In the nucleus, ERK is involved in several important cellular functions, including but not limited to nuclear transport, signal transduction, DNA repair, nucleosome assembly and translocation, and mRNA processing and translation (Ahn, et al., *Molecular Cell* 2000, 6, 1343-1354). Overall, treatment of cells with growth factors leads to the activation of ERK1 and 2 which results in proliferation and, in some cases, differentiation (Lewis et al., *Adv. Cancer Res.* 1998, 74, 49-139).

In proliferative diseases, genetic mutations and/or overexpression of the growth factor receptors, downstream signaling proteins, or protein kinases involved in the ERK kinase pathway lead to uncontrolled cell proliferation and, eventually, tumor formation. For example, some cancers contain mutations which result in the continuous activation of this pathway due to continuous production of growth factors. Other mutations can lead to defects in the deactivation of the activated GTP-bound Ras complex, again resulting in activation of the MAP kinase pathway. Mutated, oncogenic forms of Ras are found in 50% of colon and >90% pancreatic cancers as well as many others types of cancers (Kohl, et al., *Science* 1993, 260, 1834-1837). Recently, bRaf mutations have been identified in more than 60% of malignant melanoma (Davies, H. et al., *Nature* 2002, 417, 949-954). These mutations in bRaf result in a constitutively active MAP kinase cascade. Studies of primary tumor samples and cell lines have also shown constitutive or overactivation of the MAP kinase pathway in cancers of pancreas, colon, lung, ovary and kidney (Hoshino, R. et al., *Oncogene* 1999, 18, 813-822). Hence, there is a strong correlation between cancers and an overactive MAP kinase pathway resulting from genetic mutations.

As constitutive or overactivation of MAP kinase cascade plays a pivotal role in cell proliferation and differentiation, inhibition of this pathway is believed to be beneficial in hyperproliferative diseases. MEK is a key player in this pathway as it is downstream of Ras and Raf. Additionally, it is an attractive therapeutic target because the only known substrates for MEK phosphorylation are the MAP kinases, ERK1 and 2. Inhibition of MEK has been shown to have potential therapeutic benefit in several studies. For example, small molecule MEK inhibitors have been shown to inhibit human tumor growth in nude mouse xenografts, (Sebolt-Leopold, et al., *Nature-Medicine* 1999, 5 (7), 810-816; Trachet, et al., AACR Apr. 6-10, 2002, Poster #5426; Tecle, H. IBC 2$^{nd}$ International Conference of Protein Kinases, Sep. 9-10, 2002), block static allodynia in animals (WO 01/05390 published Jan. 25, 2001) and inhibit growth of acute myeloid leukemia cells (Milella, et al., *J. Clin. Invest.*, 2001, 108 (6), 851-859).

Small molecule inhibitors of MEK have been disclosed. At least thirteen patent applications have appeared in the last several years: U.S. Pat. No. 5,525,625 filed Jan. 24, 1995; WO 98/43960 published Oct. 8, 1998; WO 99/01421 published Jan. 14, 1999; WO 99/01426 published Jan. 14, 1999; WO 00/41505 published Jul. 20, 2000; WO 00/42002 published Jul. 20, 2000; WO 00/42003 published Jul. 20, 2000; WO 00/41994 published Jul. 20, 2000; WO 00/42022 published Jul. 20, 2000; WO 00/42029 published Jul. 20, 2000; WO 00/68201 published Nov. 16, 2000; WO 01/68619 published Sep. 20, 2001; and WO 02/06213 published Jan. 24, 2002.

SUMMARY OF THE INVENTION

This invention provides for alkylated (1H-benzoimidazol-5-yl)-(4-substituted phenyl)-amine compounds of Formula I, and pharmaceutically acceptable salts and prodrugs thereof that are useful in the treatment of hyperproliferative diseases. Specifically, the present invention relates to compounds of Formula I that act as MEK inhibitors. Also provided is a method for treatment of cancer. Also provided are formulations containing compounds of Formula I and methods of using the compounds to treat a patient in need thereof. In addition, there are described processes for preparing the inhibitory compounds of Formula I.

Accordingly, the present invention provides compounds of the Formula I:

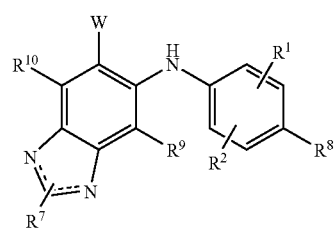

I and pharmaceutically accepted salts, prodrugs and solvates thereof, wherein:

------ is an optional bond, provided that one and only one nitrogen of the ring is double-bonded;

$R^1$, $R^2$, $R^9$ and $R^{10}$ are independently selected from hydrogen, halogen, cyano, nitro, trifluoromethyl, difluoromethoxy, trifluoromethoxy, azido, —$OR^3$, —$C(O)R^3$, —$C(O)OR^3$, $NR^4C(O)OR^6$, —$OC(O)R^3$, —$NR^4SO_2R^6$, —$SO_2NR^3R^4$, —$NR^4C(O)R^3$, —$C(O)NR^3R^4$, —$NR^5C(O)NR^3R^4$, —$NR^5C(NCN)NR^3R^4$, —$NR^3R^4$, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, —$S(O)_j(C_1$-$C_6$ alkyl), —$S(O)_j(CR^4R^5)_m$-aryl, aryl, arylalkyl, heteroaryl, heteroarylalkyl, heterocyclyl, heterocyclylalkyl, —$O(CR^4R^5)_m$-aryl, —$NR^4(CR^4R^5)_m$-aryl, —$O(CR^4R^5)_m$-heteroaryl, —$NR^4(CR^4R^5)_m$-heteroaryl, —$O(CR^4R^5)_m$-heterocyclyl and —$NR^4(CR^4R^5)_m$-heterocyclyl, where each alkyl, alkenyl, alkynyl, cycloalkyl, aryl, heteroaryl and heterocyclyl portion is optionally substituted with one to five groups independently selected from oxo, halogen, cyano, nitro, trifluoromethyl, difluoromethoxy, trifluoromethoxy, azido, —$NR^4SO_2R^6$, —$SO_2NR^3R^4$, —$C(O)R^3$, —$C(O)OR^3$, —$OC(O)R^3$, —$NR^4C(O)OR^6$, —$NR^4C(O)R^3$, —$C(O)NR^3R^4$, —$NR^3R^4$, —$NR^5C(O)NR^3R^4$, —$NR^5C(NCN)NR^3R^4$, —$OR^3$, aryl, heteroaryl, arylalkyl, heteroarylalkyl, heterocyclyl, and heterocyclylalkyl;

$R^3$ is selected from hydrogen, trifluoromethyl, $C_1$-$C_{10}$ alkyl, $C_2$-$C_{10}$ alkenyl, $C_2$-$C_{10}$ alkynyl, $(CH_2)_n$ $C_3$-$C_{10}$ cycloalkyl, $C_3$-$C_{10}$ cycloalkylalkyl, aryl, arylalkyl, heteroaryl, heteroarylalkyl, heterocyclyl, and heterocyclylalkyl, where each alkyl, alkenyl, alkynyl, cycloalkyl, aryl, heteroaryl and heterocyclyl portion is optionally substituted with one to five groups independently selected from oxo, halogen, cyano, nitro, trifluoromethyl, difluoromethoxy, trifluoromethoxy, azido, —NR'SO$_2$R'''', —SO$_2$NR'R'', —C(O)R', —C(O)OR', —OC(O)R', —NR'C(O)OR'''', —NR'C(O)R'', —C(O)NR'R'', —SR', —S(O)R'''', —SO$_2$R'''', —NR'R'', —NR'C(O)NR''R''', —NR'C(NCN)NR''R''', —OR', aryl, heteroaryl, arylalkyl, heteroarylalkyl, heterocyclyl, and heterocyclylalkyl;

R', R'' and R''' independently are selected from hydrogen, lower alkyl, lower alkenyl, aryl and arylalkyl;

R'''' is selected from lower alkyl, lower alkenyl, aryl and arylalkyl; or any two or R', R'', R''' or R'''' can be taken together with the atom to which they are attached to form a 4 to 10 membered carbocyclic, heteroaryl or heterocyclic ring, each of which is optionally substituted with one to three groups independently selected from halogen, cyano, nitro, trifluoromethyl, difluoromethoxy, trifluoromethoxy, azido, aryl, heteroaryl, arylalkyl, heteroarylalkyl, heterocyclyl, and heterocyclyalkyl; or $R^3$ and $R^4$ can be taken together with the atom to which they are attached to form a 4 to 10 membered carbocyclic, heteroaryl or heterocyclic ring, each of which is optionally substituted with one to three groups independently selected from halogen, cyano, nitro, trifluoromethyl, difluoromethoxy, trifluoromethoxy, azido, —NR'SO$_2$R'''', —SO$_2$NR'R'' —C(O)R', —C(O)OR', —OC(O)R', —NR'C(O)OR'''', —NR'C(O)R'', —C(O)NR'R'', —SO$_2$R'''', —NR'R'', —NR'C(O)NR''R''', —NR'C(NCN)NR''R''', —OR', aryl, heteroaryl, arylalkyl, heteroarylalkyl, heterocyclyl, and heterocyclylalkyl; or $R^4$ and $R^5$ independently represent hydrogen or $C_1$-$C_6$ alkyl, or $R^4$ and $R^5$ together with the atom to which they are attached form a 4 to 10 membered carbocyclic, heteroaryl or heterocyclic ring, each of which is optionally substituted with one to three groups independently selected from halogen, cyano, nitro, trifluoromethyl, difluoromethoxy, trifluoromethoxy, azido, —NR'SO$_2$R'''', —SO$_2$NR'R'', —C(O)R'''', —C(O)R', —OC(O)R', —NR'C(O)OR'''', —NR'C(O)R'', —C(O) NR'R'', —SO$_2$R'''', —NR'R'', —NR'C(O)NR''R''', —NR'C (NCN)NR''R''', —OR', aryl, heteroaryl, arylalkyl, heteroarylalkyl, heterocyclyl, and heterocyclylalkyl;

$R^6$ is selected from trifluoromethyl, $C_1$-$C_{10}$ alkyl, $C_3$-$C_{10}$ cycloalkyl, aryl, arylalkyl, heteroaryl, heteroarylalkyl, heterocyclyl, and heterocyclylalkyl, where each alkyl, cycloalkyl, aryl, heteroaryl and heterocyclyl portion is optionally substituted with one to five groups independently selected from oxo, halogen, cyano, nitro, trifluoromethyl, difluoromethoxy, trifluoromethoxy, azido, —NR'SO$_2$R'''', —SO$_2$NR'R'', —C(O)R', —C(O)OR', —OC(O)R', —NR'C(O)OR'''', —NR'C(O)R'', —C(O)NR'R'', —SO$_2$R'''', —NR'R', —NR'C(O)NR''R''', —NR'C(NCN)NR''R''', —OR', aryl, heteroaryl, arylalkyl, heteroarylalkyl, heterocyclyl, and heterocyclylalkyl;

$R^7$ is selected from hydrogen, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, aryl, arylalkyl, heteroaryl, heteroarylalkyl, heterocyclyl, and heterocyclylalkyl, where each alkyl, alkenyl, alkynyl, cycloalkyl, aryl, heteroaryl and heterocyclyl portion is optionally substituted with one to five groups independently selected from oxo, halogen, cyano, nitro, trifluoromethyl, difluoromethoxy, trifluoromethoxy, azido, —$NR^4SO_2R^6$, —$SO_2NR^3R^4$, —$C(O)R^3$, —$C(O)OR^3$, —$OC(O)R^3$, —$NR^4C(O)OR^6$, —$NR^4C(O)R^3$, —$C(O)NR^3R^4$, —$SO_2R^3$, —$NR^3R^4$, —$NR^5C(O)NR^3R^4$, —$NR^5C(NCN)NR^3R^4$, —$OR^3$, aryl, heteroaryl, arylalkyl, heteroarylalkyl, heterocyclyl, and heterocyclylalkyl;

W is selected from heteroaryl, heterocyclyl, —$C(O)OR^3$, —$C(O)NR^3R^4$, —$C(O)NR^4OR^3$, —$C(O)R^4OR^3$, —$C(O)(C_3$-$C_{10}$ cycloalkyl), —$C(O)(C_1$-$C_{10}$ alkyl), —$C(O)(aryl)$, —$C(O)(heteroaryl)$ and —$C(O)(heterocyclyl)$, each of which is optionally substituted with 1-5 groups independently selected from —$NR^3R^4$, —$OR^3$, —$R^2$, and $C_1$-$C_{10}$ alkyl, $C_2$-$C_{10}$ alkenyl, and $C_2$-$C_{10}$ alkynyl, each of which is optionally substituted with 1 or 2 groups independently selected from —$NR^3R^4$ and —$OR^3$;

$R^8$ is selected from hydrogen, —$SCF_3$, —Cl, —Br, —F, cyano, nitro, trifluoromethyl, difluoromethoxy, trifluoromethoxy, azido, —$OR^3$, —$C(O)R^3$, —$C(O)OR^3$, —$NR^4C(O)OR^6$, —$OC(O)R^3$, —$NR^4SO_2R^6$, —$SO_2NR^3R^4$, —$NR^4C(O)R^3$, —$C(O)NR^3R^4$, —$NR^5C(O)NR^3R^4$, —$NR^3R^4$, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, —$S(O)_j(C_1$-$C_6$ alkyl), —$S(O)_j(CR^4R^5)_m$-aryl, aryl, arylalkyl, heteroaryl, heteroarylalkyl, heterocyclyl, heterocyclylalkyl, —$O(CR^4R^5)_m$-aryl, —$NR^4(CR^4R^5)_m$-aryl, —$O(CR^4R^5)_m$-heteroaryl, —$NR^4(CR^4R^5)_m$-heteroaryl, —$O(CR^4R^5)_m$-heterocyclyl and —$NR^4(CR^4R^5)_m$-heterocyclyl, where each alkyl, alkenyl, alkynyl, cycloalkyl, aryl, heteroaryl and heterocyclyl portion is optionally substituted with one to five groups independently selected from oxo, halogen, cyano, nitro, trifluoromethyl, difluoromethoxy, trifluoromethoxy, azido, —$NR^4SO_2R^6$, —$SO_2NR^3R^4$, —$C(O)R^3$, —$C(O)OR^3$, —$OC(O)R^3$, —$NR^4C(O)OR^6$, —$NR^4C(O)R^3$, —$C(O)NR^3R^4$, —$NR^3R^4$, —$NR^5C(O)NR^3R^4$, —$NR^5C(NCN)NR^3R^4$, —$OR^3$, aryl, heteroaryl, arylalkyl, heteroarylalkyl, heterocyclyl, and heterocyclylalkyl;

m is 0, 1, 2, 3, 4 or 5; and j is 1 or 2.

DETAILED DESCRIPTION OF THE INVENTION

The novel compounds encompassed by the instant invention are those described by the general Formula I set forth above, and the pharmaceutically acceptable salts and prodrugs thereof.

The present invention also provides compounds of Formula I in which $R^7$ is $C_1$-$C_{10}$ alkyl, $C_3$-$C_7$ cycloalkyl, $C_3$-$C_7$ cycloalkylalkyl, $C_3$-$C_7$ heterocycloalkyl or $C_3$-$C_7$ heterocycloalkylalkyl each of which can be optionally substituted with 1-3 groups independently selected from oxo, halogen, cyano, nitro, trifluoromethyl, difluoromethoxy, trifluoromethoxy, azido, —$NR^4SO_2R^6$, —$SO_2NR^3R^4$, —C(O)$R^3$, —C(O)O$R^3$, —OC(O)$R^3$, —$SO_2R^3$, —$NR^4$C(O)O$R^6$, —$NR^4$C(O)$R^3$, —C(O)$NR^3R^4$, —$NR^3R^4$, —$NR^5$C(O)$NR^3R^4$, —$NR^5$C(NCN)$NR^3R^4$, —O$R^3$, aryl, heteroaryl, arylalkyl, heteroarylalkyl, heterocyclyl, and heterocyclylalkyl.

The present invention also provides compounds of Formula I wherein $R^8$ is —$OCF_3$, —Br or —Cl, $R^2$ is hydrogen, and $R^1$ is lower alkyl or halogen.

The present invention also provides compounds of Formula I wherein $R^9$ is hydrogen or halogen, and $R^{10}$ is hydrogen.

The present invention also provides compounds of Formula I wherein W is —C(O)O$R^3$ or —C(O)$NR^4OR^3$.

The present invention also provides compounds of Formula II:

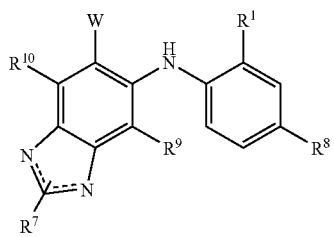

II wherein W, $R^1$, $R^7$, $R^8$, $R^9$ and $R^{10}$ are as defined above for Formula I.

The present invention also provides compounds of Formula II in which $R^7$ is $C_1$-$C_{10}$ alkyl, $C_3$-$C_7$ cycloalkyl or $C_3$-$C_7$ cycloalkylalkyl, each of which can be optionally substituted with 1-3 groups independently selected from oxo, halogen, cyano, nitro, trifluoromethyl, difluoromethoxy, trifluoromethoxy, azido, —$NR^4SO_2R^6$, —$SO_2NR^3R^4$, —C(O)$R^3$, —C(O)O$R^3$, —OC(O)$R^3$, —$SO_2R^3$, —$NR^4$C(O)O$R^6$, —$NR^4$C(O)$R^3$, —C(O)$NR^3R^4$, —$NR^3R^4$, —$NR^5$C(O)$NR^3R^4$, —$NR^5$C(NCN)$NR^3R^4$, —O$R^3$, aryl, heteroaryl, arylalkyl, heteroarylalkyl, heterocyclyl, and heterocyclylalkyl.

The present invention also provides compounds of Formula II wherein $R^8$ is —$OCF_3$, —Br or —Cl, and $R^1$ is lower alkyl or halogen.

The present invention also provides compounds of Formula II wherein $R^9$ is hydrogen or halogen, and $R^{10}$ is hydrogen.

The present invention also provides compounds of Formula II wherein W is —C(O)O$R^3$ or —C(O)$NR^4OR^3$.

The present invention also provides compounds of Formula III:

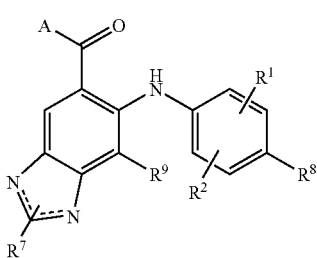

III wherein $R^1$, $R^2$, $R^7$, $R^8$ and $R^9$ are as defined above for Formula I, and A is —O$R^3$ or —$NR^4OR^3$, wherein $R^3$ and $R^4$ are as defined above for Formula I.

The present invention also provides compounds of Formula III in which $R^7$ is $C_1$-$C_{10}$ alkyl, $C_3$-$C_7$ cycloalkyl or $C_3$-$C_7$ cycloalkylalkyl, each of which can be optionally substituted with 1-3 groups independently selected from oxo, halogen, cyano, nitro, trifluoromethyl, difluoromethoxy, trifluoromethoxy, azido, —$NR^4SO_2R^6$, —$SO_2NR^3R^4$, —C(O)$R^3$, —C(O)O$R^3$, —OC(O)$R^3$, —$SO_2R^3$, —$NR^4$C(O)O$R^6$, —$NR^4$C(O)$R^3$, —C(O)$NR^3R^4$, —$NR^3R^4$, —$NR^5$C(O)$NR^3R^4$, —$NR^5$C(NCN)$NR^3R^4$, —O$R^3$, aryl, heteroaryl, arylalkyl, heteroarylalkyl, heterocyclyl, and heterocyclylalkyl.

The present invention also provides compounds of Formula III wherein $R^8$ is —$OCF_3$, —Br or —Cl, $R^2$ is hydrogen, and $R^1$ is lower alkyl or halogen.

The present invention also provides compounds of Formula III wherein $R^9$ is hydrogen or halogen.

The present invention also provides compounds of Formula III wherein $R^3$ is hydrogen or lower alkyl when A is —O$R^3$; and $R^4$ is hydrogen when A is —$NR^4OR^3$.

The present invention also provides compounds of Formula IIIa:

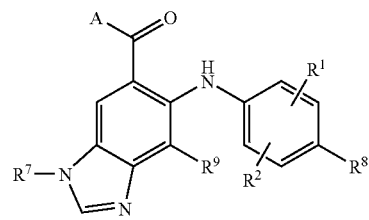

IIIa wherein $R^1$, $R^2$, $R^7$, $R^8$ and $R^9$ are as defined above for Formula I, and A is —O$R^3$ or —$NR^4OR^3$, wherein $R^3$ and $R^4$ are as defined above for Formula I.

The present invention also provides compounds of Formula IIIa in which $R^7$ is $C_1$-$C_{10}$ alkyl, $C_3$-$C_7$ cycloalkyl or $C_3$-$C_7$ cycloalkylalkyl, each of which can be optionally substituted with 1-3 groups independently selected from oxo, halogen, cyano, nitro, trifluoromethyl, difluoromethoxy, trifluoromethoxy, azido, —$NR^4SO_2R^6$, —$SO_2NR^3R^4$, —C(O)$R^3$, —C(O)O$R^3$, —OC(O)$R^3$, —$SO_2R^3$, —$NR^4$C(O)O$R^6$, —$NR^4$C(O)$R^3$, —C(O)$NR^3R^4$, —$NR^3R^4$, —$NR^5$C(O)$NR^3R^4$, —$NR^5$C(NCN)$NR^3R^4$, —O$R^3$, aryl, heteroaryl, arylalkyl, heteroarylalkyl, heterocyclyl, and heterocyclylalkyl.

The present invention also provides compounds of Formula IIIa wherein $R^8$ is —$OCF_3$, —Br or —Cl, $R^2$ is hydrogen, and $R^1$ is lower alkyl or halogen.

The present invention also provides compounds of Formula IIIa wherein $R^9$ is hydrogen or halogen.

The present invention also provides compounds of Formula IIIa wherein $R^3$ is hydrogen or lower alkyl when A is —$OR^3$; and $R^4$ is hydrogen when A is —$NR^4OR^3$.

The present invention also provides compounds of Formula IIIb:

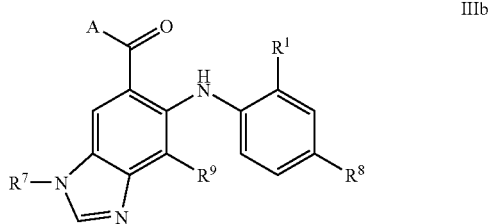

IIIb wherein R', $R^7$, $R^8$ and $R^9$ are as defined above for Formula I, and A is —$OR^3$ or —$NR^4OR^3$, wherein $R^3$ and $R^4$ are as defined above for Formula I.

The present invention also provides compounds of Formula IIIb in which $R^7$ is $C_1$-$C_{10}$ alkyl, $C_3$-$C_7$ cycloalkyl or $C_3$-$C_7$ cycloalkylalkyl, each of which can be optionally substituted with 1-3 groups independently selected from oxo, halogen, cyano, nitro, trifluoromethyl, difluoromethoxy, trifluoromethoxy, azido, —$NR^4SO_2R^6$, —$SO_2NR^3R^4$, —C(O)$R^3$, —C(O)$OR^3$, —OC(O)$R^3$, —$SO_2R^3$, —$NR^4C(O)OR^6$, —$NR^4C(O)R^3$, —C(O)$NR^3R^4$, —$NR^3R^4$, —$NR^5C(O)NR^3R^4$, —$NR^5C(NCN)NR^3R^4$, —$OR^3$, aryl, heteroaryl, arylalkyl, heteroarylalkyl, heterocyclyl, and heterocyclylalkyl.

The present invention also provides compounds of Formula IIIb wherein $R^8$ is —$OCF_3$, —Br or —Cl, and $R^1$ is lower alkyl or halogen.

The present invention also provides compounds of Formula IIIb wherein $R^9$ is fluoro or chloro.

The present invention also provides compounds of Formula IIIb wherein $R^3$ is hydrogen or lower alkyl when A is —$OR^3$; and $R^4$ is hydrogen when A is —$NR^4OR^3$.

Except as expressly defined otherwise, the following definition of terms is employed throughout this specification.

By "$C_1$-$C_{10}$ alkyl", "alkyl" and "lower alkyl" in the present invention is meant straight or branched chain alkyl groups having 1-10 carbon atoms, such as, methyl, ethyl, propyl, isopropyl, n-butyl, sec-butyl, tert-butyl, pentyl, 2-pentyl, isopentyl, neopentyl, hexyl, 2-hexyl, 3-hexyl, 3-methylpentyl, heptyl, octyl, and the like. Preferred alkyl radicals are $C_{1-6}$ alkyl. More preferred alkyl radicals are $C_{1-3}$ alkyl.

By "$C_2$-$C_{10}$ alkenyl", "lower alkenyl" and "alkenyl" means straight and branched hydrocarbon radicals having from 2 to 10 carbon atoms and at least one double bond and includes ethenyl, propenyl, 1-but-3-enyl, 1-pent-3-enyl, 1-hex-5-enyl and the like. More preferred are lower alkenyl having 3-5 carbon atoms.

By "$C_2$-$C_{10}$ alkynyl", "lower alkynyl" and "alkynyl" means straight and branched hydrocarbon radicals having from 2 to 10 carbon atoms and at least one triple bond and includes ethynyl, propynyl, butynyl, pentyn-2-yl and the like. More preferred are alkynyl having 3-5 carbon atoms.

By the term "halogen" in the present invention is meant fluorine, bromine, chlorine, and iodine.

By "aryl" is meant an aromatic carbocyclic group having a single ring (e.g., phenyl), multiple rings (e.g., biphenyl), or multiple condensed rings in which at least one is aromatic, (e.g., 1,2,3,4-tetrahydronaphthyl, naphthyl), which is optionally mono-, di-, or trisubstituted with, e.g., halogen, lower alkyl, lower alkoxy, trifluoromethyl, aryl, heteroaryl, and hydroxy.

By "heteroaryl" is meant one or more aromatic ring systems of 5-, 6-, or 7-membered rings which includes fused ring systems (at least one of which is aromatic) of 5-10 atoms containing at least one and up to four heteroatoms selected from nitrogen, oxygen, or sulfur. Examples of heteroaryl groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. Spiro moieties are also included within the scope of this definition. Heteroaryl groups are optionally mono-, di-, or trisubstituted with, e.g., halogen, lower alkyl, lower alkoxy, haloalkyl, aryl, heteroaryl, and hydroxy.

As used herein, the term "carbocycle", "carbocyclyl", "cycloalkyl" or "$C_3$-$C_{10}$ cycloalkyl" refers to saturated carbocyclic radicals having three to ten carbon atoms. The cycloalkyl can be monocyclic, or a polycyclic fused system, and can be fused to an aromatic ring. Examples of such radicals include cyclopropyl, cyclobutyl, cyclopentyl and cyclohexyl. The cycloalkyl groups herein are unsubstituted or, as specified, substituted in one or more substitutable positions with various groups. For example, such cycloalkyl groups may be optionally substituted with, for example, $C_1$-$C_6$ alkyl, $C_1$-$C_6$ alkoxy, halogen, hydroxy, cyano, nitro, amino, mono($C_1$-$C_6$)alkylamino, di($C_1$-$C_6$)alkylamino, $C_2$-$C_6$alkenyl, $C_2$-$C_6$alkynyl, $C_1$-$C_6$ haloalkyl, $C_1$-$C_6$ haloalkoxy, amino($C_1$-$C_6$)alkyl, mono($C_1$-$C_6$)alkylamino($C_1$-$C_6$)alkyl or di($C_1$-$C_6$)alkylamino($C_1$-$C_6$)alkyl.

By "heterocycle" or "heterocyclyl" is meant one or more carbocyclic ring systems of 5-, 6-, or 7-membered rings which includes fused ring systems of 4-10 atoms containing at least one and up to four heteroatoms selected from nitrogen, oxygen, or sulfur, and with the proviso that the ring of the group does not contain two adjacent O or S atoms. A fused system can be a heterocycle fused to an aromatic group. Preferred heterocycles include, but are not limited to, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 3-azabicyco[3.1.0]hexanyl, 3-azabicyclo[4.1.0]heptanyl, azabicyclo[2.2.2]hexanyl, 3H-indolyl and quinolizinyl. Spiro moieties are also included within the scope of this definition. The foregoing groups, as derived from the groups listed above, may be C-attached or N-attached where such is possible. For instance, a group derived from pyrrole may be pyrrol-1-yl (N-attached) or pyrrol-3-yl (C-attached). Further, a group derived from imidazole may be imidazol-1-yl (N-attached) or imidazol-3-yl (C-attached). An example of a heterocyclic group wherein 2 ring carbon atoms are substituted with oxo (=O) moieties is 1,1-dioxo-thiomorpholinyl. The heterocycle groups herein are unsubstituted or, as specified, substituted in one or more substitutable positions with various groups. For example, such heterocycle groups may be optionally substituted with, for example, $C_1$-$C_6$ alkyl, $C_1$-$C_6$ alkoxy, halogen, hydroxy, cyano, nitro, amino, mono($C_1$-$C_6$)alkylamino, di($C_1$-$C_6$)alkylamino, $C_2$-$C_6$ alkenyl, $C_2$-$C_6$ alkynyl, $C_1$-$C_6$ haloalkyl, $C_1$-$C_6$ haloalkoxy, amino ($C_1$-$C_6$)alkyl, mono($C_1$-$C_6$)alkylamino($C_1$-$C_6$)alkyl or di($C_1$-$C_6$)alkylamino($C_1$-$C_6$)alkyl.

The term "arylalkyl" means an alkyl moiety (as defined above) substituted with one or more aryl moiety (also as defined above). More preferred arylalkyl radicals are aryl-$C_{1-3}$-alkyls. Examples include benzyl, phenylethyl, and the like.

The term "heteroarylalkyl" means an alkyl moiety (as defined above) substituted with a heteroaryl moiety (also as defined above). More preferred heteroarylalkyl radicals are 5- or 6-membered heteroaryl-$C_{1-3}$-alkyls. Examples include, oxazolylmethyl, pyridylethyl and the like.

The term "heterocyclylalkyl" means an alkyl moiety (as defined above) substituted with a heterocyclyl moiety (also defined above). More preferred heterocyclylalkyl radicals are 5- or 6-membered heterocyclyl-$C_{1-3}$-alkyls. Examples include tetrahydropyranylmethyl.

The term "cycloalkylalkyl" means an alkyl moiety (as defined above) substituted with a cycloalkyl moiety (also defined above). More preferred heterocyclyl radicals are 5- or 6-membered cycloalkyl-$C_{1-3}$-alkyls. Examples include cyclopropylmethyl.

The term "Me" means methyl, "Et" means ethyl, "Bu" means butyl and "Ac" means acetyl.

The phrase "pharmaceutically acceptable salt(s)", as used herein, unless otherwise indicated, includes salts of acidic and basic groups which may be present in the compounds of the present invention. The compounds of the present invention that are basic in nature are capable of forming a wide variety of salts with various inorganic and organic acids. The acids that may be used to prepare pharmaceutically acceptable acid addition salts of such basic compounds of the present invention are those that form non-toxic acid addition salts, i.e., salts containing pharmaceutically acceptable anions, such as the acetate, benzenesulfonate, benzoate, bicarbonate, bisulfate, bitartrate, borate, bromide, calcium, camsylate, carbonate, chloride, clavulanate, citrate, dihydrochloride, edislyate, estolate, esylate, ethylsuccinate, fumarate, gluceptate, gluconate, glutamate, glycollylarsanilate, hexylresorcinate, hydrabamine, hydrobromide, hydrochloride, iodide, isothionate, lactate, lactobionate, laurate, malate, maleate, mandelate, mesylate, methylsulfate, mucate, napsylate, nitrate, oleate, oxalate, pamoate (embonate), palimitate, pantothenate, phosphate/diphosphate, polygalacturonate, salicylate, stearate, subacetate, succinate, tannate, tartrate, teoclate, tosylate, triethiodode, and valerate salts. Since a single compound of the present invention may include more than one acidic or basic moieties, the compounds of the present invention may include mono, di or tri-salts in a single compound.

In the case of an acidic moiety in a compound of the present invention, a salt may be formed by treatment of a compound of the present invention with a basic compound, particularly an inorganic base. Preferred inorganic salts are those formed with alkali and alkaline earth metals such as lithium, sodium, potassium, barium and calcium. Preferred organic base salts include, for example, ammonium, dibenzylammonium, benzylammonium, 2-hydroxyethylammonium, bis(2-hydroxyethyl)ammonium, phenylethylbenzylamine, dibenzyl-ethylenediamine, and the like salts. Other salts of acidic moieties may include, for example, those salts formed with procaine, quinine and N-methylglusoamine, plus salts formed with basic amino acids such as glycine, ornithine, histidine, phenylglycine, lysine and arginine. An especially preferred salt is a sodium or potassium salt of a compound of the present invention.

With respect to basic moieties, a salt is formed by the treatment of a compound of the present invention with an acidic compound, particularly an inorganic acid. Preferred inorganic salts of this type may include, for example, the hydrochloric, hydrobromic, hydroiodic, sulfuric, phosphoric or the like salts. Preferred organic salts of this type, may include, for example, salts formed with formic, acetic, succinic, citric, lactic, maleic, fumaric, palmitic, cholic, pamoic, mucic, D-glutamic, D-camphoric, glutaric, glycolic, phthalic, tartaric, lauric, stearic, salicyclic, methanesulfonic, benzenesulfonic, paratoluenesulfonic, sorbic, puric, benzoic, cinnamic and the like organic acids. An especially preferred salt of this type is a hydrochloride or sulfate salt of a compound of the present invention.

In the compounds of the present invention, where terms such as $(CR^4R^5)_m$ or $(CR^4R^5)_t$ are used, $R^4$ and $R^5$ may vary with each iteration of m or t above 1. For instance, where m or t is 2, the terms $(CR^4R^5)_m$ or $(CR^4R^5)_t$ may equal —$CH_2CH_2$— or —$CH(CH_3)C(CH_2CH_3)(CH_2CH_2CH_3)$— or any number of similar moieties falling within the scope of the definitions of $R^4$ and $R^5$.

Certain compounds of the present invention may have asymmetric centers and therefore exist in different enantiomeric forms. All optical isomers and stereoisomers of the compounds of the present invention, and mixtures thereof, are considered to be within the scope of the invention. With respect to the compounds of the present invention, the invention includes the use of a racemate, one or more enantiomeric forms, one or more diastereomeric forms, or mixtures thereof. The compounds of the present invention may also exist as tautomers. This invention relates to the use of all such tautomers and mixtures thereof.

The subject invention also includes isotopically-labeled compounds, which are identical to those recited in the present invention, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, sulfur, fluorine and chloride, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically-labeled compounds of the present invention, for example those into which radioactive isotopes such as $^3H$ and $^{14}C$ are incorporated, are useful in drug and/or substrate tissue distribution assays. Tritiated, i.e., $^3H$ and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labeled compound of the present invention and prodrugs thereof can generally be prepared by carrying out procedures disclosed in the Schemes and/or in the Examples and Preparations below, by substituting a readily available isotopically labeled reagent for a non-isotopically labeled reagent.

This invention also encompasses pharmaceutical compositions containing a compound of Formulas I-IIIb and methods of treating proliferative disorders, or abnormal cell growth, by administering prodrugs of compounds of the present invention. Compounds of the present invention having free amino, amido, hydroxy or carboxylic groups can be converted into prodrugs. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of the present invention. The amino acid residues include but are not limited to the 20 naturally occurring amino acids commonly designated by three letter symbols and also includes 4-hydroxyproline, hydroxylysine, demosine, isodemosine, 3-methylhistidine, norvaline, beta-alanine, gamma-aminobutyric acid, cirtulline, homocysteine, homoserine, ornithine and methionine sulfone. Additional types of prodrugs are also encompassed. For instance, free carboxyl groups can be derivatized as amides or alkyl esters. Free hydroxy groups may be derivatized using groups including but not limited to hemisuccinates, phosphate esters, dimethylaminoacetates, and phosphoryloxymethyloxycarbonyls, as outlined in *Advanced Drug Delivery Reviews,* 1996, 19, 115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in *J. Med. Chem.,* 1996, 39, 10. Free amines can also be derivatized as amides, sulfonamides or phosphonamides. All of these prodrug moieties may incorporate groups including but not limited to ether, amine and carboxylic acid functionalities.

It is to be understood that in instances where two or more radicals are used in succession to define a substituent attached to a structure, the first named radical is considered to be terminal and the last named radical is considered to be attached to the structure in question. Thus, for example, the radical arylalkyl is attached to the structure in question by the alkyl group.

The invention also relates to a pharmaceutical composition for the treatment of a hyperproliferative disorder in a mammal which comprises a therapeutically effective amount of a compound of the present invention, or a pharmaceutically acceptable salt, prodrug or hydrate thereof, and a pharmaceutically acceptable carrier. In one embodiment, said pharmaceutical composition is for the treatment of cancer such as brain, lung, squamous cell, bladder, gastic, pancreatic, breast, head, neck, renal, kidney, ovarian, prostate, colorectal, esophageal, testicular, gynecological or thyroid cancer. In another embodiment, said pharmaceutical composition is for the treatment of a non-cancerous hyperproliferative disorder such as benign hyperplasia of the skin (e.g., psoriasis), restenosis, or prostate (e.g., benign prostatic hypertrophy (BPH)).

The invention also relates to a pharmaceutical composition for the treatment of pancreatitis or kidney disease (including proliferative glomerulonephritis and diabetes-induced renal disease) or the treatment of pain in a mammal which comprises a therapeutically effective amount of a compound of the present invention, or a pharmaceutically acceptable salt, prodrug or hydrate thereof, and a pharmaceutically acceptable carrier.

The invention also relates to a pharmaceutical composition for the prevention of blastocyte implantation in a mammal which comprises a therapeutically effective amount of a compound of the present invention, or a pharmaceutically acceptable salt, prodrug or hydrate thereof, and a pharmaceutically acceptable carrier.

The invention also relates to a pharmaceutical composition for treating a disease related to vasculogenesis or angiogenesis in a mammal which comprises a therapeutically effective amount of a compound of the present invention, or a pharmaceutically acceptable salt, prodrug or hydrate thereof, and a pharmaceutically acceptable carrier. In one embodiment, said pharmaceutical composition is for treating a disease selected from the group consisting of tumor angiogenesis, chronic inflammatory disease such as rheumatoid arthritis, atherosclerosis, inflammatory bowel disease, skin diseases such as psoriasis, eczema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer.

The invention also relates to a method of treating a hyperproliferative disorder in a mammal that comprises administering to said mammal a therapeutically effective amount of a compound of the present invention, or a pharmaceutically acceptable salt, prodrug or hydrate thereof. In one embodiment, said method relates to the treatment of cancer such as brain, lung, squamous cell, bladder, gastric, pancreatic, breast, head, neck, renal, kidney, ovarian, prostate, colorectal, esophageal, testicular, gynecological or thyroid cancer. In another embodiment, said method relates to the treatment of a non-cancerous hyperproliferative disorder such as benign hyperplasia of the skin (e.g., psoriasis), restenosis, or prostate (e.g., benign prostatic hypertrophy (BPH)).

The invention also relates to a method for the treatment of a hyperproliferative disorder in a mammal that comprises administering to said mammal a therapeutically effective amount of a compound of the present invention, or a pharmaceutically acceptable salt, prodrug or hydrate thereof, in combination with an anti-tumor agent selected from the group consisting of mitotic inhibitors, alkylating agents, anti-metabolites, intercalating antibiotics, growth factor inhibitors, cell cycle inhibitors, enzyme inhibitors, topoisomerase inhibitors, biological response modifiers, anti-hormones, angiogenesis inhibitors, and anti-androgens.

The invention also relates to a method of treating pancreatitis or kidney disease in a mammal that comprises administering to said mammal a therapeutically effective amount of a compound of the present invention, or a pharmaceutically acceptable salt, prodrug or hydrate thereof.

The invention also relates to a method of preventing blastocyte implantation in a mammal that comprises administering to said mammal a therapeutically effective amount of a compound of the present invention, or a pharmaceutically acceptable salt, prodrug or hydrate thereof.

The invention also relates to a method of treating diseases related to vasculogenesis or angiogenesis in a mammal that comprises administering to said mammal a therapeutically effective amount of a compound of the present invention, or a pharmaceutically acceptable salt, prodrug or hydrate thereof. In one embodiment, said method is for treating a disease selected from the group consisting of tumor angiogenesis, chronic inflammatory disease such as rheumatoid arthritis, atherosclerosis, inflammatory bowel disease, skin diseases such as psoriasis, eczema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer.

Patients that can be treated with compounds of the present invention, or pharmaceutically acceptable salts, prodrugs and hydrates of said compounds, according to the methods of this invention include, for example, patients that have been diagnosed as having psoriasis, restenosis, atherosclerosis, BPH, lung cancer, bone cancer, CMML, pancreatic cancer, skin cancer, cancer of the head and neck, cutaneous or intraocular melanoma, uterine cancer, ovarian cancer, rectal cancer, cancer of the anal region, stomach cancer, colon cancer, breast cancer, testicular, gynecologic tumors (e.g., uterine sarcomas, carcinoma of the fallopian tubes, carcinoma of the endometrium, carcinoma of the cervix, carcinoma of the vagina or carcinoma of the vulva), Hodgkin's disease, cancer of the esophagus, cancer of the small intestine, cancer of the endocrine system (e.g., cancer of the thyroid, parathyroid or adrenal glands), sarcomas of soft tissues, cancer of the urethra, cancer of the penis, prostate cancer, chronic or acute leukemia, solid tumors of childhood, lymphocytic lymphomas, cancer of the bladder, cancer of the kidney or ureter (e.g., renal cell carcinoma, carcinoma of the renal pelvis), or neoplasms of the central nervous system (e.g., primary CNS lymphoma, spinal axis tumors, brain stem gliomas or pituitary adenomas).

This invention also relates to a pharmaceutical composition for inhibiting abnormal cell growth in a mammal which comprises an amount of a compound of the present invention, or a pharmaceutically acceptable salt or solvate or prodrug thereof, in combination with an amount of a chemotherapeutic, wherein the amounts of the compound, salt, solvate, or prodrug, and of the chemotherapeutic are together effective in inhibiting abnormal cell growth. Many chemotherapeutics are presently known in the art. In one embodiment, the chemotherapeutic is selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, angiogenesis inhibitors, and anti-androgens.

This invention further relates to a method for inhibiting abnormal cell growth in a mammal or treating a hyperproliferative disorder which method comprises administering to the mammal an amount of a compound of the present invention, or a pharmaceutically acceptable salt or solvate or prodrug thereof, in combination with radiation therapy, wherein the amounts of the compound, salt, solvate, or prodrug, is in combination with the radiation therapy effective in inhibiting abnormal cell growth or treating the hyperproliferative disorder in the mammal. Techniques for administering radiation therapy are known in the art, and these techniques can be used in the combination therapy described herein. The administration of the compound of the invention in this combination therapy can be determined as described herein.

It is believed that the compounds of the present invention can render abnormal cells more sensitive to treatment with radiation for purposes of killing and/or inhibiting the growth of such cells. Accordingly, this invention further relates to a method for sensitizing abnormal cells in a mammal to treatment with radiation which comprises administering to the mammal an amount of a compound of the present invention or pharmaceutically acceptable salt or solvate or prodrug thereof, which amount is effective is sensitizing abnormal cells to treatment with radiation. The amount of the compound, salt, or solvate in this method can be determined according to the means for ascertaining effective amounts of such compounds described herein.

The invention also relates to a method of and to a pharmaceutical composition of inhibiting abnormal cell growth in a mammal which comprises an amount of a compound of the present invention, or a pharmaceutically acceptable salt or solvate thereof, a prodrug thereof, or an isotopically-labeled derivative thereof, and an amount of one or more substances selected from anti-angiogenesis agents, signal transduction inhibitors, and antiproliferative agents.

Anti-angiogenesis agents, such as MMP-2 (matrix-metalloprotienase 2) inhibitors, MMP-9 (matrix-metalloprotienase 9) inhibitors, and COX-II (cyclooxygenase II) inhibitors, can be used in conjunction with a compound of the present invention and pharmaceutical compositions described herein. Examples of useful COX-II inhibitors include CELEBREX™ (alecoxib), valdecoxib, and rofecoxib. Examples of useful matrix metalloprotienase inhibitors are described in WO 96/33172, WO 96/27583, European Patent Application No. 97304971.1, European Patent Application No. 99308617.2, WO 98/07697, WO 98/03516, WO 98/34918, WO 98/34915, WO 98/33768, WO 98/30566, European Patent Publication 606,046, European Patent Publication 931,788, WO 90/05719, WO 99/52910), WO 99/52889, WO 99/29667, PCT International Application No. PCT/IB98/01113, European Patent Application No. 99302232.1, Great Britain Patent Application No. 9912961.1, U.S. Pat. No. 5,863,949, U.S. Pat. No. 5,861,510, and European Patent Publication 780,386, all of which are incorporated herein in their entireties by reference. Preferred MMP-2 and MMP-9 inhibitors are those that have little or no activity inhibiting MMP-1. More preferred, are those that selectively inhibit MMP-2 and/or MMP-9 relative to the other matrix-metalloproteinases (i.e., MMP-1, MMP-3, MMP-4, MMP-5, MMP-6, MMP-7, MMP-8, MMP-10, MMP-11, MMP-12, and MMP-13).

Some specific examples of MMP inhibitors useful in the present invention are AG-3340, RO 32-3555, and RS 13-0830.

The terms "abnormal cell growth" and "hyperproliferative disorder" are used interchangeably in this application.

"Abnormal cell growth", as used herein, unless otherwise indicated, refers to cell growth that is independent of normal regulatory mechanisms (e.g., loss of contact inhibition). This includes, for example, the abnormal growth of: (1) tumor cells (tumors) that proliferate by expressing a mutated tyrosine kinase or overexpression of a receptor tyrosine kinase; (2) benign and malignant cells of other proliferative diseases in which aberrant tyrosine kinase activation occurs; (3) any tumors that proliferate by receptor tyrosine kinases; (4) any tumors that proliferate by aberrant serine/threonine kinase activation; and (5) benign and malignant cells of other proliferative diseases in which aberrant serine/theroine kinase activation occurs.

The term "treating", as used herein, unless otherwise indicated, means reversing, alleviating, inhibiting the progress of, or preventing the disorder or condition to which such term applies, or one or more symptoms of such disorder or condition. The term "treatment", as used herein, unless otherwise indicated, refers to the act of treating as "treating" is defined immediately above.

Representative compounds of the present invention, which are encompassed by the present invention include, but are not limited to the compounds of the examples and their pharmaceutically acceptable acid or base addition salts or prodrugs thereof.

The examples presented below are intended to illustrate particular embodiments of the invention, and are not intended to limit the scope of the specification or the claims in any way.

An illustration of the preparation of compounds of the present invention is shown in Schemes 1-4.

Scheme 1
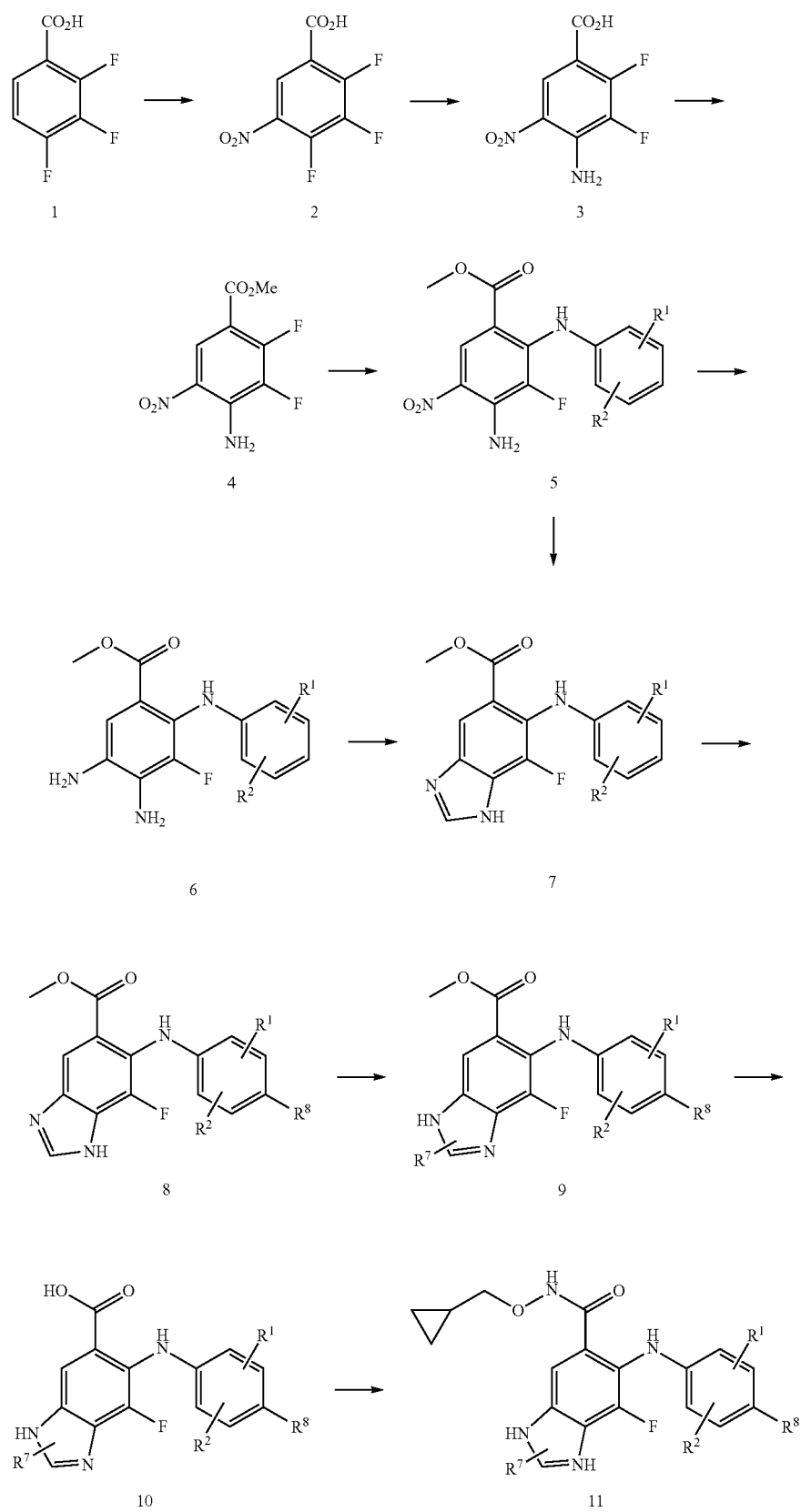

Scheme 1a
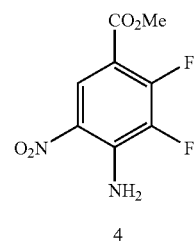
4
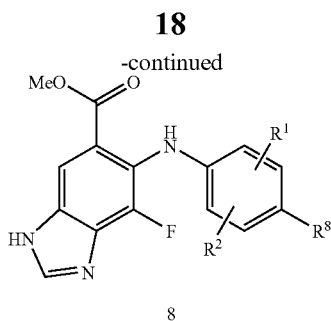
8
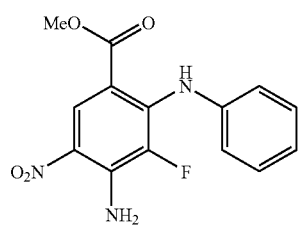
26
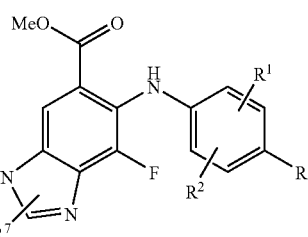
9
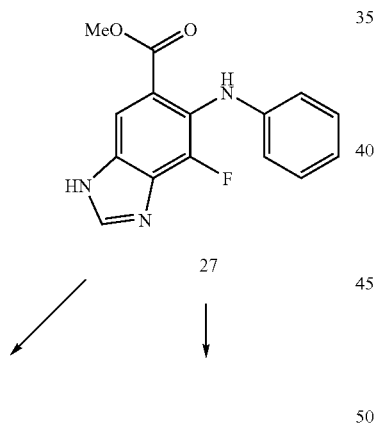
27
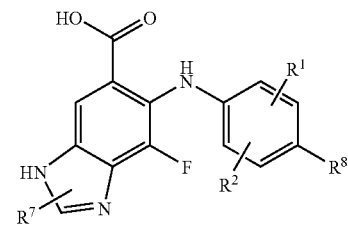
10
hydroxy amine
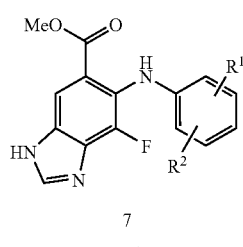
7
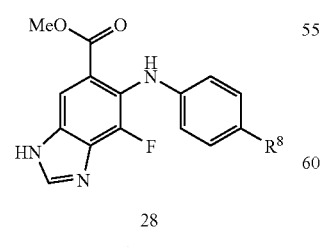
28
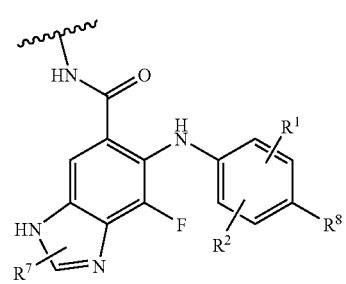
29

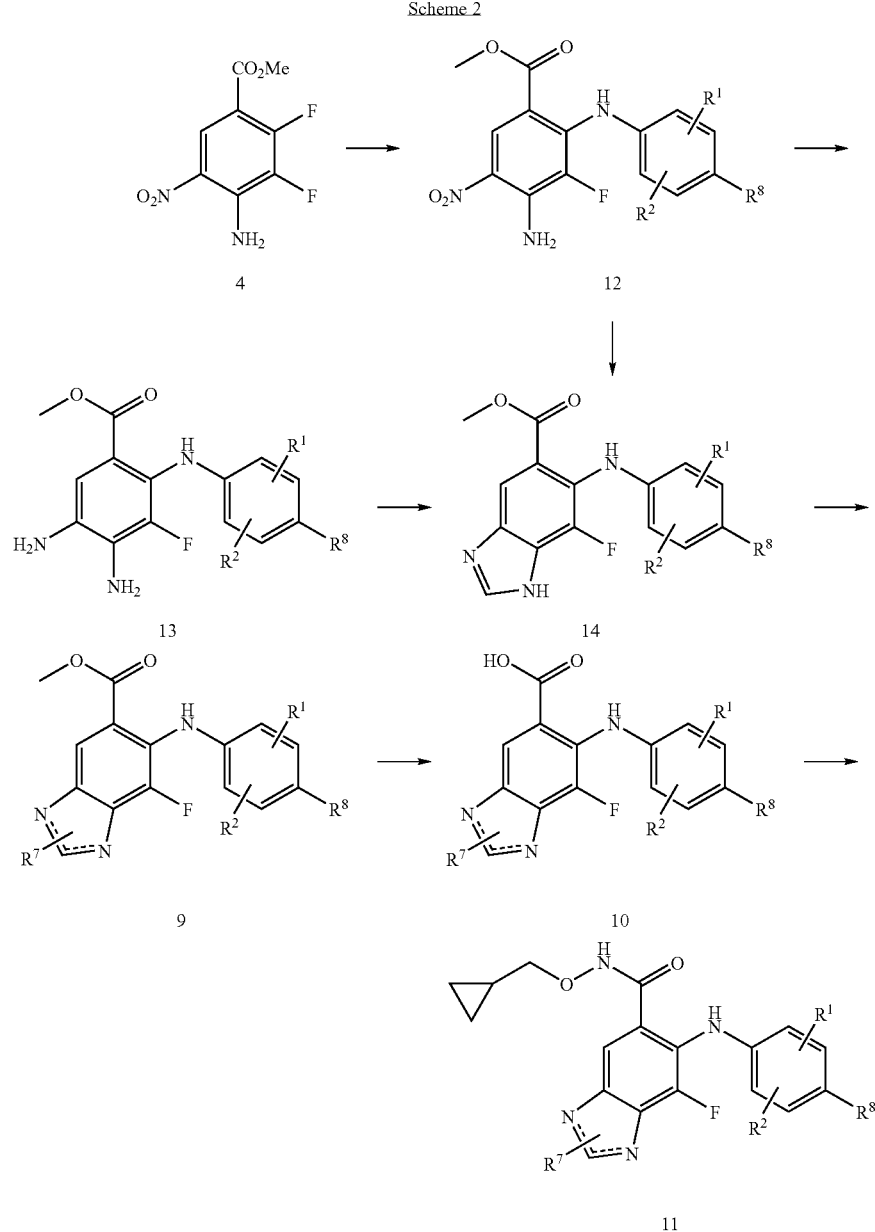
Scheme 2
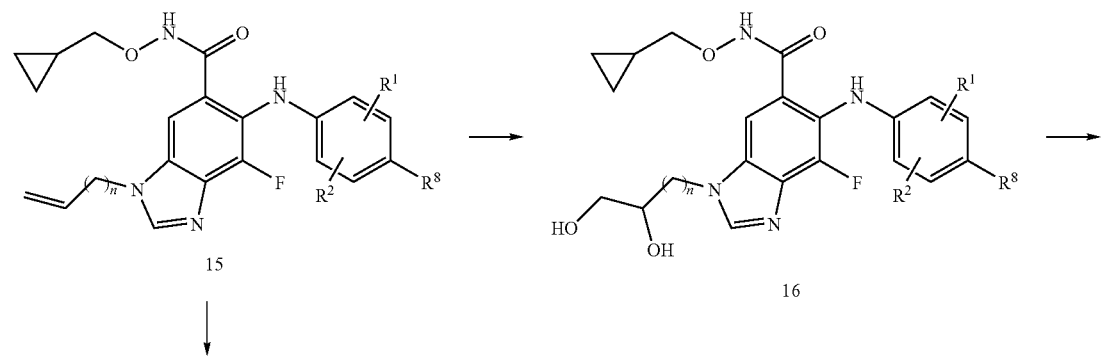
Scheme 3

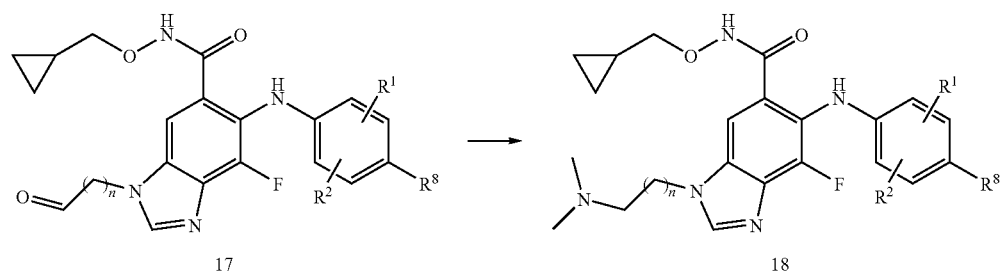
Scheme 4
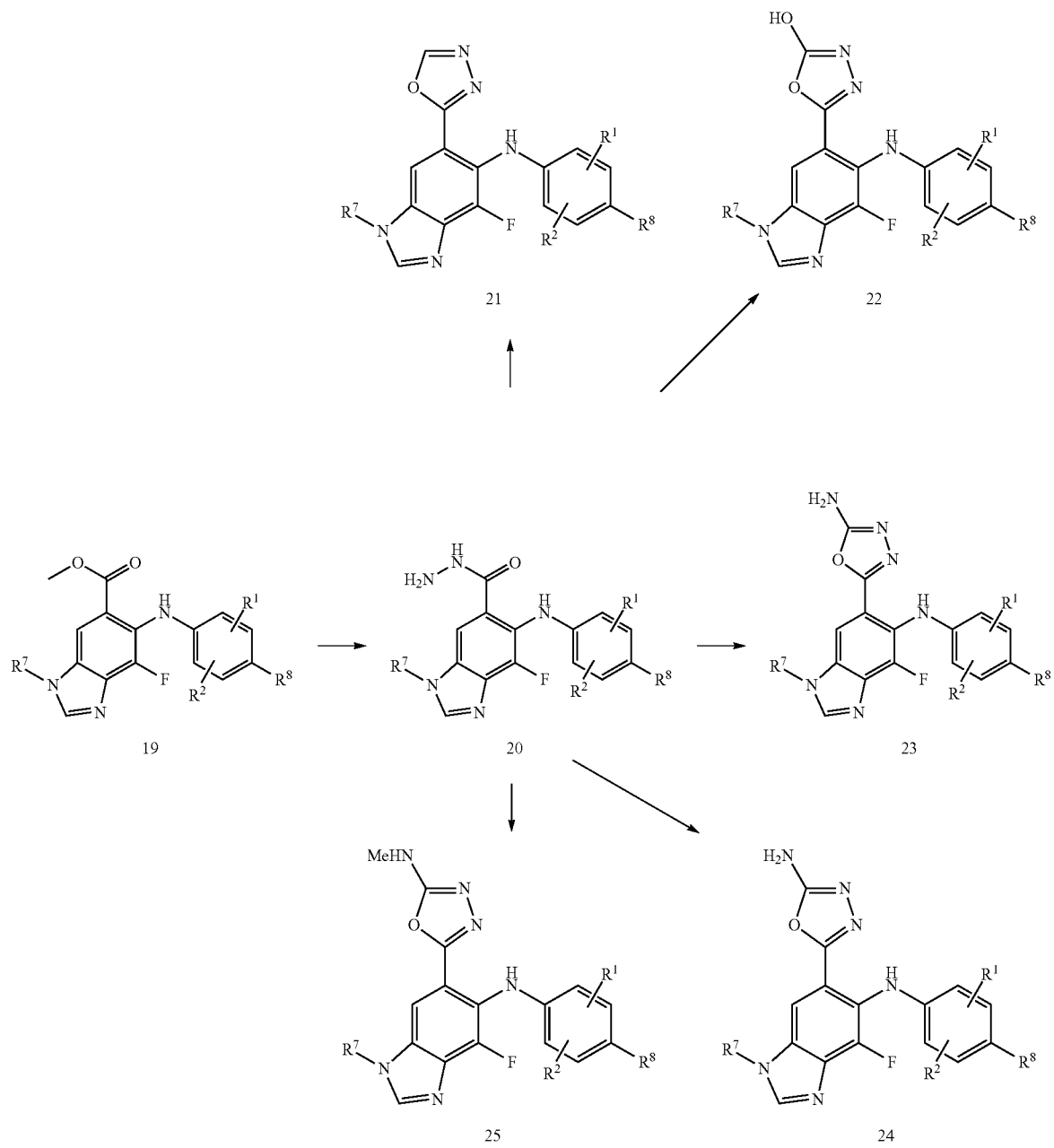

Scheme 5

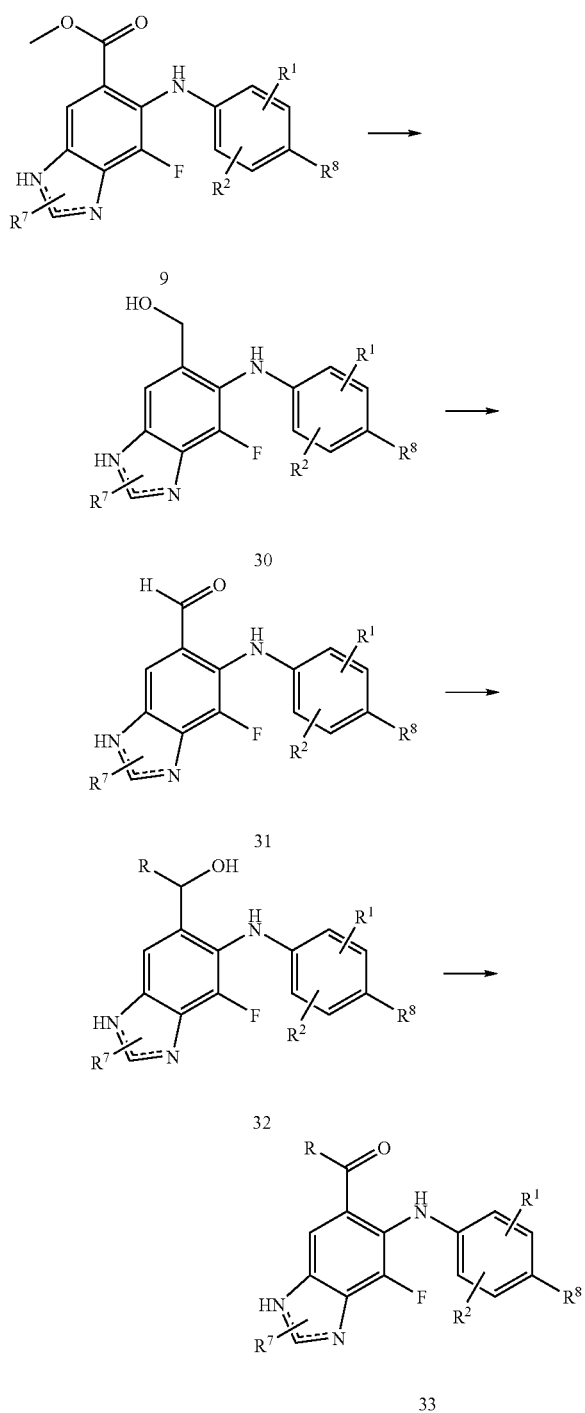

General synthetic methods which may be referred to for preparing some of the compounds of the present invention are provided in WO 00/42022. The foregoing patent application is incorporated herein by reference in its entirety. An illustration of the preparation of compounds of the present invention is shown in Schemes 1-4.

Scheme 1 illustrates the synthesis of compounds of the present invention. In step 1, the acid is nitrated using standard conditions preferable fuming nitric acid in $H_2SO_4$. In step 2, the aniline is prepared by fluoride displacement with $NH_4OH$ at room temperature in water followed by careful acidification with concentrated mineral acid to pH near 0. In step 3, the ester is prepared by standard methods including by not limited to Fisher Esterification (MeOH, $H_2SO_4$), and reaction with $TMSCHN_2$ in suitable organic solvents like PhMe/MeOH or THF/MeOH. In step 4, the dianilino derivative is prepared by heating (60 to 200° C.) the ester with an excess of the appropriate aniline neat or in an organic solvent like xylenes. For example, when $R^1$=Me and $R^2$=H the preferred method is stirring the ester with 10 equivalents aniline in xylenes at reflux until complete reaction. In step 5, the nitro arene is reduced to produce the diamine by standard reduction conditions, including by not limited to $H_2$, and Pd/C or $Pd(OH)_2$/C or Raney Nickel in organic solvent like EtOH or THF, Fe in AcOH, Zn in AcOH or Zn, $NH_4Cl$ (aqueous) in MeOH. In step 6, the diamine is cyclization by heating with formic acid neat or formamidine acetate in an appropriate solvent like EtOH. Alternatively, when $R^1$ or $R^2$ does not equal halo the nitro arene can be converted directly to the benzimidazole in step 7 by heating in formic acid with $Pd(OH)_2$/C or other palladium source like Pd/C. In step 8, a halide can be incorporated by standard methods, including but not limited to NBS or NCS and pTsOH in organic cosolvents like THF and MeOH. In step 9, the benzimidazole is alkylated to give a near equal mixture of N1 and N3 products which are separable by standard techniques, including, for example, chromatography and trituration. The alkylation is accomplished by use of an alkylating agent like an alkyl halide and base like NaH, or $K_2CO_3$ in suitable organic solvent like DMF or THF at temperatures ranging from 0 to 80° C. $R^7$ can be further modified by various synthetic methods known in the art, as exemplified below. In step 10, the ester is hydrolysized by standard saponification methods. The acid is then converted to the desired hydroxamate in step 11 by standard coupling procedures including but not limited to EDCI, HOBt or PyBOP and the appropriate hydroxylamine in suitable organic solvents like DMF, THF or methylene chloride.

Scheme 2 illustrates an example in which the $R^8$ substituent is on the aniline prior to the coupling procedure with the nitro ester. The reaction description is exactly like that for Scheme 1 except that there is no need to incorporated $R^8$ as it is present in the aniline from the beginning.

In Scheme 3, the preparation of N3 alkyl amino benzimidazole derivatives is illustrated. In step 1, the terminal alkene of the N3 alkylated benzimidazole hydroxamate is dihydroxylated using a suitable oxidant like $OsO_4$ in suitable solvent or $KMnO_4$ or $I_2$, AgOAc, AcOH, water. The diol is then further oxidized in step 2 by $NaIO_4$ or $Pb(OAc)_4$ in suitable biphasic mixture to give the aldehyde. Alternatively (step 3), the alkene can be directly converted to the aldehyde by standard methods including but not limited to ozone/$Me_2S$, $NaIO_4/OsO_4$ or $KMnO_4$. In step 4, the amine is prepared by reductive amination using standard methods such as $Na(CN)BH_3$, $Na(OAc)_3BH$, $NMe_4BH(OAc)_3$ with or without AcOH in a suitable solvent such as methylene chloride, acetonitrile or THF. The preferable reduction amination is to treat the aldehyde with amine, $Me_4NBH(OAc)_3$ and acetic acid in MeCN at room temperature.

Scheme 4 illustrates the preparation of compounds of the present invention where W is heterocyclic. In step 1, the methyl ester is converted to the hydrazide by stirring with hydrazine in a suitable solvent like EtOH at temperatures from 50 to 100° C. The desired heterocyclic derivative is then prepared by cyclization with the appropriate reagent. For oxadiazole 21 the hydrazide is treated with an orthoformate like triethyl orthoformate, and an acid catalyst like pTsOH in a suitable organic solvent like EtOH at elevated temperatures (50-100° C.). For hydroxy oxadiazole 22 the hydrazide can be cyclized with phosgene or a phosgene equivalent like triphosgene or carbonyl diimidazole in a suitable organic solvent like toluene at temperatures ranging from 50 to 120° C. The mercapto oxadizaole 23 can be prepared by reaction with carbon disulfide, and base like KOH in suitable organic solvent like EtOH at elevated temperatures (50-100° C.). The amino oxadiazole 24 can be made by reaction with BrCN and base like $NaHCO_3$, in a suitable biphasic solvent system like dioxane and water at room temperature. Finally, the substituted amino oxadiazole 25 can be prepared by first reacting the hydrazide with an appropriate isothiocyanate in a suitable organic solvent like DMF or THF at temperatures ranging from 25 to 100° C. The intermediate can be isolated or can be cyclized directly with the treatment of EDCI or other carbodiimide in suitable organic solvent like THF or DMF at temperatures ranging from room temperature to 80° C.

In Scheme 5, the preparation of keto benzimidazole derivatives is illustrated. In step 1, the methyl ester is converted to the benzyl alcohol by standard reductive methods, preferably LAH in THF at 0° C. or $NaBH_4$ in EtOH:THF at room temperature. Oxidation to the aldehyde can be accomplished in step 2 using $MnO_2$ in acetone:THF at 50° C. In step 3, organometallic reagents, such as organolithium reagents and Grignard reagents, can be added to the aldehyde in THF at low temperature (e.g., −78° C.) to give the substituted benzyl alcohol. The keto derivatives can be prepared in step 4 by oxidation of the benyzl alcohol under standard conditions such as Swern or Dess-Martin oxidation.

The compounds of the present invention may have asymmetric carbon atoms. Diastereomeric mixtures can be separated into their individual diastereomers on the basis of their physical chemical differences by methods known to those skilled in the art, for example, by chromatography or fractional crystallization. Enantiomers can be separated by converting the enantiomer mixture into a diastereomeric mixture by reaction with an appropriate optically active compound (e.g., alcohol), separating the diastereomers and converting (e.g., hydrolyzing) the individual diastereomers to the corresponding pure enantiomers. All such isomers, including diastereomeric mixtures and pure enantiomers are considered as part of the invention.

The activity of the compounds of the present invention may be determined by the following procedure. N-terminal 6 His-tagged, constitutively active MEK1 (2-393) is expressed in *E. coli* and protein is purified by conventional methods (Ahn et al., *Science* 1994, 265, 966-970). The activity of MEK1 is assessed by measuring the incorporation of $\gamma$-$^{33}$P-phosphate from $\gamma$-$^{33}$P-ATP onto N-terminal His tagged ERK2, which is expressed in *E. coli* and is purified by conventional methods, in the presence of MEK1. The assay is carried out in 96-well polypropylene plate. The incubation mixture (100 μL) comprises of 25 mM Hepes, pH 7.4, 10 mM $MgCl_2$, 5 mM β-glycerolphosphate, 100 μM Na-orthovanadate, 5 mM DTT, 5 nM MEK1, and 1 μM ERK2 Inhibitors are suspended in DMSO, and all reactions, including controls, are performed at a final concentration of 1% DMSO. Reactions are initiated by the addition of 10 μM ATP (with 0.5 μCi $\gamma$-$^{33}$P-ATP/well) and incubated at ambient temperature for 45 minutes. An equal volume of 25% TCA is added to stop the reaction and precipitate the proteins. Precipitated proteins are trapped onto glass fiber B filterplates, and excess labeled ATP is washed off using a Tomtec MACH III harvestor. Plates are allowed to air-dry prior to adding 30 μL/well of Packard Microscint 20, and plates are counted using a Packard TopCount. In this assay, compounds of the invention exhibited an $IC_{50}$ of less than 50 micromolar.

The following compounds were evaluated in the above assay and found to be active.

| Compound # |
|---|
| 8n |
| 11b |
| 11c |
| 11p |
| 18i |
| 29c |
| 29i |
| 29s |
| 29t |
| 29bb |
| 29lll |
| 29mmm |

Administration of the compounds of the present invention (hereinafter the "active compound(s)") can be effected by any method that enables delivery of the compounds to the site of action. These methods include oral routes, intraduodenal routes, parenteral injection (including intravenous, subcutaneous, intramuscular, intravascular or infusion), topical, and rectal administration.

The amount of the active compound administered will be dependent on the subject being treated, the severity of the disorder or condition, the rate of administration, the disposition of the compound and the discretion of the prescribing physician. However, an effective dosage is in the range of about 0.001 to about 100 mg per kg body weight per day, preferably about 1 to about 35 mg/kg/day, in single or divided doses. For a 70 kg human, this would amount to about 0.05 to 7 g/day, preferably about 0.05 to about 2.5 g/day. In some instances, dosage levels below the lower limit of the aforesaid range may be more than adequate, while in other cases still larger doses may be employed without causing any harmful side effect, provided that such larger doses are first divided into several small doses for administration throughout the day.

The active compound may be applied as a sole therapy or may involve one or more other anti-tumor substances, for example those selected from, for example, mitotic inhibitors, for example vinblastine; alkylating agents, for example cisplatin, carboplatin and cyclophosphamide; anti-metabolites, for example 5-fluorouracil, cytosine arabinside and hydroxyurea, or, for example, one of the preferred anti-metabolites disclosed in European Patent Application No. 239362 such as N-(5-[N-(3,4-dihydro-2-methyl-4-oxoquinazolin-6-ylmethyl)-N-methylamino]-2-thenoyl)-L-glutamic acid; growth factor inhibitors; cell cycle inhibitors; intercalating antibiotics, for example adriamycin and bleomycin; enzymes, for example, interferon; and anti-hormones, for example anti-estrogens such as Nolvadex™ (tamoxifen) or, for example anti-androgens such as Casodex™ (4'-cyano-3-(4-fluorophenylsulphonyl)-2-hydroxy-2-methyl-3'-(trifluoromethyl)propionanilide). Such conjoint treatment may be achieved by way of the simultaneous, sequential or separate dosing of the individual components of treatment.

The pharmaceutical composition may, for example, be in a form suitable for oral administration as a tablet, capsule, pill, powder, sustained release formulations, solution, or suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and a compound according to the invention as an active ingredient. In addition, it may include other medicinal or pharmaceutical agents, carriers, adjuvants, etc.

Exemplary parenteral administration forms include solutions or suspensions of active compounds in sterile aqueous solutions, for example, aqueous propylene glycol or dextrose solutions. Such dosage forms can be suitably buffered, if desired.

Suitable pharmaceutical carriers include inert diluents or fillers, water and various organic solvents. The pharmaceutical compositions may, if desired, contain additional ingredients such as flavorings, binders, excipients and the like. Thus for oral administration, tablets containing various excipients, such as citric acid may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes. Solid compositions of a similar type may also be employed in soft and hard filled gelatin capsules. Preferred materials, therefore, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

Methods of preparing various pharmaceutical compositions with a specific amount of active compound are known, or will be apparent, to those skilled in this art. For examples, see Remington's Pharmaceutical Sciences, Mack Publishing Company, Ester, Pa., 15$^{th}$ Edition (1975).

The examples and preparations provided below further illustrate and exemplify the compounds of the present invention and methods of preparing such compounds. It is to be understood that the scope of the present invention is not limited in any way by the scope of the following examples and preparations. In the following examples molecules with a single chiral center, unless otherwise noted, exist as a racemic mixture. Those molecules with two or more chiral centers, unless otherwise noted, exist as a racemic mixture of diastereomers. Single enantiomers/diastereomers may be obtained by methods known to those skilled in the art.

The disclosures in this application of all articles and references, including patents, are incorporated herein by reference.

The invention is illustrated further by the following examples which are not to be construed as limiting the invention in scope or spirit to the specific procedures described in them.

The starting materials and various intermediates may be obtained from commercial sources, prepared from commercially available organic compounds, or prepared using well known synthetic methods.

Representative examples of methods for preparing intermediates of the invention are set forth below.

EXAMPLES

Example 1

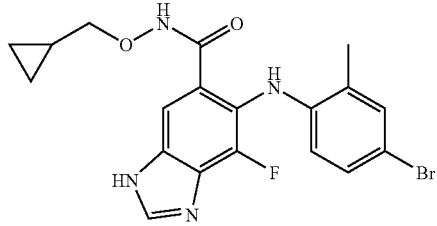

7-Fluoro-6-(4-bromo-2-methyl-phenylamino)-3H-benzoimidazole-5-carboxylic acid cyclopropyl-methoxy-amide (11a)

Step A: 2,3,4-Trifluoro-5-nitro-benzoic acid 2: A 3 liter three neck round bottom flask is charged with 125 mL $H_2SO_4$. Fuming nitric acid is added (8.4 mL, 199 mmol) and the mixture gently stirred. 2,3,4-Trifluorobenzoic acid 1 (25 g, 142 mmol) is added in 5 g portions over 90 minutes. The dark brownish yellow solution is stirred for 60 minutes at which time the reaction is complete. The reaction mixture is poured into 1 liter of an ice water mixture and extracted with diethyl ether (3×600 mL). The combined organic extracts are dried ($MgSO_4$) and concentrated under reduced pressure to give a yellow solid. The solid is suspended in hexanes and stirred for 30 minutes after which time it is filtered to give 29 g (92%) of clean desired product as an off-yellow solid: MS APCI (−) m/z 220 (M−1) detected.

Step B: 4-Amino-2,3-difluoro-5-nitro-benzoic acid 3: Ammonium hydroxide solution (~30% in water) (35 mL, 271 mmol) is added to a solution of 2,3,4-trifluoro-5-nitro-benzoic acid 2 (15 g, 67.8 mmol) in 30 mL water at 0° C. with stirring. Upon completion of ammonium hydroxide addition the reaction mixture is warmed to room temperature with stirring. After 2.5 hours, the reaction mixture is cooled to 0° C. and concentrated HCl is carefully added until pH of reaction mixture is near 0. The reaction mixture is diluted with water (30 mL) and extracted with diethyl ether (3×50 mL). The combined organic extracts are dried ($MgSO_4$) and concentrated under reduced pressure to give 14 g (95%) of pure desired product: MS APCI (−) m/z 217 (M−1) detected.

Step C: 4-Amino-2,3-difluoro-5-nitro-benzoic acid methyl ester 4: A 2 M solution of TMS diazomethane in hexanes (6.88 mL, 13.75 mmol) is added to a suspension of 4-amino-2,3-difluoro-5-nitro-benzoic acid 3 (2.00 g, 9.17 mmol) in 25 mL of 4:1 THF:MeOH at 0° C. under nitrogen atmosphere. Upon completion of addition, reaction mixture is warmed to room temperature. After 0.5 hours, excess TMS diazomethane is destroyed by the careful addition of acetic acid. The reaction is then concentrated under reduced pressure and dried in vacuo to give 1.95 g (92%) of pure desired product: MS APCI (−) m/z 231 (M−1) detected.

Step D: 4-Amino-3-fluoro-5-nitro-2-o-tolylamino-benzoic acid methyl ester 5a: 4-Amino-2,3-difluoro-5-nitro-benzoic acid methyl ester 4 (12.0 g, 51.7 mmol) is suspended in xylenes (60 mL) and ortho-toluidine is added (55.2 mL, 517 mmol). The reaction mixture is heated to reflux with stirring under a nitrogen atmosphere. After 36 hours, the reaction mixture is cooled to room temperature, diluted with diethyl ether and washed with 10% aqueous HCl solution. The aqueous washings are extracted with diethyl ether. The combined organic extracts are concentrated under reduced pressure. The residue is dissolved in methylene chloride and filtered through silica gel in a fitted funnel, rinsing with methylene chloride. Three fractions are recovered. The first (2 liter) is nearly clean by HPLC. The second (1 liter) and third (1 liter) fractions are only partially pure. The first fraction is concentrated under reduced pressure and triturated with diethyl ether to give 11.2 g (68%) of clean desired product as a bright yellow solid: MS APCI (−) m/z 318 (M−1) detected.

Step E: 7-Fluoro-6-o-tolylamino-1H-benzoimidazole-5-carboxylic acid methyl ester 7a: 4-Amino-3-fluoro-5-nitro-2-o-tolylamino-benzoic acid methyl ester 5a (1.57 g, 4.92 mmol), formic acid (25 mL, 26.5 mmol) and 20% Pd(OH)$_2$/C (1.57 g, 2.95 mmol) in 25 mL EtOH are heating with stirring to 95° C. After 16 hours, the reaction mixture is cooled to room temperature and 0.5 g 20% Pd(OH)$_2$/C and 10 mL formic acid added. The reaction mixture is heated to 95° C. with stirring. After 16 hours, the reaction mixture is cooled to room temperature and filtered through Celite rinsing with EtOH. The filtrate is concentrated under reduced pressure until the desired product precipitates. The desired product is collected by filtration. The filtrate is concentrated again until more desired product precipitates. The product is collected by filtration. Repeated EtOH concentration, product filtration several times. Recovered 1.09 g (74%) pure desired product: MS APCI (+) m/z 300 (M+1) detected; MS APCI (−) m/z 298 (M−1) detected.

Step F: 7-Fluoro-6-(4-bromo-2-methyl-phenylamino)-1H-benzoimidazole-5-carboxylic acid methyl ester 8a: 7-Fluoro-6-o-tolylamino-1H-benzoimidazole-5-carboxylic acid methyl ester 7a (2.00 g, 6.68 mmol) is suspended in 1:1 THF/MeOH (60 mL) and cooled to −78° C. under a nitrogen atmosphere. A solution of NBS (1.20 g, 6.75 mmol) in 1:1 THF/MeOH (5 mL) is added followed by a MeOH (5 mL) solution of TsOH.H$_2$O (1.9 g, 10.0 mmol). After 30 minutes, the reaction mixture is warmed to 0° C. and then after 1 hour warmed to room temperature. After 16 hours, more NBS (0.12 g, 0.67 mmol) is added and the reaction mixture is allowed to stir for 3 hours. The reaction mixture is quenched by the addition of 10% Na$_2$S$_2$O$_4$ solution. After 30 minutes, the reaction mixture is diluted with water and ethyl acetate and the layers separated. The aqueous layer is extracted with ethyl acetate. The combined organic extracts are dried (Na$_2$SO$_4$) and concentrated under reduced pressure. The recovered solid is triturated with methylene chloride to give 2.00 g (79%) pure desired product: MS APCI (+) m/z 380, 378 (M+1 Br pattern) detected.

Step G: 7-Fluoro-6-(4-bromo-2-methyl-phenylamino)-1H-benzoimidazole-5-carboxylic acid 10a: 7-Fluoro-6-(4-bromo-2-methyl-phenylamino)-1H-benzoimidazole-5-carboxylic acid methyl ester 8a (63 mg, 0.167 mmol) is suspended in MeOH (1.5 mL) and 20% NaOH (400 µl) is added. After 16 hours, the reaction mixture is cooled to 0° C. and 1 N HCl solution is added dropwise until pH is 2 to 3. The reaction mixture is diluted with ethyl acetate and water and the layers separated. The organic layer is washed with brine, dried (Na$_2$SO$_4$) and concentrated under reduced pressure to give 58 mg (95%) of desired product: MS APCI (+) m/z 366, 364 (M+1 Br pattern) detected; MS APCI (−) m/z 364, 362 (M−1 Br pattern) detected.

Step H: 7-Fluoro-6-(4-bromo-2-methyl-phenylamino)-1H-benzoimidazole-5-carboxylic acid cyclopropylmethoxyamide 11a: 7-Fluoro-6-(4-bromo-2-methyl-phenylamino)-1H-benzoimidazole-5-carboxylic acid 10a (48 mg, 0.132 mmol) is dissolved in 1:1 THF: methylene chloride (1 mL) and Hunig's base (0.23 µL, 1.32 mmol) is added followed by PyBOP (82 mg, 0.158 mmol). After a few minutes, cyclopropyl methyl hydroxylamine hydrochloride (20 mg, 0.158 mmol) (WO 00/42022) is added. After the reaction is complete, the mixture is partitioned between methylene chloride and saturated NaHCO$_3$ solution. The layers are separated and the organic layer is washed with saturated NaHCO$_3$ and brine. The organic layer is dried (Na$_2$SO$_4$) and concentrated under reduced pressure. After purification by FCC (elute with 20:1 methylene chloride/MeOH), 25 mg (45%) of pure desired product is isolated: MS ESI (+) m/z 435, 433 (M+1 Br pattern) detected; MS ESI (−) m/z 433, 431 (M−1 Br pattern) detected; $^1$H NMR (400 MHz, CDCl$_3$) δ 8.15 (s, 1H), 8.02 (s, 1H), 7.28 (s, 1H), 7.43 (d, 1H), 7.07 (dd, 1H), 6.36 (m, 1H), 3.70 (d, 2H), 2.38 (s, 3H), 0.86 (m, 1H), 0.41 (m, 2H), 0.13 (m, 2H); $^{19}$F NMR (376 MHz, CDCl$_3$) −134.05 (s).

Example 2

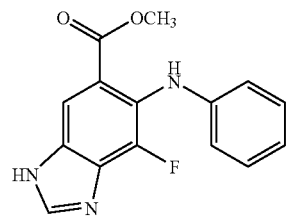

7-Fluoro-6-phenylamino-3H-benzoimidazole-5-carboxylic acid methyl ester (27a)

Step A: 4-Amino-3-fluoro-5-nitro-2-phenylamino-benzoic acid methyl ester 26a

4-Amino-2,3-difluoro-5-nitro-benzoic acid methyl ester 4 (23.48 g, 101.1 mmol), the product of Example 1, Step C, is suspended in xylenes (125 mL) and aniline (92 mL, 1011 mmol) is added. The reaction mixture is stirred at 125° C. for 16 hours under N$_2$. The reaction mixture is cooled to room temperature and solids precipitate out of solution. The solids are collected by filtration and are washed with xylenes and then diethyl ether. Recovered 22.22 g (72.78 mmol) of yellow solid which is pure desired product. The filtrate is concentrated under reduced pressure, redissolved in methylene chloride and flushed through a plug of silica gel eluting with methylene chloride. The desired fractions are concentrated under reduced pressure to give a brown solid which is triturated with diethyl ether to give 5.47 g (17.91 mmol) of yellow solid which is pure desired product. Combined product yield is 27.69 g (90%). MS APCI (−) m/z 304 (M−1) detected.

Step B: 7-Fluoro-6-phenylamino-3H-benzoimidazole-5-carboxylic acid methyl ester 27a: 4-Amino-3-fluoro-5-nitro-2-phenylamino-benzoic acid methyl ester 26a (16.70 g, 54.71 mmol), formic acid (250 mL, 6.63 mol) and 20% Pd(OH)$_2$/C (9.00 g, 16.91 mmol) in ethanol (250 mL) are stirred at 40° C. for two hours under N$_2$ and then at 95° C. for 16 hours. The reaction mixture is cooled to room temperature and filtered through Celite rinsing with ethyl acetate. The filtrate is concentrated under reduced pressure to give a yellow solid. The solid is triturated with diethyl ether to give 13.47 g (86%) of the desired product as a tan solid. MS APCI (+) m/z 286 (M+1) detected; MS APCI (−) m/z 284 (M−1) detected.

Example 3

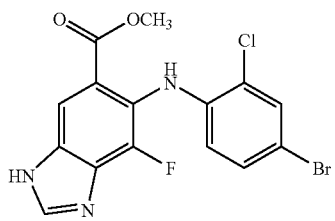

6-(4-Bromo-2-chloro-phenylamino)-7-fluoro-3H-benzoimidazole-5-carboxylic acid methyl ester (8b)

Step A: 6-(4-Bromo-phenylamino)-7-fluoro-3H-benzoimidazole-5-carboxylic acid methyl ester 28a: 7-Fluoro-6-phenylamino-3H-benzoimidazole-5-carboxylic acid methyl ester 27a (4.99 g, 17.51 mmol) is dissolved in N,N-dimethylformamide (275 mL). N-bromosuccinimide (3.15 g, 17.70 mmol) is added as a solid and the reaction mixture is stirred at room temperature under $N_2$. After 30 minutes, the reaction mixture is quenched by the addition of aqueous saturated sodium bisulfite solution. The reaction mixture is then poured into a reparatory funnel, diluted with water and ethyl acetate and the layers separated. The aqueous layer is extracted with ethyl acetate. The combined organic extracts are washed three times with water, once with brine and then are dried ($Na_2SO_4$) and concentrated under reduced pressure to yield 6.38 g (100%) of the pure desired product as a tan solid. MS ESI (+) m/z 364, 366 (M+ Br pattern) detected.

Step B: 6-(4-Bromo-2-chloro-phenylamino)-7-fluoro-3H-benzoimidazole-5-carboxylic acid methyl ester 8b: 6-(4-Bromo-phenylamino)-7-fluoro-3H-benzoimidazole-5-carboxylic acid methyl ester 28a (6.38 g, 17.51 mmol) is dissolved in N,N-dimethylformamide (275 mL). N-chlorosuccinimide (2.36 g, 17.70 mmol) is added as a solid and the reaction mixture is stirred at room temperature under $N_2$ until the reaction is complete (5-6 days). The reaction mixture is quenched by the addition of aqueous saturated sodium bisulfite solution to give a suspension. The resulting solids are collected by filtration, washed with water and diethyl ether and dried under reduced pressure to yield 6.07 g (87%) of the pure desired product as a beige solid. MS ESI (+) m/z 398, 400 (M+ Br pattern) detected.

Example 4

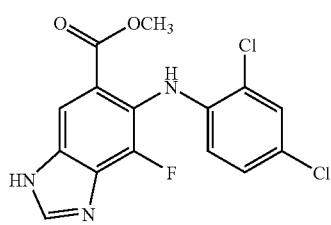

6-(2,4-Dichloro-phenylamino)-7-fluoro-3H-benzoimidazole-5-carboxylic acid methyl ester (8c)

7-Fluoro-6-phenylamino-3H-benzoimidazole-5-carboxylic acid methyl ester 27a (1.00 g, 3.51 mmol) is suspended in 1:1 tetrahydrofuran/methanol (20 mL) and cooled to −78° C. under $N_2$. TsOH.$H_2O$ (3.00 g, 10.50 mmol) is added followed by N-chlorosuccinimide (0.95 g, 7.08 mmol). After 10 minutes, the reaction mixture is warmed to 0° C. to give a solution and then 30 minutes later warmed to room temperature. After stirring for 16 hours, the reaction is complete. The reaction mixture is quenched by the addition of aqueous saturated sodium bisulfite solution and diluted with ethyl acetate and water and the layers separated. The aqueous layer is extracted with ethyl acetate. The combined organic extracts are washed with brine, dried ($Na_2SO_4$) and concentrated under reduced pressure. The resulting solid residue is triturated with methylene chloride to yield a white solid which is collected by filtration to yield 1.05 g (85%) of the pure desired product. MS ESI (+) m/z 355, 357 (M+ Cl pattern) detected.

Example 5

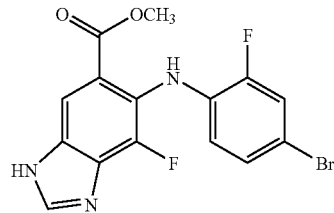

6-(4-Bromo-2-fluoro-phenylamino)-7-fluoro-3H-benzoimidazole-5-carboxylic acid methyl ester (8d)

Step A: 4-Amino-3-fluoro-2-(2-fluoro-phenylamino)-5-nitro-benzoic acid methyl ester 5b: 4-Amino-2,3-difluoro-5-nitro-benzoic acid methyl ester 4 (1.50 g, 6.46 mmol) is suspended in xylenes (7.5 mL) and 2-fluoro-phenylamine (6.24 mL, 64.6 mmol) is added. The reaction mixture is stirred at 140° C. under $N_2$. After stirring for 6 days, the reaction is complete. The reaction mixture is cooled to room temperature and diluted with methylene chloride and filtered through a silica gel plug eluting with methylene chloride (1L) to give an orange filtrate. The filtrate is concentrated to dryness and then triturated with diethyl ether to yield a bright yellow solid. The trituration is repeated. The yellow solid is collected to yield 1.08 g (52%) of the pure desired product. MS APCI (−) m/z 322 (M−1) detected.

Step B: 6-(4-Bromo-2-fluoro-phenylamino)-7-fluoro-3H-benzoimidazole-5-carboxylic acid methyl ester 8d: 4-Amino-3-fluoro-2-(2-fluoro-phenylamino)-5-nitro-benzoic acid methyl ester 5b is converted by the reduction/cyclization and bromination procedures already described to yield the desired product. MS ESI (+) m/z 382, 384 (M+, Br pattern) detected.

Example 6

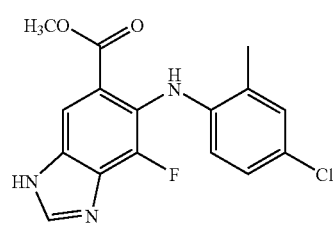

6-(4-Chloro-2-methyl-phenylamino)-7-fluoro-3H-benzoimidazole-5-carboxylic acid methyl ester (8e)

7-Fluoro-6-o-tolylamino-3H-benzoimidazole-5-carboxylic acid methyl ester 7a is converted by the procedure already described for bromination, except N-chlorosuccinimide is used instead of N-bromosuccinimide, to yield the desired product. MS ESI (+) m/z 334, 336 (M+, Cl pattern) detected.

Example 7

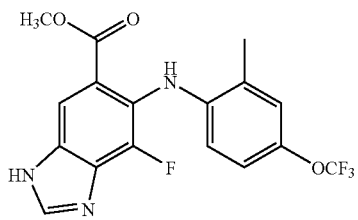

7-Fluoro-6-(2-methyl-4-trifluoromethoxy-phenylamino)-3H-benzoimidazole-5-carboxylic acid methyl ester (8f)

Step A. 4-Amino-3-fluoro-2-(2-methyl-4-trifluoromethoxy-phenylamino)-5-nitro-benzoic acid methyl ester 12a: 4-Amino-2,3-difluoro-5-nitro-benzoic acid methyl ester 4 (0.50 g, 2.15 mmol) is suspended in xylenes (3 mL) and 2-methyl-4-trifluoromethoxy-phenylamine (1.00 g, 5.23 mmol) is added. The reaction mixture is stirred at 140° C. under N$_2$. After stirring for 7 days, the reaction is a mixture of starting material and product. The reaction mixture is cooled to room temperature. The reaction mixture is poured into a reparatory funnel and diethyl ether and 10% aqueous HCl are added and the layers separated. The aqueous phase is extracted with three portions of diethyl ether. The combined diethyl ether layers are dried (MgSO$_4$) and concentrated under reduced pressure. The residue is redissolved in methylene chloride and flushed through a plug of silica gel eluting with methylene chloride. The filtrate is concentrated under reduced pressure to give a bright yellow solid. The solid is washed with diethyl ether and the filtrate is concentrated under reduced pressure and the residue is further purified by FCC (eluting with 100% methylene chloride) to yield 0.39 g (45%) of the desired pure product as a yellow solid. MS APCI (−) m/z 402 (M−1) detected.

Step B. 7-Fluoro-6-(2-methyl-4-trifluoromethoxy-phenylamino)-3H-benzoimidazole-5-carboxylic acid methyl ester 8f: 4-Amino-3-fluoro-2-(2-methyl-4-trifluoromethoxy-phenylamino)-5-nitro-benzoic acid methyl ester 12a is converted by the reduction/cyclization procedure already described to yield the desired product. MS APCI (+) m/z 384 (M+1) detected; MS APCI (−) m/z 382 (M−1) detected.

Example 8

Preparation of Hydroxylamines

Hydroxylamines useful for synthesizing compounds of the present invention may be prepared as follows
(i) O-(2-Methoxy-ethyl)-hydroxylamine
Step A: 2-(2-Methoxy-ethoxy)-isoindole-1,3-dione: DEAD (10 mL, 63 mmol) is added to a mixture of 2-methoxyethanol (5.0 mL, 63 mmol), PPh$_3$ (17 g, 63 mmol), and N-hydroxyphthalimide (10 g, 62 mmol) in THF (170 mL). The resulting orange solution is stirred 16 hours at room temperature. The reaction mixture is concentrated in vacuo, and the solids are filtered washing with CHCl$_3$. The filtrate is concentrated again, and the solids are filtered washing with CHCl$_3$. This process is repeated until no precipitate forms. The final yellowish solids are recrystallized from EtOH to give the desired product (7.7 g, 55%).

Step B: O-(2-Methoxy-ethyl)-hydroxylamine: To a solution of 2-(2-methoxy-ethoxy)-isoindole-1,3-dione (7.7 g, 35 mmol) in CH$_2$Cl$_2$ (30 mL) at room temperature is added methylhydrazine (2.0 mL, 36 mmol). The resulting solution is stirred for 16 hours at room temperature. The white solids are filtered off. The solvent is carefully distilled off under reduced pressure, and the concentrate is distilled under vacuum (20 ton, 57-58° C.) to afford the desired product (2.2 g, 68%).

(ii) The following hydroxylamines are prepared as described above using the appropriate alcohols. The isoindole-1,3-dione intermediates are purified by flash chromatography:

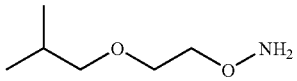

O-(2-Isobutoxy-ethyl)-hydroxylamine is used directly without purification.

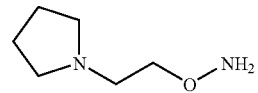

O-(2-Pyrrolidin-1-yl-ethyl)-hydroxylamine is used directly without purification.

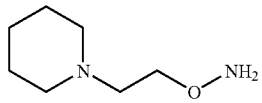

O-(2-Piperidin-1-yl-ethyl)-hydroxylamine is purified by Kugelrohr distillation (chamber temperature 140° C., 1 torr).

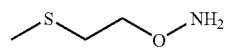

O-(2-Methylsulfanyl-ethyl)-hydroxylamine is purified by vacuum distillation (76-78° C., 20 ton).

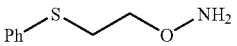

O-(2-Phenylsulfanyl-ethyl)-hydroxylamine is used directly without purification.

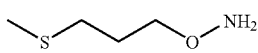

O-(3-Methylsulfanyl-propyl)-hydroxylamine is used directly without purification.

(iii) The following hydroxylamines are prepared from the appropriate isoindole-1,3-dione by oxidation using oxone (*Tetrahedron Lett.*, 1981, 22, 1287), and then deprotection as described above:

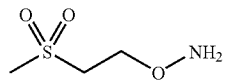

O-(2-Methanesulfonyl-ethyl)-hydroxylamine is used directly without purification.

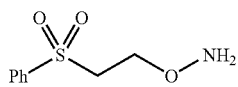

O-(2-Benzenesulfonyl-ethyl)-hydroxylamine is purified by flash chromatography (1% MeOH in $CH_2Cl_2$).

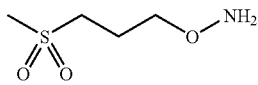

O-(3-Methanesulfonyl-propyl)-hydroxylamine is used directly without purification.

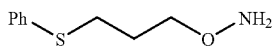

O-(3-Phenylsulfanyl-propyl)-hydroxylamine is prepared from $PhSCH_2CH_2CH_2Br$ and N-hydroxyphthalimide by the patent procedure WO 0018790 and then is deprotected by the procedure described above and used directly without purification.

(iv)

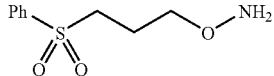

O-(3-Benzenesulfonyl-propyl)-hydroxylamine is prepared from the above isoindole-1,3-dione through its oxidation with oxone followed by deprotection as described above and is purified by flash chromatography (100% $CH_2Cl_2$ to 2% MeOH in $CH_2Cl_2$).

(v) O-(2-Morpholin-4-yl-ethyl)-hydroxylamine dihydrochloride

Step A: O-(2-Bromo-ethyl)-hydroxylamine hydrobromide: 2-(2-Bromo-ethoxy)-isoindole-1,3-dione is prepared from 1,2-dibromoethane and N-hydroxyphthalimide as described in WO 00/18790, and is then subjected to the procedure in *J. Org. Chem.*, 1963, 28, 1604 to yield the desired product.

Step B: (2-Bromo-ethoxy)-carbamic acid tert-butyl ester: To a solution of O-(2-bromo-ethyl)-hydroxylamine hydrobromide (100 mg, 0.45 mmol) and di-t-butyl dicarbonate (110 mg, 0.49 mmol) in $CH_2Cl_2$ (1 mL) at room temperature is added $Et_3N$ (0.08 mL, 0.56 mmol). The resulting suspension is stirred for 16 hours room temperature. The reaction mixture is diluted with EtOAc, washed with 1 N aqueous HCl and brine, dried over $MgSO_4$, filtered, concentrated, and purified by flash chromatography (100% $CH_2Cl_2$) to give the desired product (81 mg, 75%).

Step C: (2-Morpholin-4-yl-ethoxy)-carbamic acid tert-butyl ester: To a solution of (2-bromo-ethoxy)-carbamic acid tert-butyl ester (252 mg, 1.05 mmol) in DMF (2 mL) at room temperature is added morpholine (0.14 mL, 1.6 mmol). The reaction mixture is stirred for 7 hours at 50° C. The reaction mixture is diluted with EtOAc, and washed with water. The organic layer is dried over $MgSO_4$, filtered, concentrated, and purified by flash chromatography (2% MeOH in $CH_2Cl_2$) to give the desired product (118 mg, 46%): MS APCI (+) m/z 247 detected.

Step D: O-(2-Morpholin-4-yl-ethyl)-hydroxylamine dihydrochloride: To a solution of (2-morpholin-4-yl-ethoxy)-carbamic acid tert-butyl ester (118 mg, 0.48 mmol) in MeOH (1 mL) is added 4 M dioxane solution of HCl (2.4 mL, 9.60 mmol) at room temperature. The resulting solution is stirred for 16 hours at room temperature. After addition of additional HCl (2.4 mL) followed by stirring for 4 hours, the reaction mixture is concentrated in vacuo to give yellow solids (82 mg, 78%).

(vi) The isoindole-1,3-dione intermediates of the following hydroxylamines are prepared from the appropriate alkyl halide and N-hydroxyphthalimide by the procedure described within *J. Heterocyclic Chem.*, 2000, 37, 827-830. The isoindole-1,3-diones are deprotected by the procedure described above: O-but-3-enyl-hydroxylamine; O-(tetrahydro-furan-2-ylmethyl)-hydroxylamine; O-(3-methoxy-propyl)-hydroxylamine; and O-(3-benzyloxy-propyl)-hydroxylamine.

(vii) The following hydroxylamines are prepared as described in WO 02/06213: O-(2-vinyloxy-ethyl)-hydroxylamine; 2-aminooxy-2-methyl-propan-1-ol; 1-aminooxy-2-methyl-propan-2-ol; 3-aminooxy-propan-1-ol; and (2-aminooxy-ethyl)-methyl-carbamic acid tert-butyl ester.

Example 9

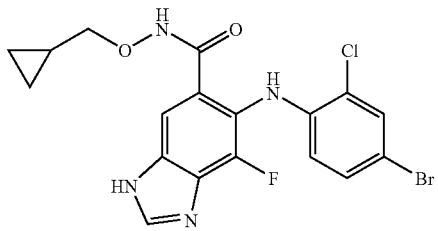

6-(4-Bromo-2-chloro-phenylamino)-7-fluoro-3H-benzoimidazole-5-carboxylic acid cyclopropyl-methoxy-amide (11b)

Step A: 4-Amino-2-(2-chloro-phenylamino)-3-fluoro-5-nitro-benzoic acid methyl ester 5b: 4-Amino-2,3-difluoro-5-nitro-benzoic acid methyl ester 4 (2.00 g, 8.62 mmol) is suspended in xylenes (15 mL) and 2-chloro aniline (9.06 mL, 86.15 mmol) is added. The reaction mixture is heated to 140°

C. under a nitrogen atmosphere. After 6 days, the reaction mixture is cooled to room temperature, and diluted with ethyl acetate. The reaction mixture is washed with water, 10% HCl solution and brine. The organic layer is dried (MgSO$_4$) and concentrated under reduced pressure. The crude product is triturated with diethyl ether, twice, to give 0.35 g (12%) pure desired product as a brownish solid.

Step B: 4,5-Diamino-2-(2-chloro-phenylamino)-3-fluoro-benzoic acid methyl ester 6a: 4-Amino-2-(2-chloro-phenylamino)-3-fluoro-5-nitro-benzoic acid methyl ester 5b (0.30 g, 0.88 mmol) is suspended in AcOH (5 mL) and zinc dust (0.29 g, 4.42 mmol) is added. After 15 minutes, the reaction is complete. The reaction mixture is diluted with ethyl acetate and filtered through Celite. The filtrate is washed with water, saturated NaHCO$_3$, 10% K$_2$CO$_3$ and brine. The organic layer is dried (MgSO$_4$) and concentrated under reduced pressure to give 0.13 g (48%) pure desired product as a whitish brown foam.

Step C: 6-(2-Chloro-phenylamino)-7-fluoro-3H-benzoimidazole-5-carboxylic acid methyl ester 7b: 4,5-Diamino-2-(2-chloro-phenylamino)-3-fluoro-benzoic acid methyl ester 6a (0.125 g, 0.404 mmol) is suspended in EtOH (2 mL) and formamidine acetate (63 mg, 0.605 mmol) is added. The reaction mixture is heated to reflux. After 16 hours, the reaction mixture is cooled to room temperature and diluted with ethyl acetate. The organic layer is washed with water, saturated NaHCO$_3$, 10% K$_2$CO$_3$ and brine. The organic layer is dried (MgSO$_4$) and concentrated under reduced pressure to give 0.109 g (85%) pure desired product.

Step D: 6-(4-Bromo-2-chloro-phenylamino)-7-fluoro-3H-benzoimidazole-5-carboxylic acid methyl ester 8b: 6-(2-Chloro-phenylamino)-7-fluoro-3H-benzoimidazole-5-carboxylic acid methyl ester 7b (55 mg, 0.172 mmol) is dissolved in 1:1 THF/MeOH (2 mL) and cooled to −78° C. under an atmosphere of nitrogen. TsOH.H$_2$O (49 mg, 0.258 mmol) is added followed by NBS (31 mg, 0.174 mmol). After 10 minutes, the reaction mixture is warmed to 0° C. and then 2 hours later warmed to room temperature. After 16 hours, the reaction mixture is quenched by the addition of 10% Na$_2$S$_2$O$_3$ and diluted with ethyl acetate and water. The layers are separated and the aqueous layer is extracted with ethyl acetate. The combined organic extracts are dried (MgSO$_4$) and concentrated under reduced pressure. The crude product is triturated with methylene chloride to give 58 mg (85%) of pure desired product as a tan solid.

Step E: 6-(4-Bromo-2-chloro-phenylamino)-7-fluoro-3H-benzoimidazole-5-carboxylic acid 10b: 6-(4-Bromo-2-chloro-phenylamino)-7-fluoro-3H-benzoimidazole-5-carboxylic acid methyl ester 8b (58 mg, 0.146 mmol) is suspended in EtOH (2 mL) and 1 mL 2 N NaOH is added. After 16 hours, the reaction mixture is diluted with ethyl acetate, water, and 10% HCl solution. The layers are separated and the organic layer is washed with brine. The organic layer is dried (MgSO$_4$) and concentrated under reduced pressure. Trituration with MeOH provides 22 mg (39%) pure desired product.

Step F: 6-(4-Bromo-2-chloro-phenylamino)-7-fluoro-3H-benzoimidazole-5-carboxylic acid cyclopropylmethoxy-amide (11b): 6-(4-Bromo-2-chloro-phenylamino)-7-fluoro-3H-benzoimidazole-5-carboxylic acid 10b (22 mg, 0.057 mmol) is dissolved in DMF (1 mL) and HOBt (9 mg, 0.062 mmol) followed by triethyl amine (18 μL, 0.132 mmol) is added. Cyclopropyl methyl hydroxylamine hydrochloride (8 mg, 0.062 mmol) is added followed by EDCI (14 mg, 0.074 mmol). After 16 hours, the reaction mixture is diluted with ethyl acetate and water and the layers separated. The organic layer is washed with saturated NH$_4$Cl, brine, saturated NaHCO$_3$, water and brine. The organic layer is dried (MgSO$_4$) and concentrated under reduced pressure to give 23 mg (89%) pure desired product. MS APCI (+) m/z 455, 453 (M+ Br pattern) detected; MS APCI (−) m/z 453, 451 (M− Br pattern) detected; $^1$H NMR (400 MHz, DMSO-d$_6$) δ 11.69 (broad s, 1H), 8.43 (s, 1H), 7.62 (d, 1H), 7.28 (dd, 1H), 6.42 (m, 1H), 3.63 (d, 2H), 1.03 (m, 1H), 0.48 (m, 2H), 0.19 (m, 2H); $^{19}$F NMR (376 MHz, DMSO-d$_6$) −132.95 (s).

The following compounds are prepared by methods similar to those described in Example 1 and in this Example 9 by using the appropriate carboxylic acid and the appropriate hydroxylamine:

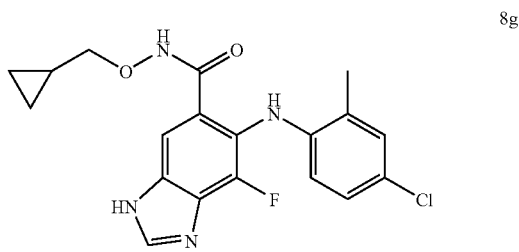

8g

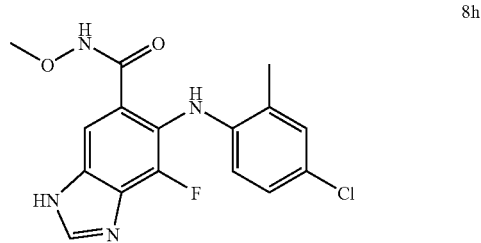

8h

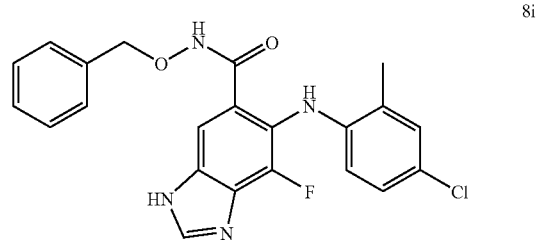

8i

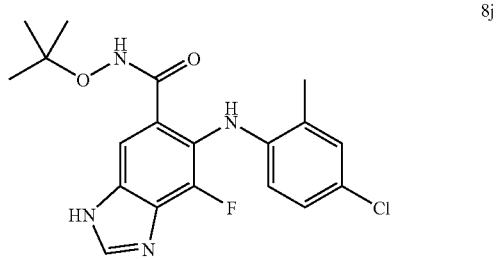

8j

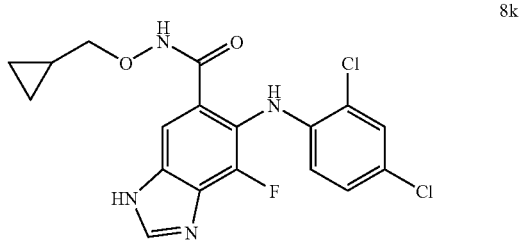

8k

-continued

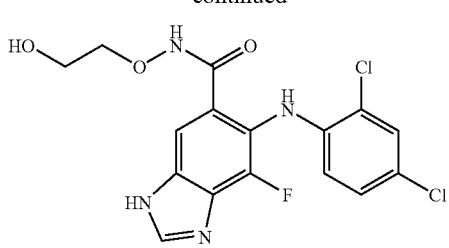

81

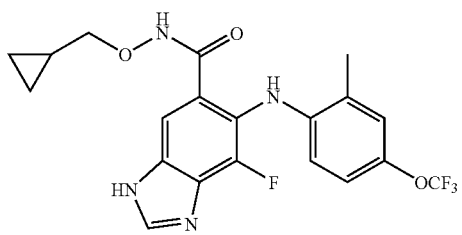

8m

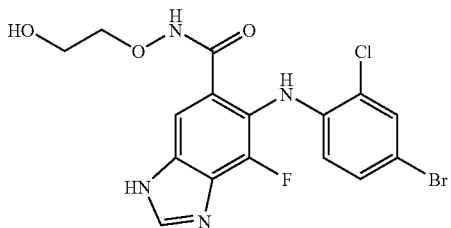

8n

Example 10

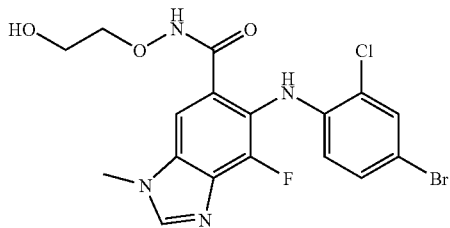

6-(4-Bromo-2-chloro-phenylamino)-7-fluoro-3-methyl-3H-benzoimidazole-5-carboxylic acid (2-hydroxy-ethoxy)-amide (29c)

Step A: 6-(4-Bromo-2-chloro-phenylamino)-7-fluoro-3-methyl-3H-benzoimidazole-5-carboxylic acid methyl ester 9a and 6-(4-Bromo-2-chloro-phenylamino)-7-fluoro-1-methyl-1H-benzoimidazole-5-carboxylic acid methyl ester: A solution of 6-(4-bromo-2-chloro-phenylamino)-7-fluoro-3H-benzoimidazole-5-carboxylic acid methyl ester 8b (150 mg, 0.38 mmol), iodomethane (28 µL, 0.45 mmol) and potassium carbonate (78 mg, 0.56 mmol) in dimethylformamide (1.5 mL) is stirred at 75° C. for one hour. The reaction mixture is diluted with ethyl acetate, washed with saturated aqueous potassium carbonate (2x), brine, and dried (Na$_2$SO$_4$). Flash column chromatography (20:1 methylene chloride/ethyl acetate) provides 56 mg (36%) of the more mobile 6-(4-bromo-2-chloro-phenylamino)-7-fluoro-3-methyl-3H-benzoimidazole-5-carboxylic acid methyl ester 9a as a white solid. $^{19}$F NMR (376 MHz, CD$_3$OD) −133.5 (s). MS APCI (+) m/z 412, 414 (M+, Br pattern) detected. Also isolated is 54 mg (35%) of 6-(4-bromo-2-chloro-phenylamino)-7-fluoro-1-methyl-1H-benzoimidazole-5-carboxylic acid methyl ester as a white solid. $^{19}$F NMR (376 MHz, CD$_3$OD) −139.9 (s). MS APCI (+) m/z 412, 414 (M+, Br pattern) detected.

Step B: 6-(4-Bromo-2-chloro-phenylamino)-7-fluoro-3-methyl-3H-benzoimidazole-5-carboxylic acid 10c: 6-(4-Bromo-2-chloro-phenylamino)-7-fluoro-3-methyl-3H-benzoimidazole-5-carboxylic acid methyl ester 9a (56 mg, 0.14 mmol) is dissolved into 2:1 THF/water (3 mL) and NaOH (0.55 mL, 1.0 M aqueous solution, 0.55 mmol) is added. After stirring for two hours the reaction is reduced to one-quarter initial volume via rotary evaporation and the remainder diluted to 50 mL with water. The aqueous solution is acidified to pH 2 by the addition of 1.0 M aqueous HCl and extracted with 1:1 tetrahydrofuran/ethyl acetate (3x), dried (Na$_2$SO$_4$) and concentrated under reduced pressure to provide 43 mg (79%) pure carboxylic acid as an off white solid. MS ESI (+) m/z 397, 398 (M+, Br pattern) detected.

Step C: 6-(4-Bromo-2-chloro-phenylamino)-7-fluoro-3-methyl-3H-benzoimidazole-5-carboxylic acid (2-vinyloxy-ethoxy)-amide 29a: 6-(4-Bromo-2-chloro-phenylamino)-7-fluoro-3-methyl-3H-benzoimidazole-5-carboxylic acid 10c (2.00 g, 5.0 mmol), O-(2-vinyloxy-ethyl)-hydroxylamine (0.776 g, 7.5 mmol), HOBt (0.88 g, 6.5 mmol), triethylamine (1.61 mL, 2.3 mmol) and EDCI (1.3 g, 6.5 mmol) are dissolved in dimethylformamide (52 mL) and stirred at room temperature for 48 hours. The reaction mixture is diluted with ethyl acetate, washed with water (3x), saturated potassium carbonate (2x), saturated ammonium chloride (2x), brine, dried (Na$_2$SO$_4$) and concentrated under reduced pressure to an off-white solid. Trituration of the solid with diethyl ether provides 2.18 g (90%) desired product as an off-white solid. MS ESI (+) m/z 483, 485 (M+ Br pattern) detected.

Step D: 6-(4-Bromo-2-chloro-phenylamino)-7-fluoro-3-methyl-3H-benzoimidazole-5-carboxylic acid (2-hydroxy-ethoxy)-amide 29c: Hydrochloric acid (14 mL, 1.0 M aqueous solution, 14 mmol) is added to a suspension of 6-(4-bromo-2-chloro-phenylamino)-7-fluoro-3-methyl-3H-benzoimidazole-5-carboxylic acid (2-vinyloxy-ethoxy)-amide 29a (2.18 g, 4.50 mmol) in ethanol (50 mL) and the reaction mixture allowed to stir for 24 hours. The reaction mixture is concentrated to dryness by rotary evaporation and the solids partitioned between 3:1 ethyl acetate/tetrahydrofuran and saturated potassium carbonate. The aqueous phase is extracted with 3:1 ethyl acetate/tetrahydrofuran (3x), the combined organics dried (Na$_2$SO$_4$), and concentrated to provide 2.11 g (100%) 6-(4-bromo-2-chloro-phenylamino)-7-fluoro-3-methyl-3H-benzoimidazole-5-carboxylic acid (2-hydroxy-ethoxy)-amide as an off-white solid. MS ESI (+) m/z 457, 459 (M+, Br pattern) detected. $^1$H NMR (400 MHz, MeOH-d$_4$) δ 8.26 (s, 1H), 7.78 (s, 1H), 7.57 (d, 1H), 7.24 (dd, 1H), 6.40 (dd, 1H), 3.86 (s, 3H), 3.79 (m, 2H), 3.49 (m, 2H). $^{19}$F NMR (376 MHz, MeOH-d$_4$) −133.68 (s).

Example 11

The following compounds are prepared by methods similar to those described in Example 10 by using methyl ester 8b and the appropriate alkylating agent (Step A) and the appropriate hydroxylamine (Step C):

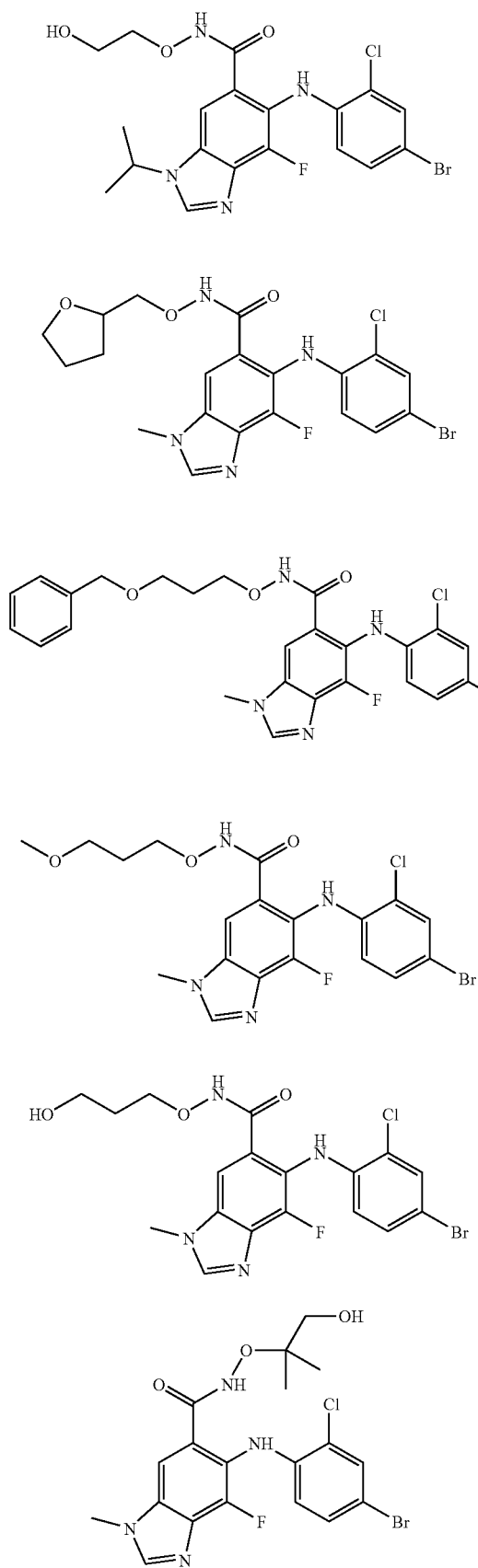

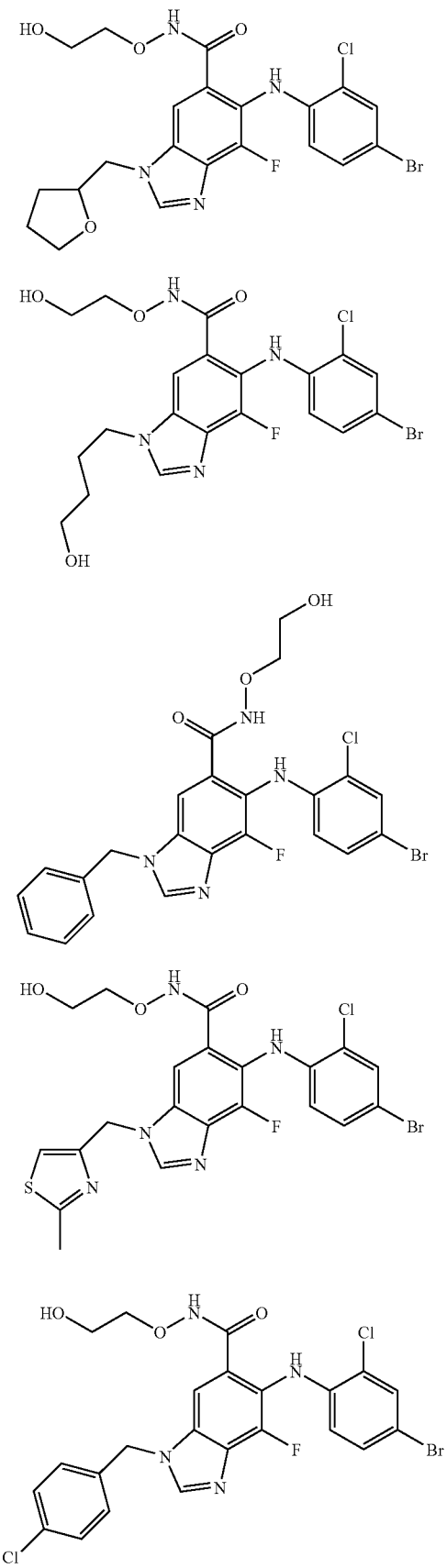

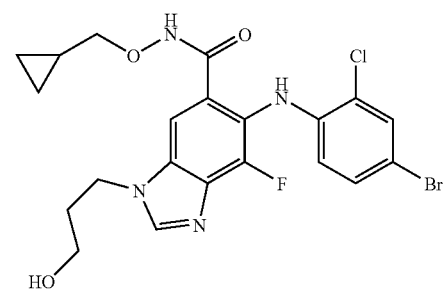
29z
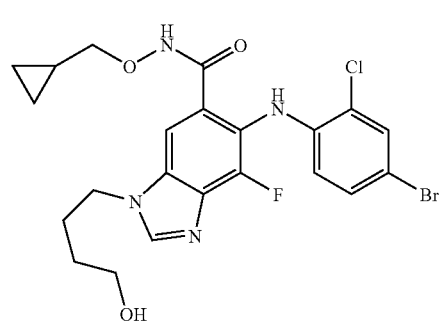
29aa
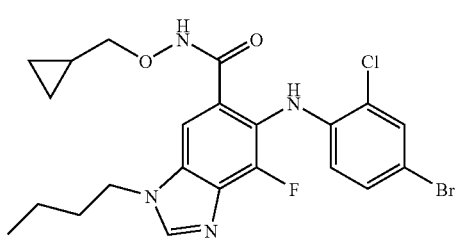
29bb
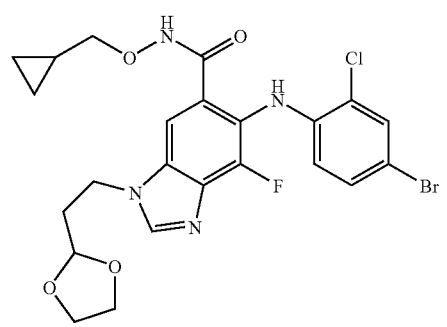
29cc
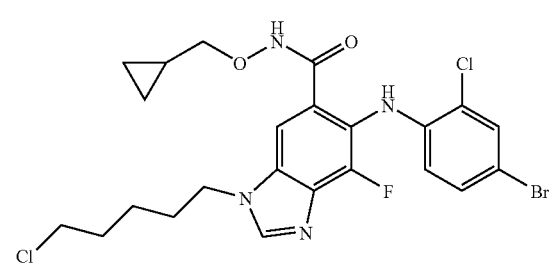
29dd
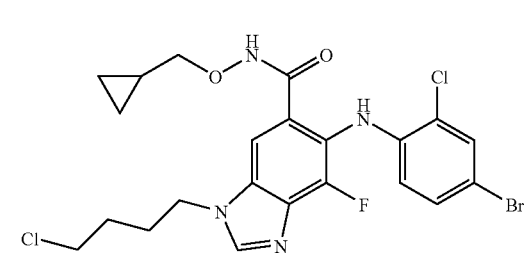
29ee
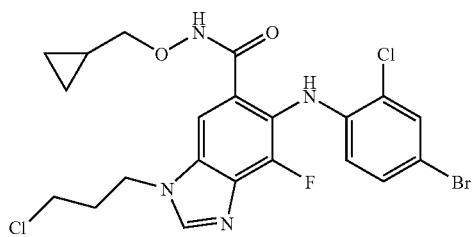
29ff
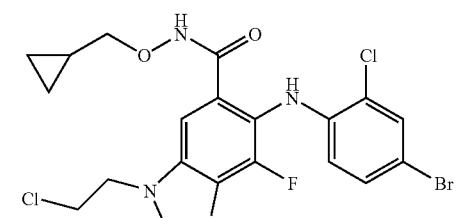
29gg
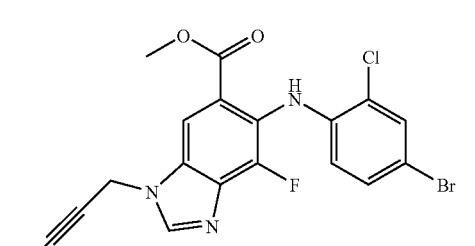
29hh
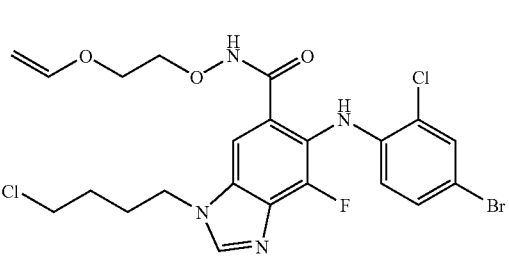
29ii
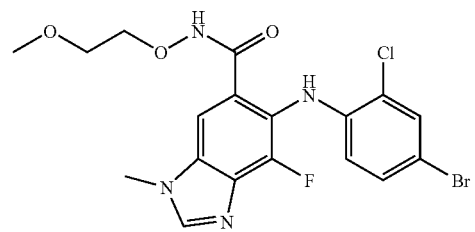
29jj 29kk
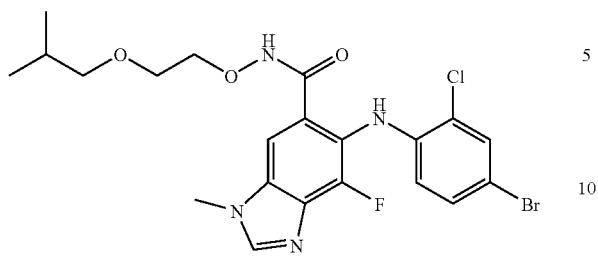
29ll
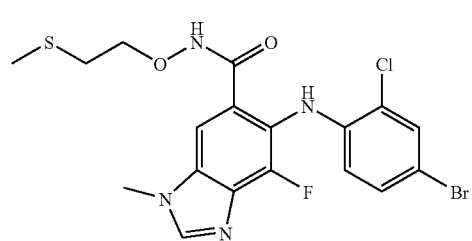
29mm
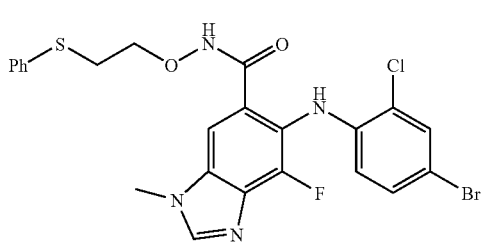
29nn
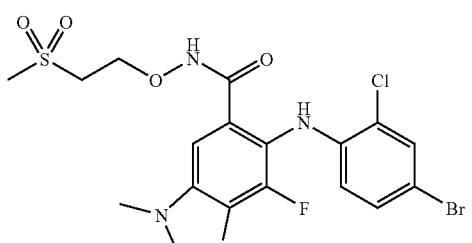
29oo
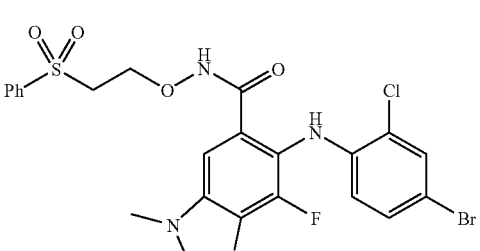
29pp
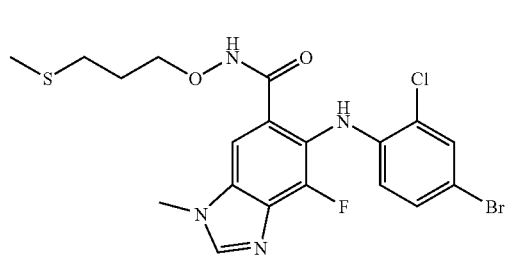
29qq
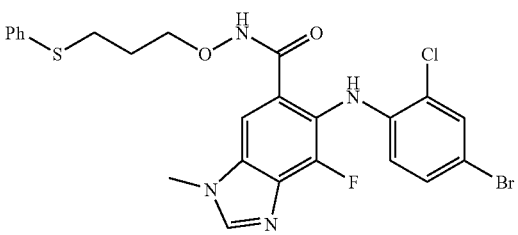
29rr
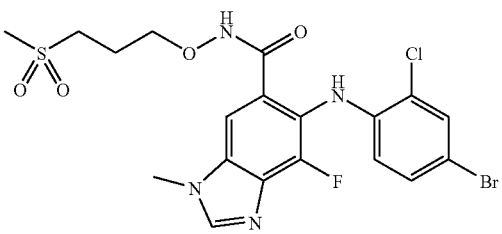
29ss
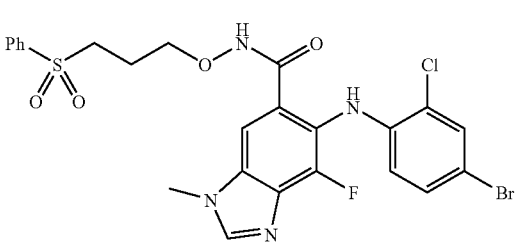
29tt
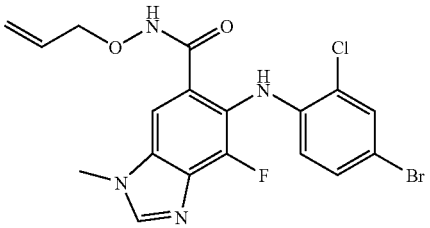
29uu
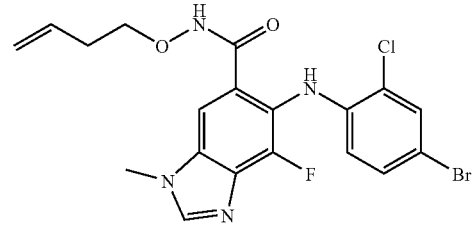
29vv
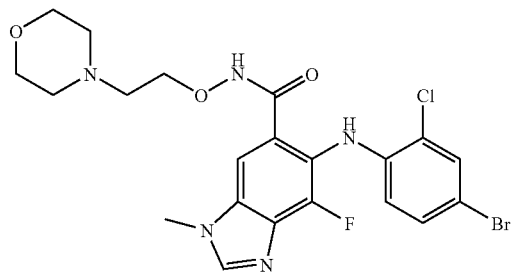

29ww
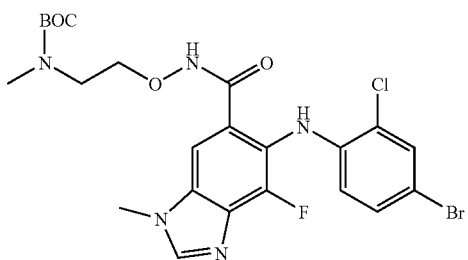
29ccc
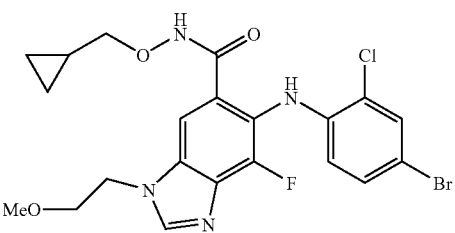
29xx
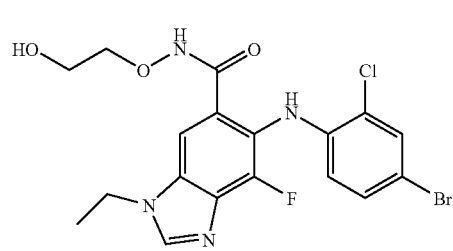
29ddd
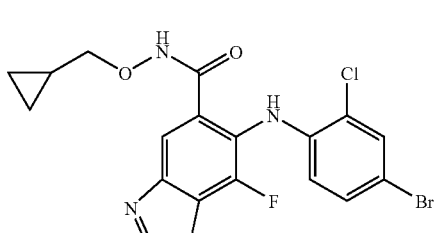
29yy
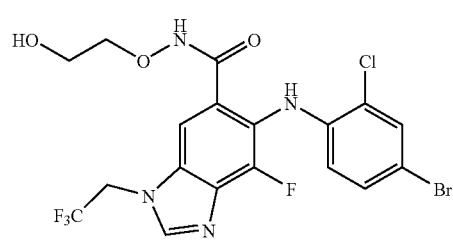
29eee
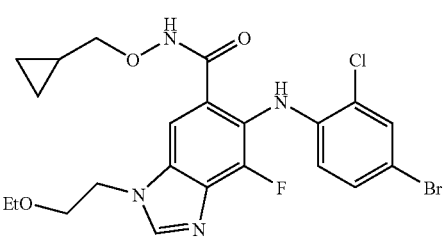
29zz
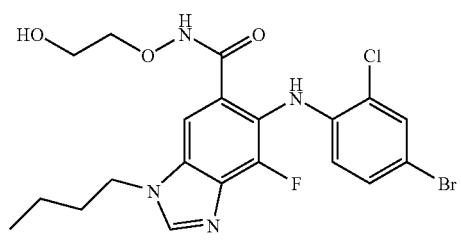
29fff
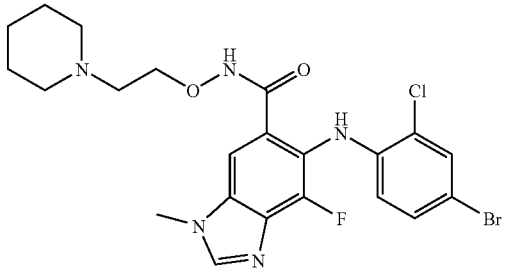
29aaa
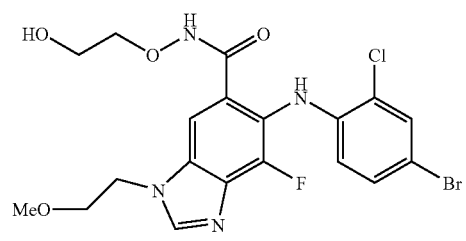
29ggg
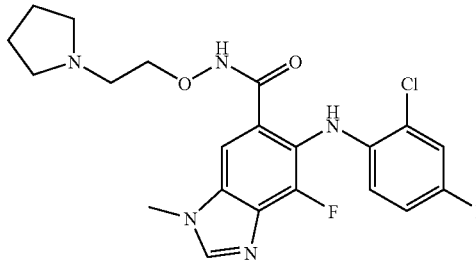
29bbb
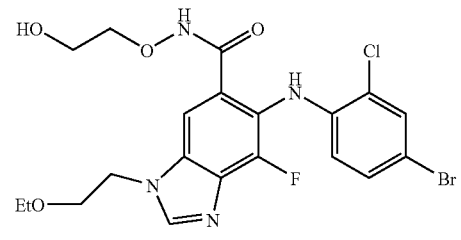

Example 12

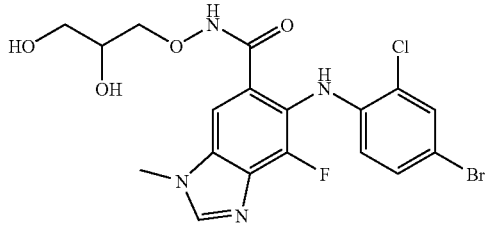

6-(4-Bromo-2-chloro-phenylamino)-7-fluoro-3-methyl-3H-benzoimidazole-5-carboxylic acid (2,3-dihydroxy-propoxy)-amide (29hhh)

To a solution of 6-(4-bromo-2-chloro-phenylamino)-7-fluoro-3-methyl-3H-benzoimidazole-5-carboxylic acid allyloxy-amide 29tt (20 mg, 0.04 mmol) in 0.50 mL 4:1 tetrahydrofuran/water is added $OsO_4$ (41 µL, 0.054 M solution in t-BuOH, 0.002 mmol) followed by NMO (7 mg, 0.06 mmol). The solution is stirred at room temperature for eight hours after which time HPLC analysis showed complete conversion to product. The solution is then stirred with saturated $NaHSO_3$ and diluted with ethyl acetate. The organic phase is dried ($Na_2SO_4$). Purification by FCC (DCM->20:1 DCM/MeOH) provided 16 mg desired product as an off-white solid. MS ESI (+) m/z 487, 489 (M+, Br pattern) detected.

Example 13

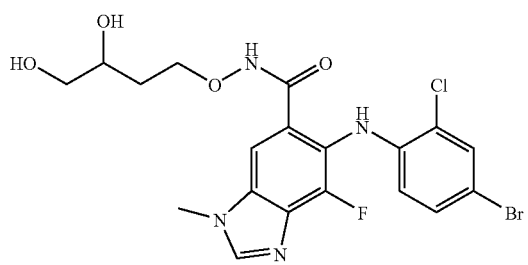

6-(4-Bromo-2-chloro-phenylamino)-7-fluoro-3-methyl-3H-benzoimidazole-5-carboxylic acid (3,4-dihydroxy-butoxy)-amide (29iii)

6-(4-bromo-2-chloro-phenylamino)-7-fluoro-3-methyl-3H-benzoimidazole-5-carboxylic acid but-3-enyloxy-amide 29uu is subjected to the dihydroxylation method described in Example 12. MS APCI (+) m/z 501, 503 (M+ Br pattern) detected.

Example 14

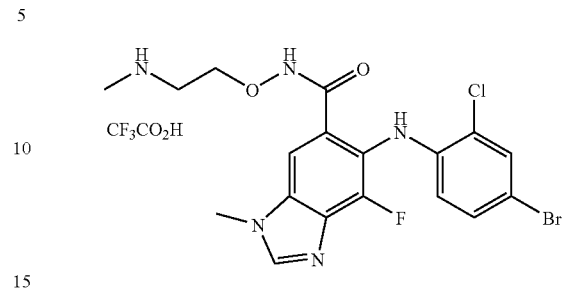

6-(4-Bromo-2-chloro-phenylamino)-7-fluoro-3-methyl-3H-benzoimidazole-5-carboxylic acid (2-methylamino-ethoxy)-amide TFA salt (29jjj)

Prepared from (2-{[6-(4-bromo-2-chloro-phenylamino)-7-fluoro-3-methyl-3H-benzoimidazole-5-carbonyl]-aminooxy}-ethyl)-methyl-carbamic acid tert-butyl ester 29ww by trifluoroacetic acid deprotection in methylene chloride. MS APCI (+) m/z 470, 472 (M+, Br pattern) detected; $^1$H NMR (400 MHz, $CD_3OD$) δ 8.31 (s, 1H), 7.74 (s, 1H), 7.51 (d, 1H), 7.19 (dd, 1H), 6.39 (dd, 1H), 4.11 (m, 2H), 3.97 (s, 3H), 3.12 (m, 2H), 2.72 (s, 3H); $^{19}$F NMR (376 MHz, $CD_3OD$) −77.41 (s, 3F), −134.79 (s, 1F).

Example 15

The following compounds are prepared by methods similar to those described in Example 10 by using methyl ester 8a and the appropriate alkylating agent (Step A) and the appropriate hydroxylamine (Step C):

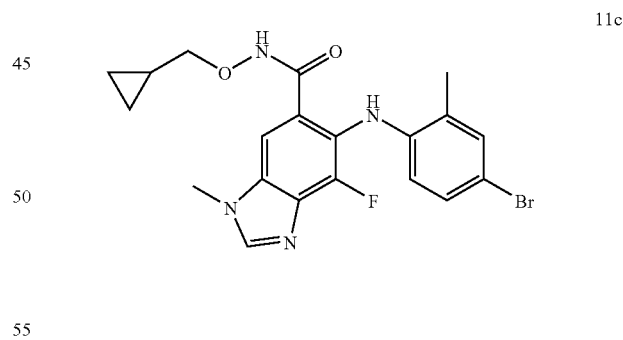

11c

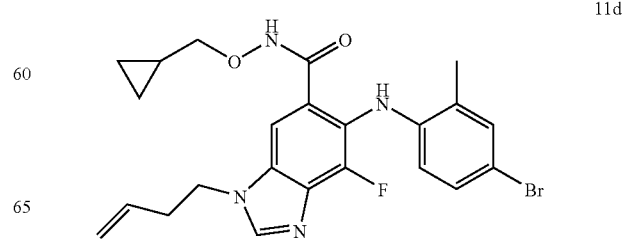

11d

11e
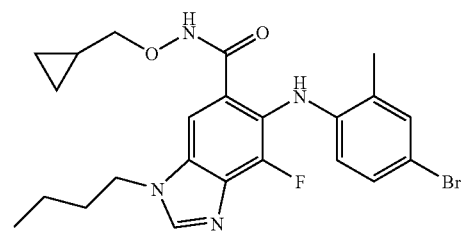

11f
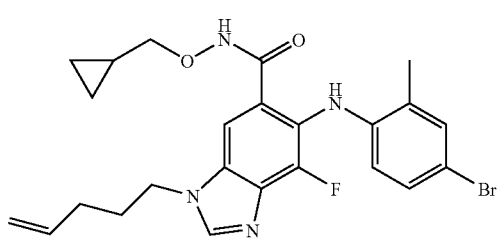

Example 16

The following compounds are prepared by methods similar to those described in Example 10 by using methyl ester 8e and the appropriate alkylating agent (Step A) and the appropriate hydroxylamine (Step C):

11g
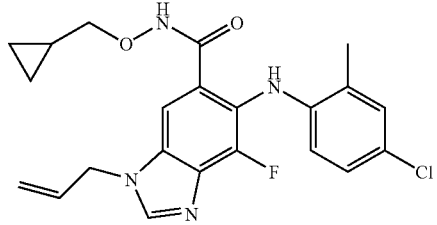

11h
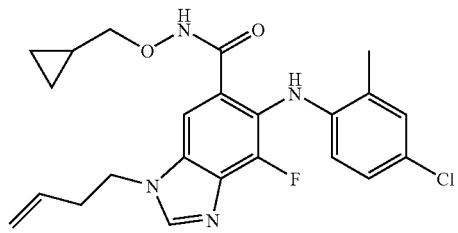

11i
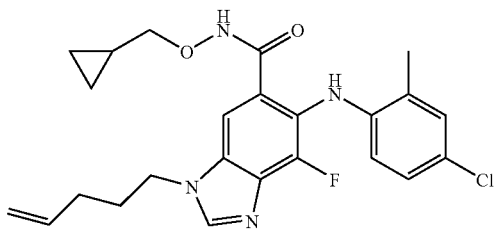

11j
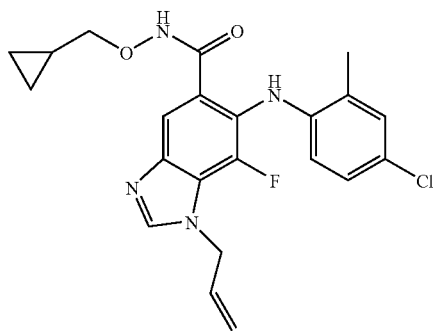

11k
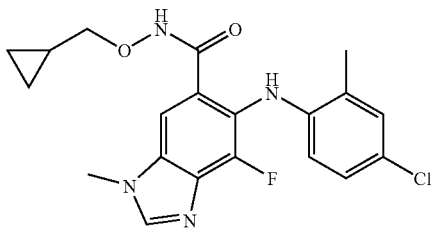

11l
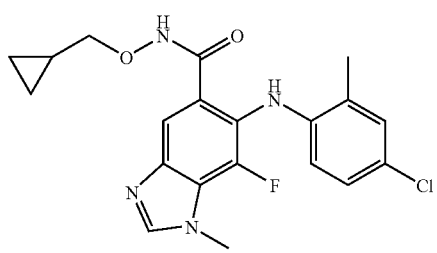

Example 17

The following compounds are prepared by methods similar to those described in Example 10 by using methyl ester 8c and the appropriate alkylating agent (Step A) and the appropriate hydroxylamine (Step C):

11m
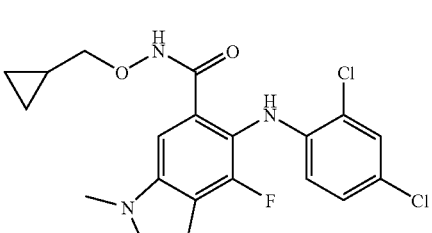

29kkk
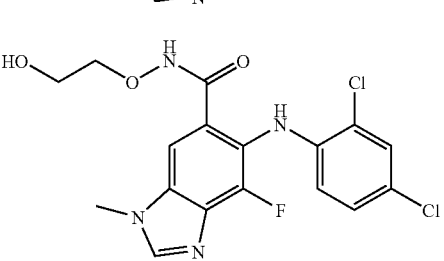

Example 18

The following compounds are prepared by methods similar to those described in Example 10 by using methyl ester 8d and the appropriate alkylating agent (Step A) and the appropriate hydroxylamine (Step C):

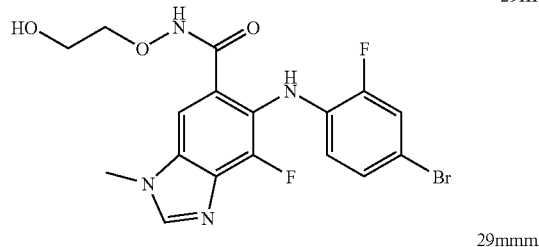

29III

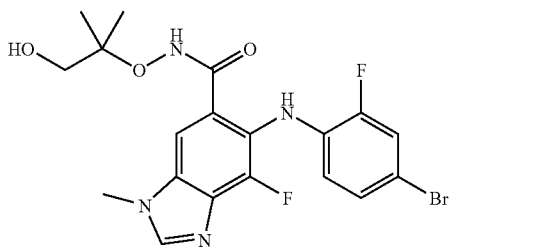

29mmm

Example 19

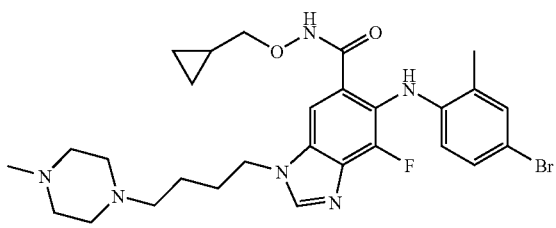

6-(4-Bromo-2-methyl-phenylamino)-7-fluoro-3-[4-(4-methyl-piperazin-1-yl)-butyl]-3H-benzoimidazole-5-carboxylic acid cyclopropylmethoxy-amide (11o)

Step A: 6-(4-Bromo-2-methyl-phenylamino)-7-fluoro-3-pent-4-enyl-3H-benzoimidazole-5-carboxylic acid methyl ester 9b: 7-Fluoro-6-(4-bromo-2-methyl-phenylamino)-1H-benzoimidazole-5-carboxylic acid methyl ester 8a (0.915 g, 2.419 mmol) is suspended in DMF (18 mL) under an atmosphere of nitrogen. Bromopentene (0.430 mL, 3.629 mmol) and $K_2CO_3$ (0.502 g, 3.629 mmol) are added and the reaction mixture was warmed to 80° C. After 1 hour, the reaction mixture is cooled to room temperature and poured into 100 mL of 1:1 ethyl acetate/diethyl ether. The organic layer is washed with water and brine, dried ($Na_2SO_4$) and concentrated under reduced pressure. The N3 and N1 alkylated products are separated by flash column chromatography, eluted with 20:1 methylene chloride/ethyl acetate. Complete separation of the isomers is obtained by performing two chromatographic separations. The higher $R_f$ product is the N3 product 9b, while the lower $R_f$ product is the N1 product. The recovery of the N3 product 9b is 0.415 g (38%): LC/MS ESI (+) m/z 448, 446 (M+1 Br pattern) detected. The recovery of the N1 product was 0.486 g (45%): LC/MS ESI (+) m/z 448, 446 (M+1 Br pattern) detected.

Step B: 6-(4-Bromo-2-methyl-phenylamino)-7-fluoro-3-pent-4-enyl-3H-benzoimidazole-5-carboxylic acid 10d: 6-(4-Bromo-2-methyl-phenylamino)-7-fluoro-3-pent-4-enyl-3H-benzoimidazole-5-carboxylic acid methyl ester 9b is dissolved in 1:1 THF/MeOH (10 mL) and 1 N NaOH solution (2.3 mL) is added. After 5 hours, the organic solvents are removed under reduced pressure and the residue diluted with water and 100 mL 1:1 THF:ethyl acetate. The layers are separated and the aqueous layer extracted with ethyl acetate. The combined organic extracts are dried ($Na_2SO_4$) and concentrated under reduced pressure to afford 0.39 g (100%) clean desired product as a light yellow solid.

Step C: 6-(4-Bromo-2-methyl-phenylamino)-7-fluoro-3-pent-4-enyl-3H-benzoimidazole-5-carboxylic acid cyclopropylmethoxy-amide 11f: 6-(4-Bromo-2-methyl-phenylamino)-7-fluoro-3-pent-4-enyl-3H-benzoimidazole-5-carboxylic acid 10d (0.390 g, 0.902 mmol) is dissolved in 1:1 THF/methylene chloride (6 mL) and Hunig's base (0.346 mL, 1.985 mmol) is added followed by PyBOP (0.563 g, 1.083 mmol). After 10 minutes, cyclopropyl methyl hydroxylamine hydrochloride (0.134 g, 1.083 mmol) is added. After 16 hours, the reaction mixture is diluted with ethyl acetate and washed with 0.1 N HCl, saturated $NaHCO_3$, and brine. The organic layer is dried ($Na_2SO_4$) and concentrated under reduced pressure. The crude yellow residue is purified by FCC eluted with ethyl acetate to give 0.315 g (70%) pure desired product as a yellow solid: MS APCI (+) m/z 503, 501 (M+1 Br pattern) detected.

Step D: 6-(4-Bromo-2-methyl-phenylamino)-3-(4,5-dihydroxy-pentyl)-7-fluoro-3H-benzoimidazole-5-carboxylic acid cyclopropylmethoxy-amide 11m: 6-(4-Bromo-2-methyl-phenylamino)-7-fluoro-3-pent-4-enyl-3H-benzoimidazole-5-carboxylic acid cyclopropylmethoxy-amide 11f (0.307 g, 0.612 mmol) is dissolved in 4:1 THF/water (8 mL) and 1.134 mL (0.061 mmol) of an 0.054 M $OsO_4$ solution in t-BuOH iias added followed by NMO (0.093 g, 0.796 mmol). After 5 hours, the reaction mixture is quenched by the addition of 10% $NaHS_2O_3$ solution. After 10 minutes, the reaction mixture is filtered through Celite rinsing with ethyl acetate and methylene chloride. The filtrate is diluted with ethyl acetate and washed with 0.01 N HCl, and brine. The organic layer is dried ($Na_2SO_4$) and concentrated under reduced pressure. The crude product is purified by FCC eluted with 9:1 ethyl acetate/MeOH to give 0.244 g (74%) pure desired product.

Step E: 6-(4-Bromo-2-methyl-phenylamino)-7-fluoro-3-(4-oxo-butyl)-3H benzoimidazole-5-carboxylic acid cyclopropylmethoxy-amide 11n: To a mixture of 6-(4-bromo-2-methyl-phenylamino)-3-(4,5-dihydroxy-pentyl)-7-fluoro-3H-benzoimidazole-5-carboxylic acid cyclopropylmethoxy-amide 11m (0.244 g, 0.456 mmol), THF (5 mL) and pH 7 phosphate buffer (3 mL) is added sodium periodate (0.195 g, 0.911 mmol). After 16 hours, the reaction mixture is diluted with ethyl acetate and washed with $NaHCO_3$, and brine. The organic layer is dried ($Na_2SO_4$) and concentrated under reduced pressure to give an orange solid. Purification by FCC eluted with 4:1 methylene chloride/MeOH yields 0.189 g (82%) pure desired product as a yellow solid: MS APCI (+) m/z 505, 503 (M+1 Br pattern) detected; MS APCI (−) m/z 503, 501 (M−1 Br pattern) detected.

Step F: 6-(4-Bromo-2-methyl-phenylamino)-7-fluoro-3-[4-(4-methyl-piperazin-1-yl)-butyl]-3H-benzoimidazole-5-carboxylic acid cyclopropylmethoxy-amide 11o: 6-(4-

Bromo-2-methyl-phenylamino)-7-fluoro-3-(4-oxo-butyl)-3H benzoimidazole-5-carboxylic acid cyclopropylmethoxy-amide 11n (15 mg, 0.030 mmol) is dissolved in MeCN (500 µL) and methylpiperazine (10 µl, 0.089 mmol) is added followed by AcOH (5 µL, 0.089 mmol). After 5 minutes, tetramethylammonium triacetoxyborohydride (12 mg, 0.045 mmol) is added. After 5 minutes, the reaction mixture is diluted with ethyl acetate and washed with NaHCO$_3$ and brine. The organic layer is dried (Na$_2$SO$_4$) and concentrated under reduced pressure to give 12 mg (69%) of pure desired product as a white solid. MS APCI (−) m/z 587, 585 (M−1 Br pattern) detected; $^1$H NMR (400 MHz, CDCl$_3$) δ 7.99 (s, 1H), 7.98 (s, 1H), 7.30 (d, 1H), 7.08 (dd, 1H), 6.30 (d, 1H), 6.1 (broad singlet, 1H), 4.26 (t, 2H), 3.64 (d, 2H), 3.37 (s, 1H), 2.45 (broad, 8H), 2.41 (s, 3H), 2.38 (t, 2H), 2.28 (s, 3H), 1.95 (quin, 2H), 1.55 (quin, 2H), 0.98 (m, 1H), 0.50 (qt, 2H), 0.22 (qt, 2H).

Example 20

The following compounds are prepared by methods similar to those described in Example 19 by using the appropriate alkenyl substituted benzimidazole and the appropriate amine in the reductive amination (step F):

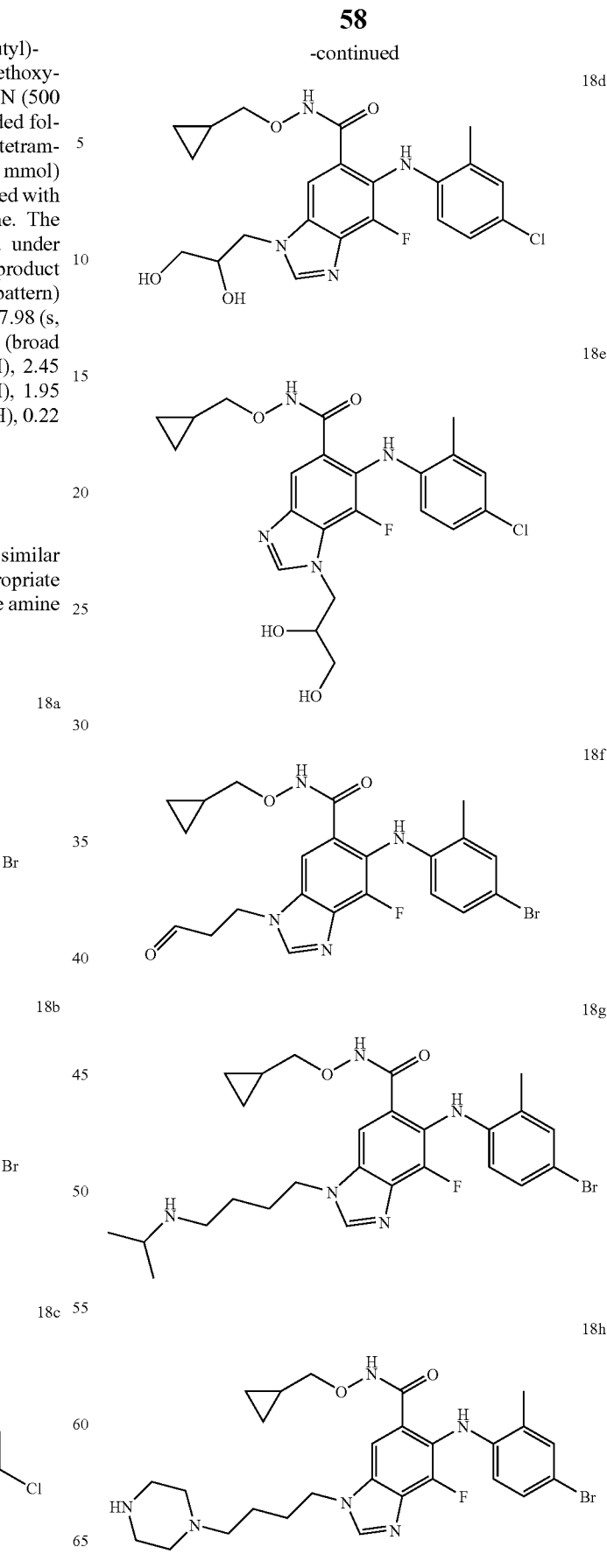

18i
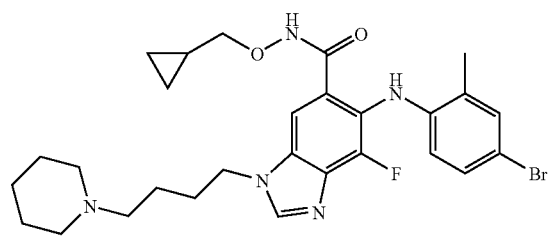
18j
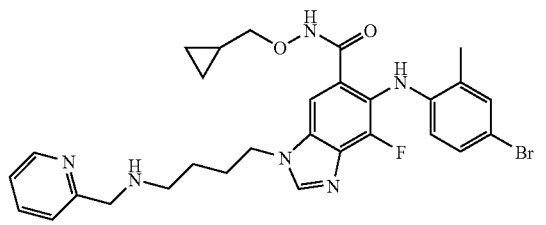
18k
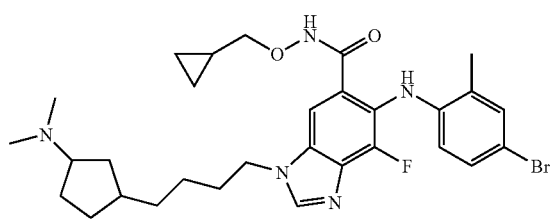
18l
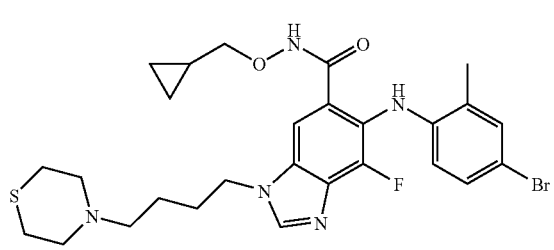
18m
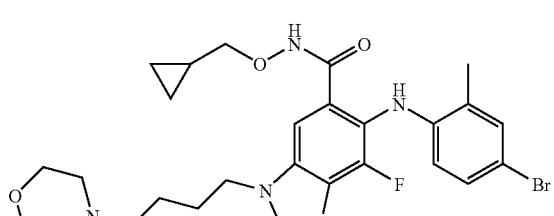
18n
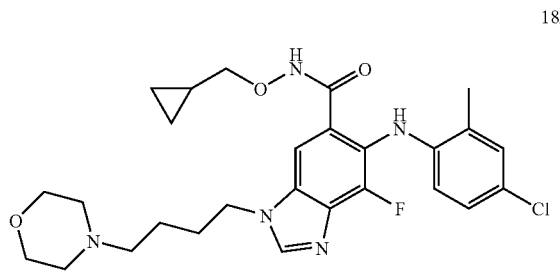
18o
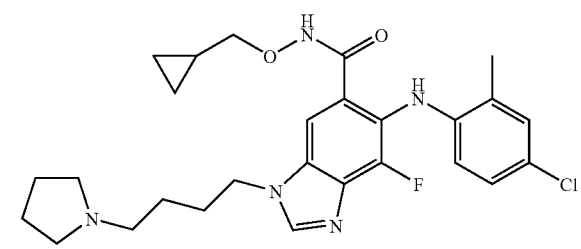
18p
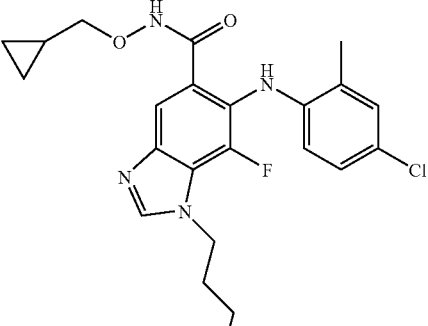
18q
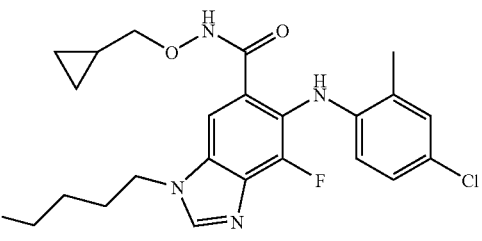
18r
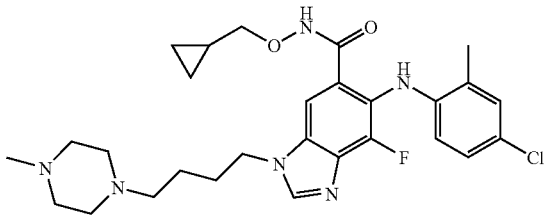
18s
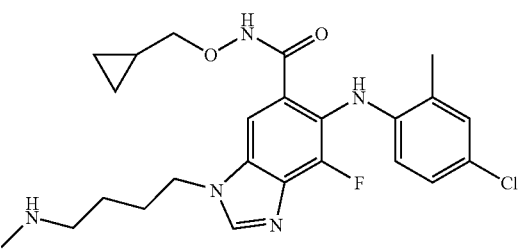

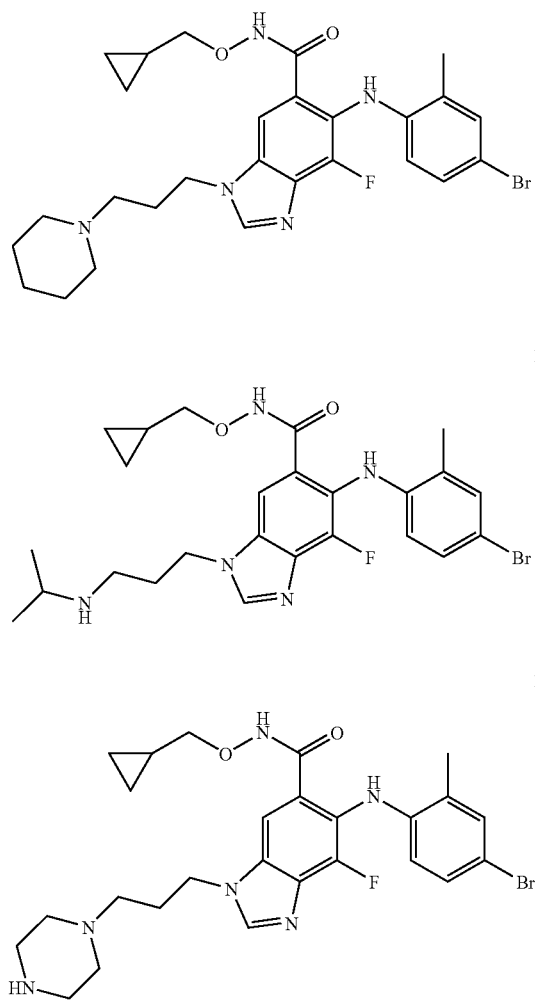

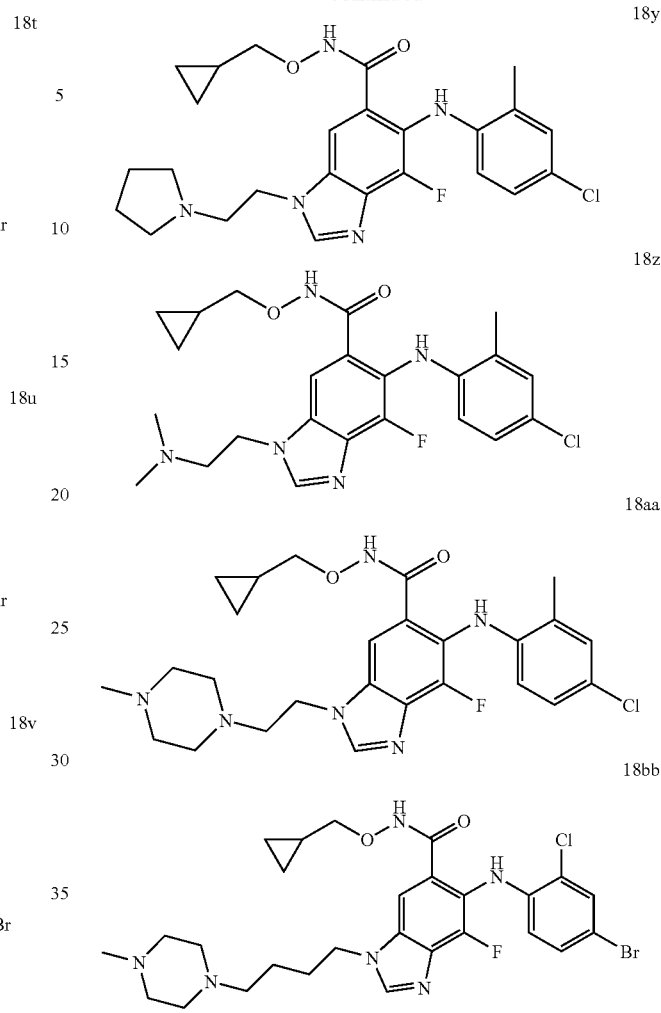

Example 21

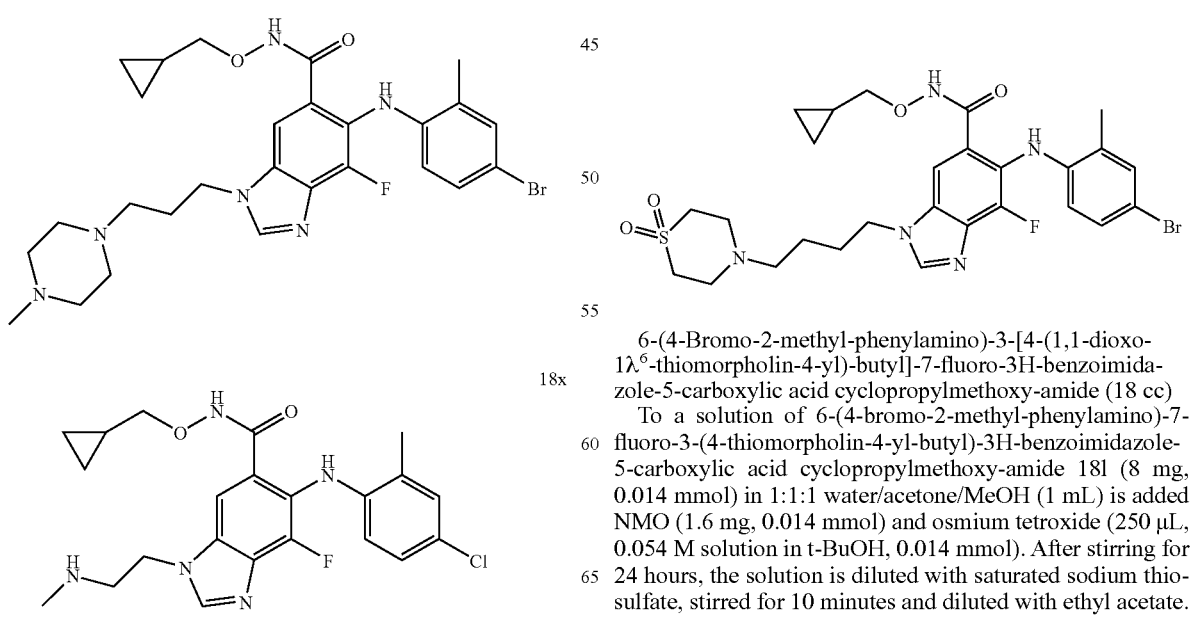

6-(4-Bromo-2-methyl-phenylamino)-3-[4-(1,1-dioxo-1λ⁶-thiomorpholin-4-yl)-butyl]-7-fluoro-3H-benzoimidazole-5-carboxylic acid cyclopropylmethoxy-amide (18 cc)

To a solution of 6-(4-bromo-2-methyl-phenylamino)-7-fluoro-3-(4-thiomorpholin-4-yl-butyl)-3H-benzoimidazole-5-carboxylic acid cyclopropylmethoxy-amide 18l (8 mg, 0.014 mmol) in 1:1:1 water/acetone/MeOH (1 mL) is added NMO (1.6 mg, 0.014 mmol) and osmium tetroxide (250 µL, 0.054 M solution in t-BuOH, 0.014 mmol). After stirring for 24 hours, the solution is diluted with saturated sodium thiosulfate, stirred for 10 minutes and diluted with ethyl acetate. The solution is washed with brine (2×), dried (Na₂SO₄) and concentrated under reduced pressure to a grey solid. FCC (10:1 dichloromethane/methanol) provides 6 mg (71%) desired product as an off-white solid. MS ESI (+) m/z 622, 624 (M+, Br pattern) detected.

Example 22

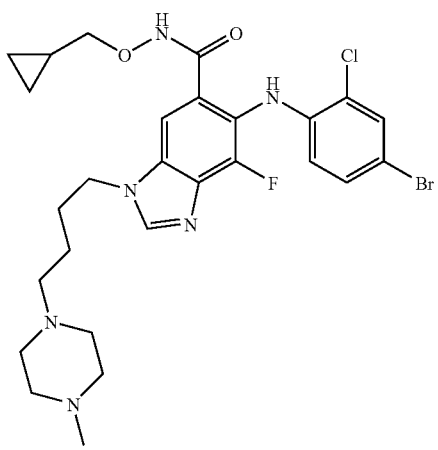

6-(4-Bromo-2-chloro-phenylamino)-7-fluoro-3-[4-(4-methyl-piperazin-1-yl)-butyl]-3H-benzoimidazole-5-carboxylic acid cyclopropylmethoxy-amide (18dd)

A solution of 6-(4-bromo-2-chloro-phenylamino)-3-(4-chloro-butyl)-7-fluoro-3H-benzoimidazole-5-carboxylic acid cyclopropylmethoxy-amide 18ee (10 mg, 0.018 mmol), sodium iodide (14 mg, 0.092 mmol), and 1-methyl-piperazine (10 μL, 0.092 mmol) are stirred at 85° C. for three hours. The reaction mixture is diluted with ethyl acetate and washed three times with water, washed twice with saturated aqueous potassium carbonate, dried ($Na_2SO_4$) and concentrated under reduced pressure to a yellow oil. Flash column chromatography (1:1 dichloromethane/methanol followed by methanol followed by 20:1 methanol/triethylamine) yields clean product (8 mg, 72%) as an off-white foam. MS ESI (+) m/z 607, 609 (M+, Br pattern) detected. $^1$H NMR (400 MHz, DMSO-$d_6$) δ 8.37 (s, 1H), 7.71 (s, 1H), 7.49 (d, 1H), 7.18 (dd, 1H), 6.40 (dd, 1H), 4.38 (t, 2H), 3.62 (d, 2H), 2.45 (broad, 8H), 2.41 (t, 2H), 2.28 (s, 3H), 1.96 (m, 2H), 1.54 (m, 2H), 1.07 (m, 1H), 0.50 (d, 2H), 0.22 (d, 2H).

Example 23

The following compounds are prepared by methods similar to those described in Example 22, using an appropriate amine and primary alkyl chloride.

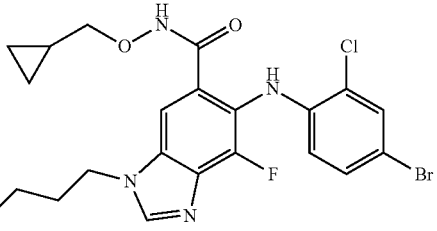

18ff

18gg

18hh

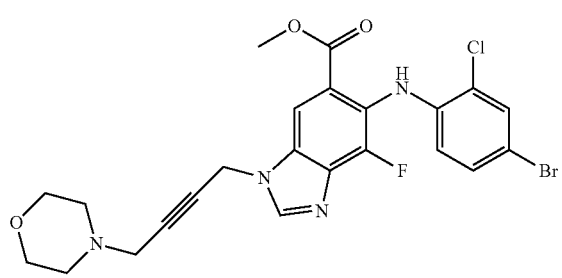

18ii

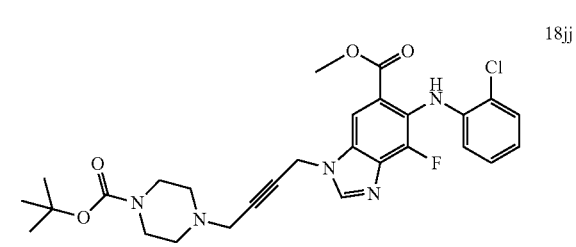

18jj

18kk
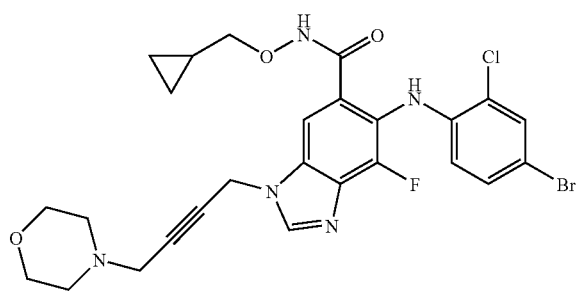
18ll
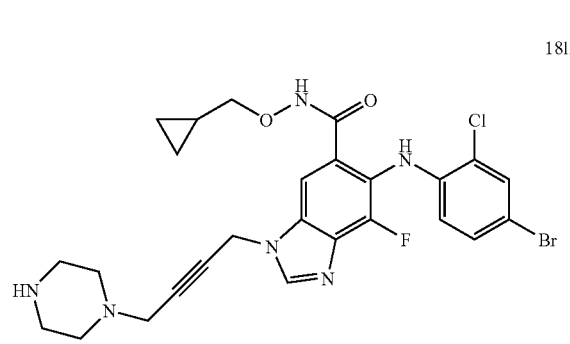
18mm
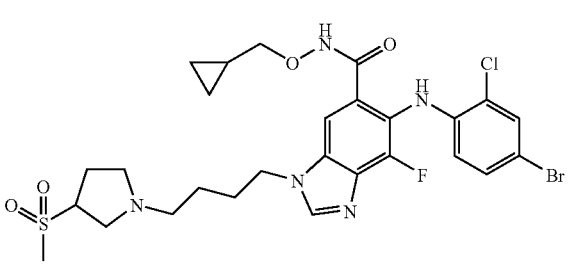
18nn
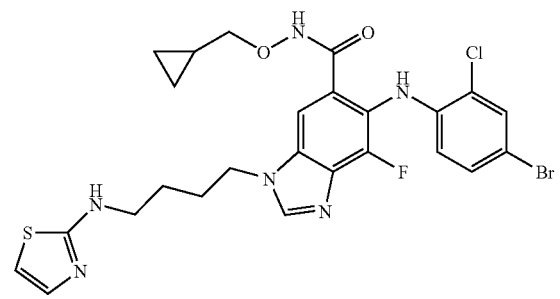
18oo
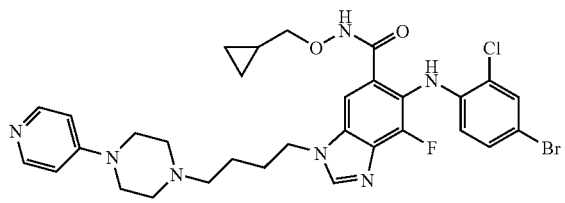
18pp
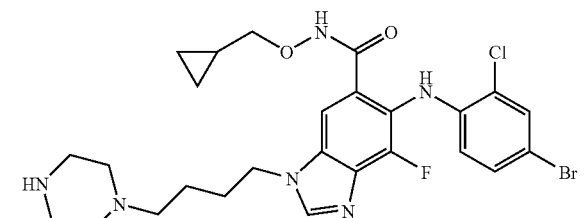
18qq
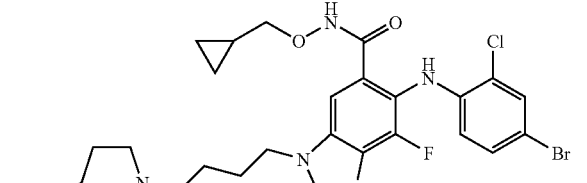
18rr
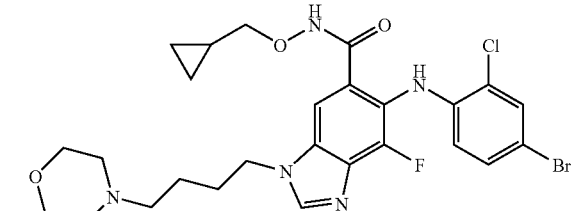
18ss
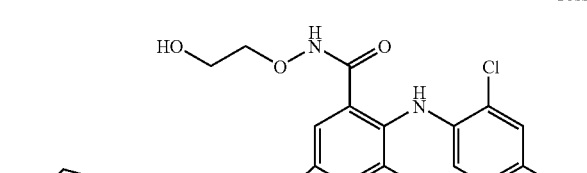
18tt
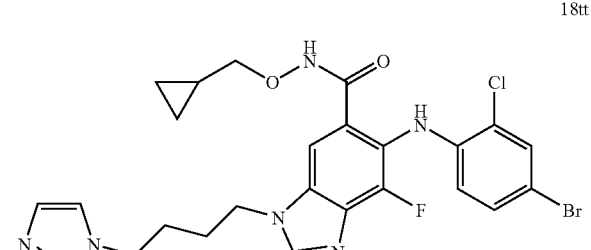
18uu
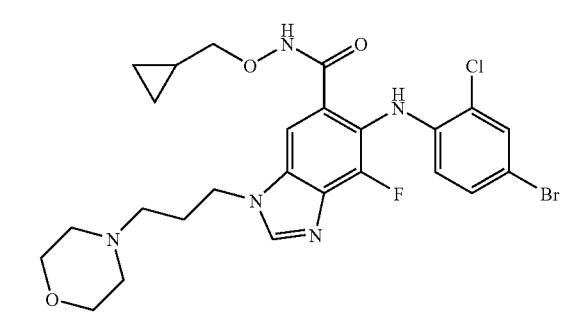

-continued
18vv
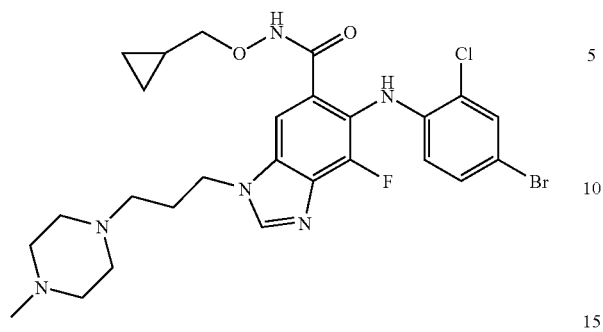
18ww
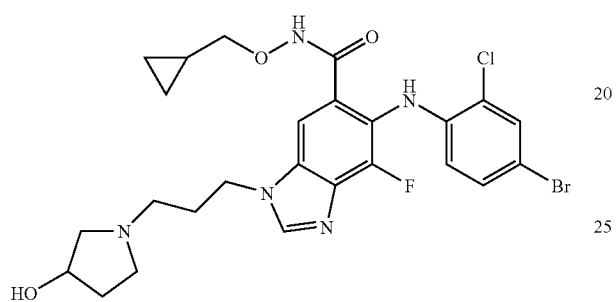
18xx
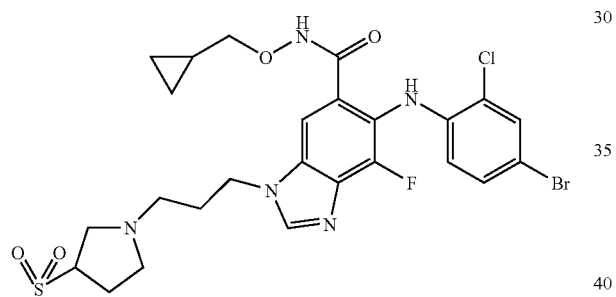
18yy
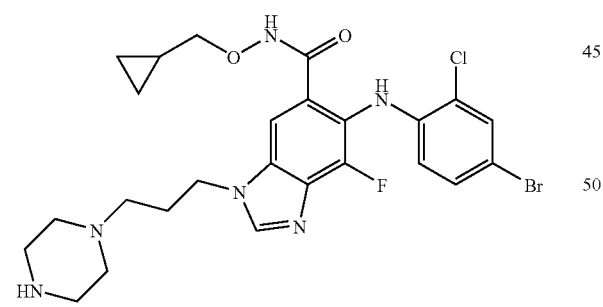
18zz
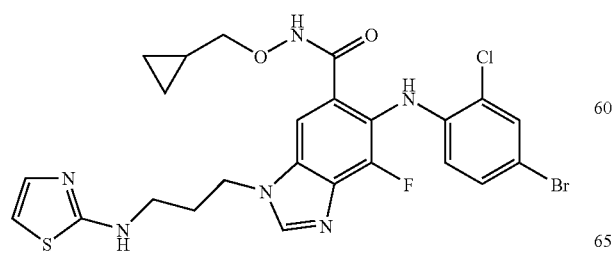
-continued
18aaa
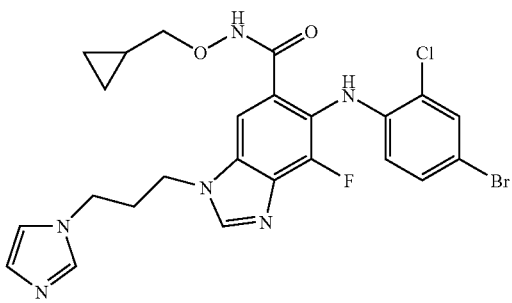
18bbb
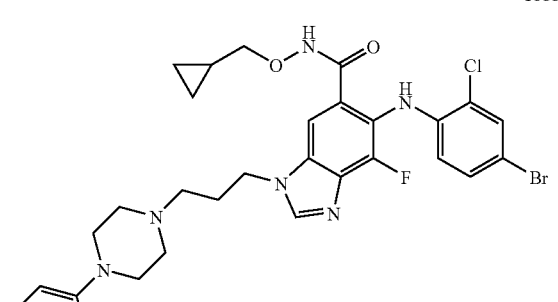
18ccc
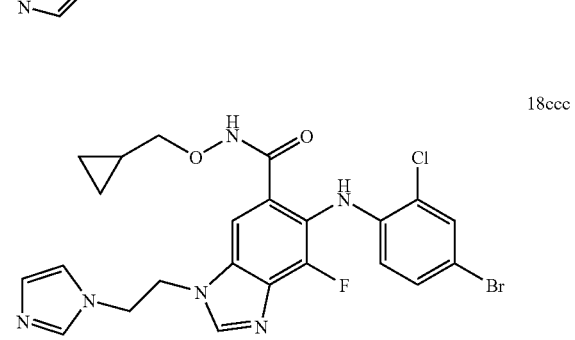
18ddd
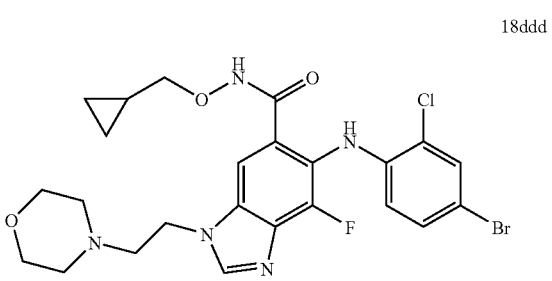
18eee
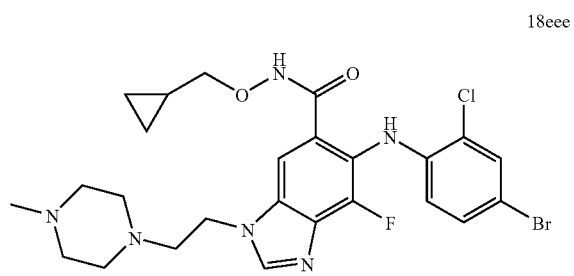

-continued

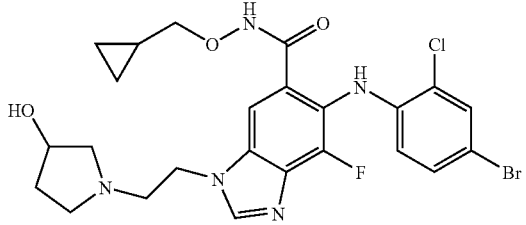

18fff

Example 24

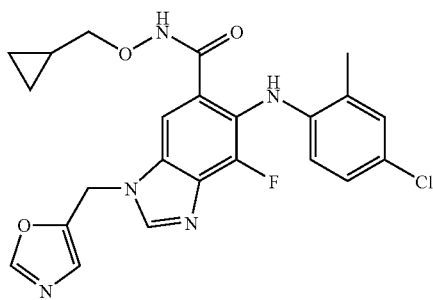

6-(4-Chloro-2-methyl-phenylamino)-7-fluoro-3-oxazol-5-ylmethyl-3H-benzoimidazole-5-carboxylic acid cyclopropylmethoxy-amide (18ggg)

6-(4-Chloro-2-methyl-phenylamino)-7-fluoro-3-(2-oxo-ethyl)-3H-benzoimidazole-5-carboxylic acid cyclopropylmethoxy-amide (0.020 g, 0.046 mmol) is dissolved in methanol (2 mL). Potassium carbonate (0.013 g, 0.093 mmol) and 1-isocyanomethanesulfonyl-4-methyl-benzene (0.010 g, 0.051 mmol) are added. The reaction mixture is stirred at reflux for 16 hours under $N_2$, then concentrated under reduced pressure. The residue is dissolved in ethyl acetate and poured into a reparatory funnel and washed with water and brine. The combined aqueous layers are reextracted with ethyl acetate (2×). The combined ethyl acetate layers are dried ($Na_2SO_4$,) and concentrated under reduced pressure. The resulting solid was purified by flash column chromatography (eluting with 15:1 methylene chloride:methanol) to yield 0.011 g (50%) of the desired product. MS APCI (+) m/z 470, 472 (M+, Cl pattern) detected; $^1$H NMR (400 MHz, $CDCl_3$) δ 10.51 (br s, 1H), 8.07 (s, 1H), 8.02 (s, 1H), 7.89 (s, 1H), 7.23 (s, 1H), 7.15 (d, 1H), 6.92 (dd, 1H), 6.31 (d, 1H), 6.11 (br s, 1H), 5.45 (s, 2H), 3.62 (d, 2H), 2.40 (s, 3H), 0.87 (m, 1H), 0.49 (m, 2H), 0.20 (m, 2H). $^{19}$F NMR (376 MHz, $CDCl_3$) −134.54 (s).

Example 25

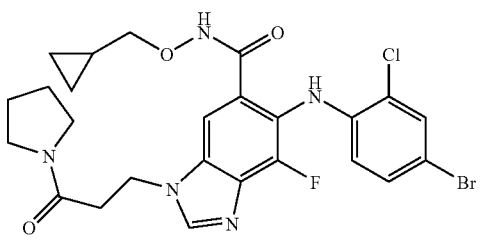

6-(4-Bromo-2-chloro-phenylamino)-7-fluoro-3-(3-oxo-3-pyrrolidin-1-yl-propyl)-3H-benzoimidazole-5-carboxylic acid cyclopropylmethoxy-amide (18hhh)

Step A: 6-(4-Bromo-2-chloro-phenylamino)-3-(2-tert-butoxycarbonyl-ethyl)-7-fluoro-3H-benzoimidazole-5-carboxylic acid methyl ester: 6-(4-Bromo-2-chloro-phenylamino)-7-fluoro-3H-benzoimidazole-5-carboxylic acid methyl ester 8b (0.50 g, 1.25 mmol) is dissolved in DMF (8 mL) under $N_2$ and $K_2CO_3$ (0.26 g, 1.88 mmol) is added followed by t-butyl acrylate (1.84 mL, 12.54 mmol). The reaction mixture is heated to 90° C. with stirring. After 4 hours, the reaction mixture is cooled to room temperature and diluted with ethyl acetate. The organic layer is washed with water (3×) and brine, dried ($MgSO_4$) and concentrated under reduced pressure. Purification by flash column chromatography eluted with 19:1 methylene chloride:ethyl acetate provides 0.41 g (62%) desired product.

Step B: 6-(4-Bromo-2-chloro-phenylamino)-3-(2-carboxy-ethyl)-7-fluoro-3H-benzoimidazole-5-carboxylic acid methyl ester TFA salt: 6-(4-Bromo-2-chloro-phenylamino)-3-(2-tert-butoxycarbonyl-ethyl)-7-fluoro-3H-benzoimidazole-5-carboxylic acid methyl ester (0.050 g, 0.095 mmol) is dissolved in methylene chloride (0.5 mL) and TFA (0.5 mL) is added. After 45 minutes, the reaction mixture is concentrated to dryness to give 0.49 g (88%) desired product: LC/MS ESI (+) m/z 472, 470 (M+ Br pattern) detected; $^1$H NMR (400 MHz, DMSO-$d_6$) δ 8.51 (s, 1H), 8.20 (s, 1H), 8.13 (s, 1H), 7.64 (d, 1H), 7.29 (dd, 1H), 6.45 (dd, 1H), 4.55 (t, 2H), 2.89 (t, 2H).

Step C: 6-(4-Bromo-2-chloro-phenylamino)-7-fluoro-3-(3-oxo-3-pyrrolidin-1-yl-propyl)-3H-benzoimidazole-5-carboxylic acid methyl ester: To solution of 6-(4-bromo-2-chloro-phenylamino)-3-(2-carboxy-ethyl)-7-fluoro-3H-benzoimidazole-5-carboxylic acid methyl ester (60 mg, 0.13 mmol) in DMF (1.8 mL) is added HOBt-$H_2O$ (24 mg, 0.16 mmol), $Et_3N$ (0.043 mL, 0.31 mmol), pyrrolidine (0.011 mL, 0.13 mmol), and EDCI (34 mg, 0.18 mmol) at room temperature. The resulting yellow solution is stirred 16 hours at room temperature. The reaction mixture is diluted with EtOAc and water, washed with sat'd aqueous $NH_4Cl$, brine, sat'd aqueous $NaHCO_3$, and brine. The organic layer is dried over $MgSO_4$, filtered, and concentrated in vacuo to give a crude material which is purified by flash chromatography (3% MeOH in $CH_2Cl_2$) to afford 45 mg (67%) of the desired product: MS APCI (+) m/z 523, 525 (M+, Br pattern) detected.

Step D: 6-(4-Bromo-2-chloro-phenylamino)-7-fluoro-3-(3-oxo-3-pyrrolidin-1-yl-propyl)-3H-benzoimidazole-5-carboxylic acid: To a solution of 6-(4-bromo-2-chloro-phenylamino)-7-fluoro-3-(3-oxo-3-pyrrolidin-1-yl-propyl)-3H-benzoimidazole-5-carboxylic acid methyl ester (41 mg, 0.079 mmol) in THF/$H_2O$ (1.5 mL/0.75 mL) is added 0.20 mL (0.20 mmol) of 1 N aqueous LiOH at room temperature. The resulting solution is stirred 16 hours. The reaction mixture is acidified with 1 N aqueous HCl (pH ~2 to 3) and diluted with EtOAc. The organic layer is dried over $MgSO_4$, filtered, and concentrated in vacuo to give a crude product (42 mg) which is directly used without further purification.

Step E: 6-(4-Bromo-2-chloro-phenylamino)-7-fluoro-3-(3-oxo-3-pyrrolidin-1-yl-propyl)-3H-benzoimidazole-5-carboxylic acid cyclopropylmethoxy-amide 18hhh: The title compound is prepared from 6-(4-bromo-2-chloro-phenylamino)-7-fluoro-3-(3-oxo-3-pyrrolidin-1-yl-propyl)-3H-benzoimidazole-5-carboxylic acid and O-cyclopropylmethyl-hydroxylamine hydrochloride by the standard coupling procedure described in Step A: MS APCI (+) m/z 578, 580 (M+, Br pattern) detected; $^1$H NMR (400 MHz, DMSO-$d_6$) δ 11.66 (s, 1H), 8.42 (s, 1H), 8.01 (s, 1H), 7.76 (s, 1H), 7.62 (s, 1H), 7.28 (d, 1H), 6.39 (m, 1H), 4.52 (t, 2H), 3.66 (d, 2H), 3.33 (t, 2H), 3.28 (t, 2H), 2.89 (t, 2H), 1.83 (m, 2H), 1.76 (m, 2H), 1.06 (m, 1H), 0.49 (m, 2H), 0.22 (m, 2H); $^{19}$F NMR (376 MHz, DMSO-$d_6$) −132.94 (s, 1F).

Example 26

The following compounds are prepared by methods similar to those described in Example 25 using methyl ester 8b and the appropriate amines:

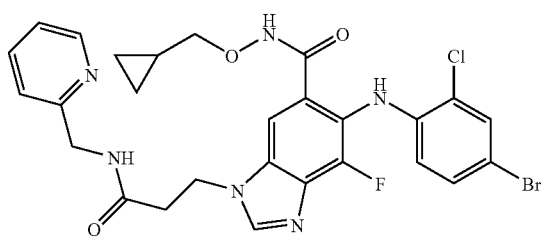

18iii

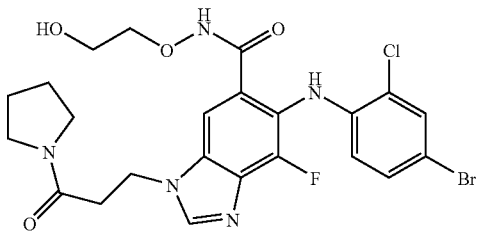

18jjj

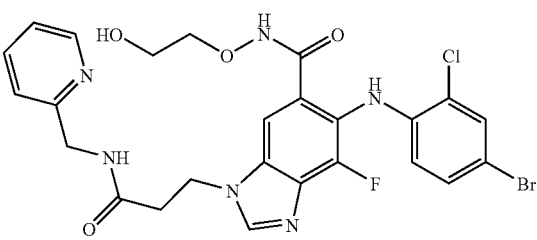

18kkk

Example 27

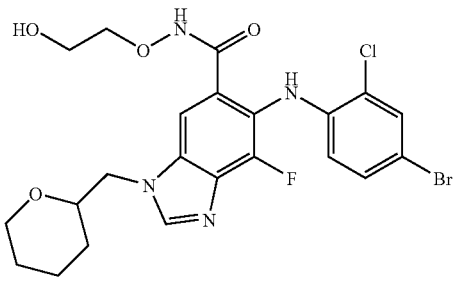

6-(4-Bromo-2-chloro-phenylamino)-7-fluoro-3-(tetrahydro-pyran-2-ylmethyl)-3H-benzoimidazole-5-carboxylic acid (2-hydroxy-ethoxy)-amide (11p)

Step A: 6-(4-Bromo-2-chloro-phenylamino)-7-fluoro-3-(tetrahydro-pyran-2-ylmethyl)-3H-benzoimidazole-5-carboxylic acid methyl ester 11q: 6-(4-Bromo-2-chloro-phenylamino)-7-fluoro-3H-benzoimidazole-5-carboxylic acid methyl ester 8b (0.25 g, 0.63 mmol) is dissolved in N,N-dimethylformamide (5 mL). 2-Bromomethyl-tetrahydro-pyran (0.34 g, 1.88 mmol) and potassium carbonate (0.26 g, 1.88 mmol) are added and the reaction mixture is stirred at 60° C. for 12 hours under $N_2$. The reaction mixture is poured into a separatory funnel, diluted with ethyl acetate and water and the layers separated. The ethyl acetate layer is washed with water and brine, dried ($Na_2SO_4$) and concentrated under reduced pressure. The resulting solid residue is triturated with diethyl ether to yield a pale yellow solid (N3 regioisomer by NMR) and a yellow filtrate (mixture of N1 and N3 regioisomers by NMR). The solids are collected and washed with diethyl ether to yield 0.12 g (37%) of the pure desired N3 regioisomeric product as a pale yellow solid. MS ESI (+) m/z 496, 498 (M+, Br pattern) detected.

Step B: 6-(4-Bromo-2-chloro-phenylamino)-7-fluoro-3-(tetrahydro-pyran-2-ylmethyl)-3H-benzoimidazole-5-carboxylic acid 11r: 6-(4-Bromo-2-chloro-phenylamino)-7-fluoro-3-(tetrahydro-pyran-2-ylmethyl)-3H-benzoimidazole-5-carboxylic acid methyl ester 11q is suspended in 4:1 tetrahydrofuran/water (2.5 mL) and aqueous 1 M LiOH is added (2.5 mL). After stirring at room temperature for 16 hours, the reaction mixture is homogeneous and the reaction is complete. The reaction mixture is cooled to 0° C., diluted with water and aqueous 2 M HCl is added dropwise until the pH of the solution is 1-2, at which time it turns to a suspension. The reaction mixture is poured into a separatory funnel and diluted with ethyl acetate/tetrahydrofuran and water and the layers separated. The aqueous layer is extracted with ethyl acetate. The combined organic layers are washed with brine, dried ($Na_2SO_4$) and concentrated under reduced pressure to yield 0.11 g (100%) of the pure desired product as a white solid. MS ESI (+) m/z 482, 484 (M+, Br pattern) detected.

Step C: 6-(4-Bromo-2-chloro-phenylamino)-7-fluoro-3-(tetrahydro-pyran-2-ylmethyl)-3H-benzoimidazole-5-carboxylic acid (2-vinyloxy-ethoxy)-amide 11s: 6-(4-Bromo-2-chloro-phenylamino)-7-fluoro-3-(tetrahydro-pyran-2-ylmethyl)-3H-benzoimidazole-5-carboxylic acid 11r (0.11 g, 0.23 mmol) is dissolved in N,N-dimethylformamide (2 mL). HOBT (0.037 g, 0.27 mmol) and triethylamine (0.094 mL, 0.68 mmol) are added. Then O-(2-vinyloxy-ethyl)-hydroxylamine (0.028 g, 0.27 mmol) and EDCI (0.056 g, 0.29 mmol) are added and the reaction mixture is stirred at room temperature under N₂ until HPLC shows the reaction is complete (2-3 days). The reaction mixture is poured into a separatory funnel, diluted with ethyl acetate and water and the layers separated. The ethyl acetate layer is washed successively with aqueous saturated NH₄Cl (2×), brine (1×), aqueous saturated sodium bicarbonate (2×), water (1×), and brine (1×), dried (Na₂SO₄) and concentrated under reduced pressure. The resulting solid is purified by FCC (eluting with 15:1 methylene chloride:methanol) to yield 0.039 g (79%) of the pure desired product as an off-white solid. MS ESI (+) m/z 567, 569 (M+, Br pattern) detected.

Step D: 6-(4-Bromo-2-chloro-phenylamino)-7-fluoro-3-(tetrahydro-pyran-2-ylmethyl)-3H-benzoimidazole-5-carboxylic acid (2-hydroxy-ethoxy)-amide 11p: 6-(4-Bromo-2-chloro-phenylamino)-7-fluoro-3-(tetrahydro-pyran-2-ylmethyl)-3H-benzoimidazole-5-carboxylic acid (2-vinyloxy-ethoxy)-amide 11s (0.039 g, 0.068 mmol) is dissolved in ethanol (2 mL) and aqueous 2 M HCl (200 uL) is added. The reaction mixture is stirred at room temperature for 30 minutes. The reaction mixture is diluted with water and then neutralized with aqueous 2 M NaOH (~200 uL) until pH 7 and concentrated under reduced pressure. The residue is partitioned between ethyl acetate and brine in a separatory funnel and the layers separated. The ethyl acetate layer is dried (Na₂SO₄) and concentrated under reduced pressure to yield 0.034 g (91%) of the pure desired product as an off-white solid. MS ESI (+) m/z 541, 543 (M+, Br pattern) detected; ¹H NMR (400 MHz, CD₃OD) δ 8.29 (s, 1H), 7.75 (s, 1H), 7.49 (d, 1H), 7.18 (dd, 1H), 6.40 (dd, 1H), 4.40 (dd, A of ABX pattern, 1H), 4.28 (dd, B of ABX pattern, 1H), 3.92 (m, X of ABX pattern, 1H), 3.66 (t, 2H), 3.35 (m, 1H), 1.89 (m, 1H), 1.76 (m, 1H), 2.28 (s, 3H), 1.54 (m, 3H), 1.30 (m, 1H). ¹⁹F NMR (376 MHz, CD₃OD) −134.87 (s).

Example 28

The following compounds are prepared by methods similar to that described in Example 27 by using the appropriate methyl ester and alkylating agent (Step A) and the appropriate hydroxylamine in (Step C).

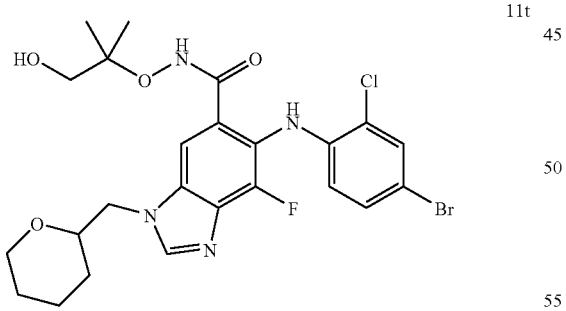

11t

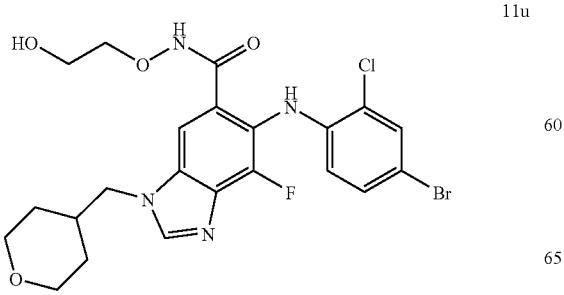

11u

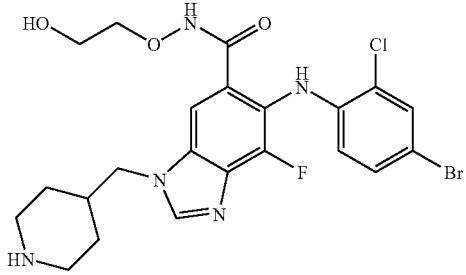

11v

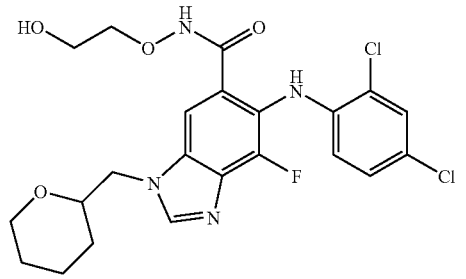

11w

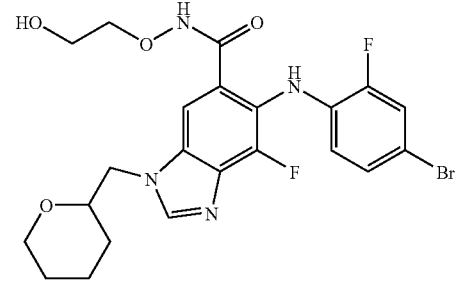

11x

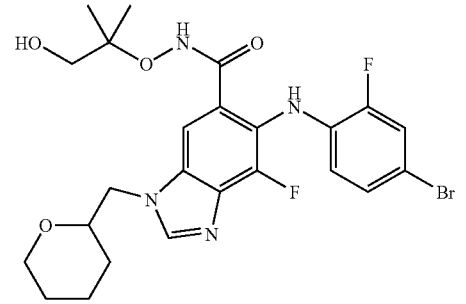

11y

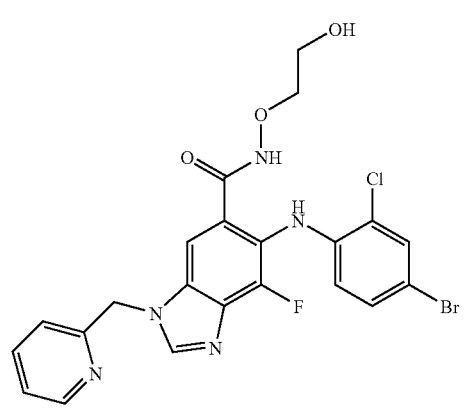

11z

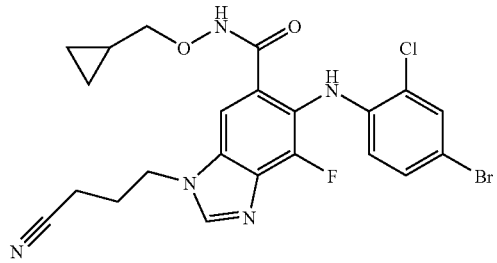

11aa

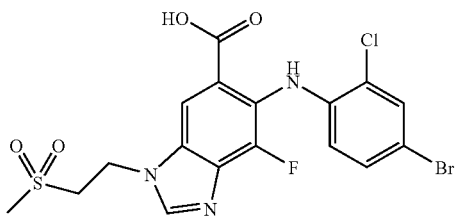

11dd

Example 29

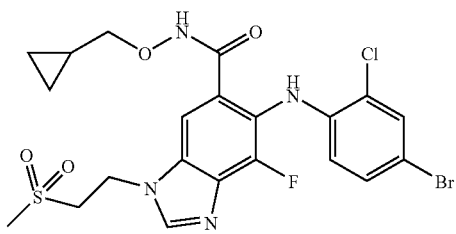

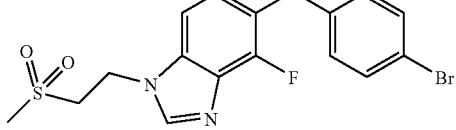

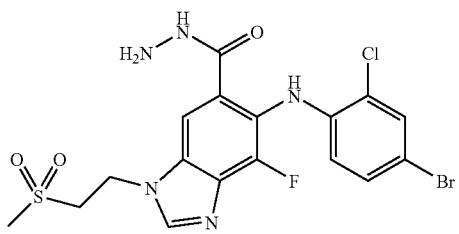

11ee 6-(4-Bromo-2-chloro-phenylamino)-7-fluoro-3-(2-methanesulfonyl-ethyl)-3H-benzoimidazole-5-carboxylic acid cyclopropylmethoxy-amide (11bb)

Step A: 6-(4-Bromo-2-chloro-phenylamino)-7-fluoro-3-(2-methanesulfonyl-ethyl)-3H-benzoimidazole-5-carboxylic acid methyl ester 11cc: 6-(4-Bromo-2-chloro-phenylamino)-7-fluoro-3H-benzoimidazole-5-carboxylic acid methyl ester 8b (1.55 g, 3.89 mmol) is dissolved in 15 mL DMF under $N_2$. $K_2CO_3$ (0.70 g, 5.06 mmol) is added followed by methyl vinyl sulfone (0.41 mL, 4.67 mmol). After stirring 16 hours at room temperature, the reaction mixture is diluted with ethyl acetate and water. The layers are separated and the organic layer is washed with water (3×) and brine. The combined aqueous washes are extracted with ethyl acetate. The combined organic extracts are dried ($MgSO_4$) and concentrated under reduced. Purification by dissolving the residue in methylene chloride and precipitating with diethyl ether, repeated several times, provides 1.16 g (59%) pure desired product as a yellow solid: MS APCI (+) m/z 506, 504 (M+ Br pattern) and 400, 398 (M– methyl ethyl sulfone Br pattern).

Step B: 6-(4-Bromo-2-chloro-phenylamino)-7-fluoro-3-(2-methanesulfonyl-ethyl)-3H-benzoimidazole-5-carboxylic acid cyclopropylmethoxy-amide 11bb: 6-(4-Bromo-2-chloro-phenylamino)-7-fluoro-3-(2-methanesulfonyl-ethyl)-3H-benzoimidazole-5-carboxylic acid methyl ester 11cc is subjected to methods previously described to give 6-(4-bromo-2-chloro-phenylamino)-7-fluoro-3-(2-methanesulfonyl-ethyl)-3H-benzoimidazole-5-carboxylic acid cyclopropylmethoxy-amide: MS APCI (+) m/z 561, 559 (M+ Br pattern) and MS APCI (–) m/z 559, 557 (M– Br pattern) detected; $^1$H NMR (400 MHz, DMSO-$d_6$) δ11.75 (s, 1H), 8.47 (s, 1H), 8.04 (s, 1H), 7.77 (s, 1H), 7.62 (d, 1H), 7.28 (dd, 1H), 6.40 (dd, 1H), 4.78 (t, 2H), 3.82 (t, 2H), 3.62 (d, 2H), 3.07 (s, 3H), 1.02 (m, 1H), 0.49 (m, 2H), 0.21 (m, 2H); $^{19}$F NMR (376 MHz, DMSO-$d_6$) –132.66 (s).

Example 30

The following compounds were prepared similarly using the appropriate methyl ester and Michael acceptor and methods described previously.

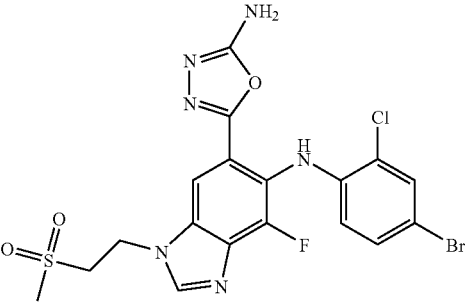

11ff

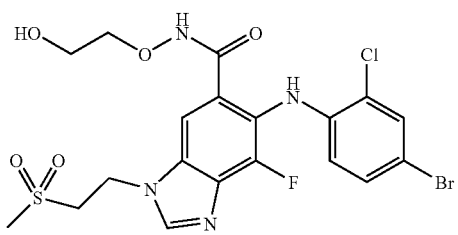

11gg

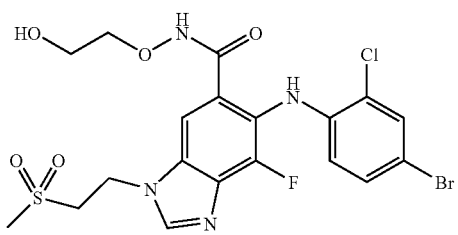

11hh

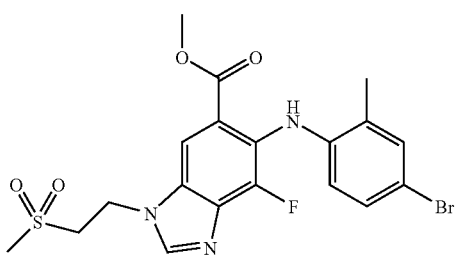

11ii

77

-continued

11jj

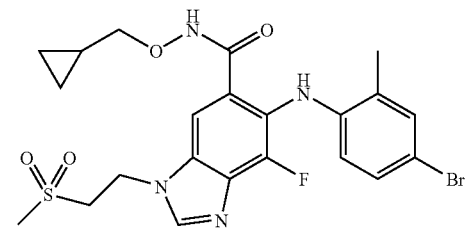

11kk

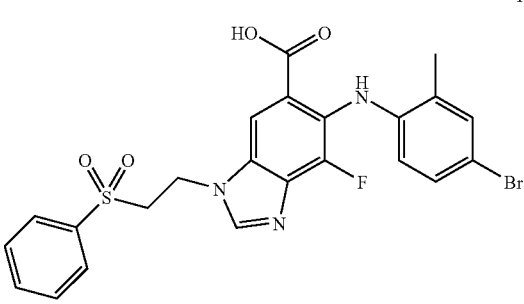

11ll

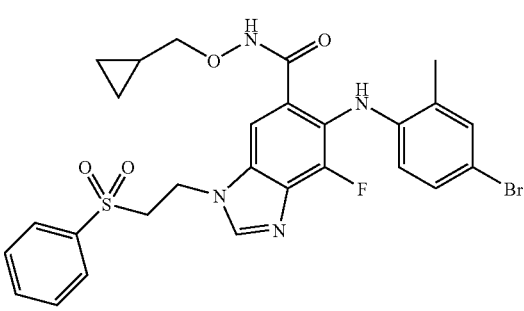

11mm

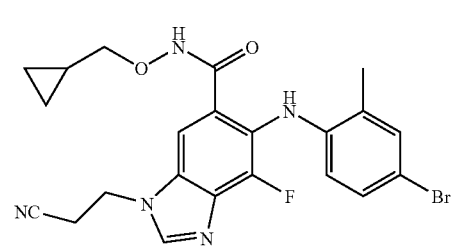

11nn

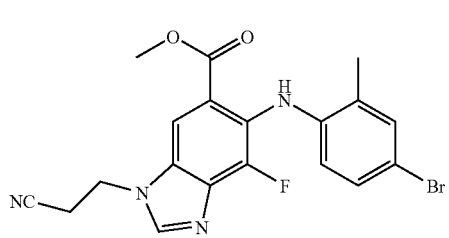

78

Example 31

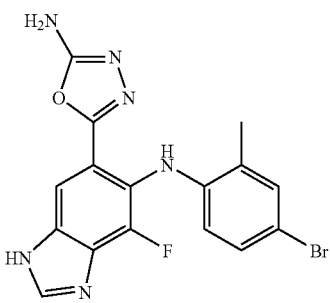

[6-(5-Amino-[1,3,4]oxadiazol-2-yl)-4-fluoro-1H-benzoimidazol-5-yl]-(4-bromo-2-methyl-phenyl)-amine (24a)

Step A: 6-(4-Bromo-2-methyl-phenylamino)-7-fluoro-3H-benzoimidazole-5-carboxylic acid hydrazide 20a: 6-(4-Bromo-2-methyl-phenylamino)-7-fluoro-3H-benzoimidazole-5-carboxylic acid methyl ester 8a (0.051 g, 0.135 mmol) is suspended in EtOH (5 mL) and hydrazine hydrate (0.118 g, 2.023 mmol) is added. The reaction mixture is heated at reflux for 16 hours. The reaction mixture is concentrated under reduced pressure and purified by FCC eluted with 97:3 ethyl acetate:MeOH to give 0.041 g (81%) of clean desired product: LC/MS ESI (+) m/z 378, 380 (M+ Br pattern) detected.

Step B: [6-(5-Amino-[1,3,4]oxadiazol-2-yl)-4-fluoro-1H-benzoimidazol-5-yl]-(4-bromo-2-methyl-phenyl)-amine 24a: 6-(4-Bromo-2-methyl-phenylamino)-7-fluoro-3H-benzoimidazole-5-carboxylic acid hydrazide 20a (0.041 g, 0.109 mmol) is suspended in 1,4-dioxane (1.5 mL) and 36 μL of a 3 M solution of cyanogen bromide in methylene chloride is added. $NaHCO_3$ (9 mg, 0.109 mmol) in water (1.5 mL) is then added. After 16 hours, the reaction mixture is diluted with water and brine and extracted with THF. The combined organic extracts are dried ($Na_2SO_4$) and concentrated under reduced pressure. Purification by FCC eluted with 98:2 ethyl acetate:MeOH provides 24 mg (55%) of pure desired product as a yellow solid: LC/MS ESI (+) m/z 403, 405 (M+ Br pattern) detected; $^1$H-NMR (400 MHz, DMSO-$d_6$) δ 12.97 (s, 1H), 8.42 (s, 1H), 7.94 (s, 1H), 7.74 (s, 1H), 7.36 (s, 2H), 7.33 (d, 1H), 7.15 (d, 1H), 6.40 (bs, 1H), 2.34 (s, 3H).

Example 32

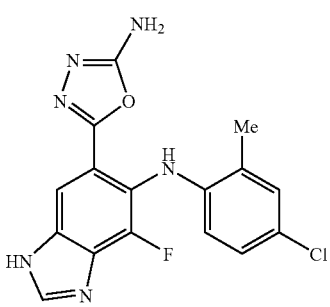

[6-(5-Amino-[1,3,4]oxadiazol-2-yl)-4-fluoro-1H-benzoimidazol-5-yl]-(4-chloro-2-methyl-phenyl)-amine (24b)

[6-(5-Amino-[1,3,4]oxadiazol-2-yl)-4-fluoro-1H-benzoimidazol-5-yl]-(4-chloro-2-methyl-phenyl)-amine 24b is prepared as described in example 31 starting with 6-(4-chloro-2-methyl-phenylamino)-7-fluoro-3H-benzoimidazole-5-carboxylic acid methyl ester 8e. LC/MS ESI (+) m/z 359, 361 (M+ Cl pattern) detected; $^1$H NMR (400 MHz, DMSO-$d_6$) δ 8.42 (s, 1H), 8.00 (bs, 1H), 7.78 (bs, 1H) 7.48 (s, 2H), 7.22 (s, 1H), 7.04 (d, 1H), 6.48 (bs, 1H), 2.37 (s, 3H).

Example 33

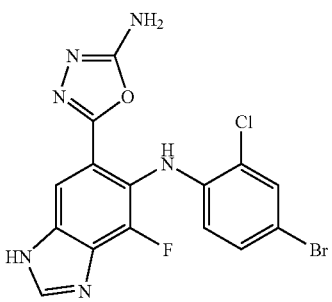

[6-(5-Amino-[1,3,4]oxadiazol-2-yl)-4-fluoro-1H-benzoimidazol-5-yl]-(4-bromo-2-chloro-phenyl)-amine (24c)

[6-(5-Amino-[1,3,4]oxadiazol-2-yl)-4-fluoro-1H-benzoimidazol-5-yl]-(4-bromo-2-chloro-phenyl)-amine 24c is prepared as described in example 31 starting with 6-(4-bromo-2-chloro-phenylamino)-7-fluoro-3H-benzoimidazole-5-carboxylic acid methyl ester 8b. MS APCI (+) m/z 425, 423 (M+ Br pattern) and MS APCI (−) m/z 423, 421 (M− Br pattern) detected.

Example 34

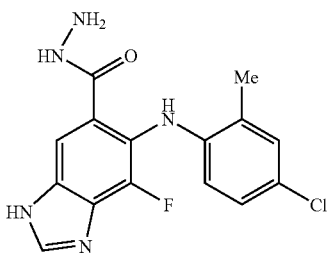

6-(4-Chloro-2-methyl-phenylamino)-7-fluoro-3H-benzoimidazole-5-carboxylic acid hydrazide (20b)

6-(4-Chloro-2-methyl-phenylamino)-7-fluoro-3H-benzoimidazole-5-carboxylic acid hydrazide 20b is prepared as described in example 31, step A from 6-(4-chloro-2-methyl-phenylamino)-7-fluoro-3H-benzoimidazole-5-carboxylic acid methyl ester 8e. LC/MS ESI (+) m/z 334, 336 (M+ Cl pattern) detected; $^1$H NMR (400 MHz, DMSO-$d_6$) δ 13.09 (bs, 1H), 9.98 (s, 1H), 8.40 (s, 1H), 8.17 (bs, 1H), 7.64 (bs, 1H), 7.20 (s, 1H), 7.03 (d, 1H), 6.41 (bs, 1H), 4.49 (s, 2H), 2.23 (s, 3H).

Example 35

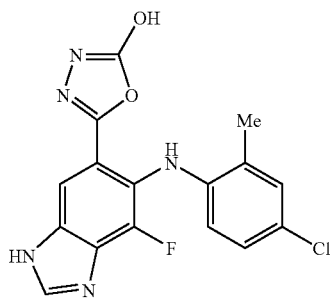

5-[6-(4-Chloro-2-methyl-phenylamino)-7-fluoro-3H-benzoimidazol-5-yl]-[1,3,4]oxadiazol-2-ol (22a)

6-(4-Chloro-2-methyl-phenylamino)-7-fluoro-3H-benzoimidazole-5-carboxylic acid hydrazide 20b (0.050 g, 0.150 mmol) is suspended in PhMe (2 mL) and a 20% phosgene solution in PhMe (0.24 mL, 0.45 mmol) is added. The reaction mixture is stirred at reflux under $N_2$ for 1 hour and then cooled to room temperature. The reaction mixture is quenched by the addition of a 1:1 mixture of THF and 10% HCl (20 mL). The layers are separated and the aqueous layer is extracted with THF (3×). The combined organic layer is washed with brine, dried ($Na_2SO_4$) and concentrated under reduced pressure to give 54 mg (99%) of desired product as a yellow solid: LC/MS ESI (+) m/z 360, 362 (M+ Cl pattern) detected; $^1$H NMR (400 MHz, DMSO-$d_6$) δ 12.64 (s, 1H), 8.83 (s, 1H), 7.88 (s, 1H), 7.30 (s, 1H), 7.20 (d, 1H), 7.00 (dd, 1H), 6.38 (dd, 1H), 2.30 (s, 3H).

Example 36

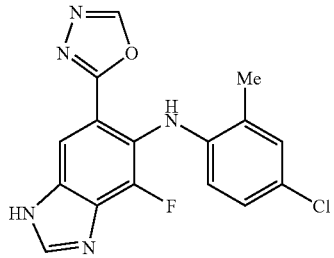

(4-Chloro-2-methyl-phenyl)-(4-fluoro-6-[1,3,4]oxadiazol-2-yl-1H-benzoimidazol-5-yl)-amine (21a)

6-(4-Chloro-2-methyl-phenylamino)-7-fluoro-3H-benzoimidazole-5-carboxylic acid hydrazide 20b (0.048 g, 0.144 mmol) is suspended in 3 mL absolute EtOH and HC(OEt)$_3$ (0.60 mL, 3.54 mmol) is added followed by catalytic pTsOH.H$_2$O. The reaction mixture is heated to reflux under $N_2$. After 2 hours, the reaction mixture is cooled to room temperature and concentrated under reduced pressure. Purification by flash column chromatography (97:3 ethyl acetate: MeOH) provides 36 mg (73%) desired product as a light yellow solid. LC/MS ESI (+) m/z 344, 346 (M+ Cl pattern) detected; $^1$H NMR (400 MHz, DMSO-d$_6$) δ13.10 (bs, 1H), 9.39 (s, 1H), 8.49 (s, 1H), 8.10 (bs, 1H), 7.78 (bs, 1H), 7.20 (d, 1H), 7.00 (dd, 1H), 6.41 (bs, 1H), 2.18 (s, 3H).

Example 37

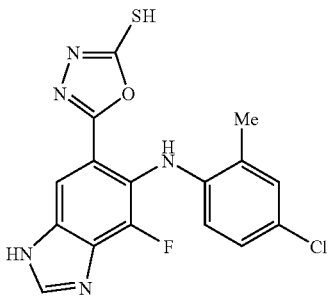

5-[6-(4-Chloro-2-methyl-phenylamino)-7-fluoro-3H-benzoimidazol-5-yl]-[1,3,4]oxadiazole-2-thiol (23a)

6-(4-Chloro-2-methyl-phenylamino)-7-fluoro-3H-benzoimidazole-5-carboxylic acid hydrazide 20b (0.050 g, 0.150 mmol) is suspended in 3 mL absolute EtOH and cooled to 0° C. under N$_2$. CS$_2$ is added (26 mg, 0.346 mmol) followed by powdered KOH (8 mg, 0.150 mmol). After stirring at 0° C. for 30 minutes, the reaction mixture is heated to reflux. After 3.5 hours, the reaction mixture is quenched by the addition of water, followed by the addition of ethyl acetate and 1N HCl. The layers are separated and the aqueous layer is extracted with ethyl acetate. The combined organic extracts are dried (Na$_2$SO$_4$) and concentrated under reduced pressure to give the desired product as a yellow solid: LC/MS ESI (+) m/z 376, 378 (M+ Cl pattern) detected; $^1$H NMR (400 MHz, DMSO-d$_6$) δ 8.51 (s, 1H), 7.92 (s, 1H), 7.19 (s, 1H), 7.12 (s, 1H), 6.98 (d, 1H), 6.29 (d, 1H), 2.28 (s, 3H).

Example 38

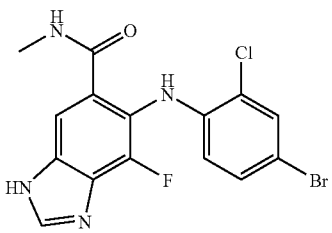

6-(4-Bromo-2-chloro-phenylamino)-7-fluoro-3H-benzoimidazole-5-carboxylic acid methylamide (11oo)

6-(4-Bromo-2-chloro-phenylamino)-7-fluoro-3H-benzoimidazole-5-carboxylic acid 10c (0.029 g, 0.076 mmol) is dissolved in N,N-dimethylformamide (1.1 mL). HOBT (0.016 g, 0.10 mmol), triethylamine (0.028 mL, 0.20 mmol), methylamine (0.059 mL, 0.12 mmol, 2 M solution in tetrahydrofuran), and EDCI (0.019 g, 0.10 mmol) are added consecutively to the reaction mixture at room temperature. The solution is stirred at room temperature for 16 hours under N$_2$. The reaction mixture is poured into a reparatory funnel and diluted with ethyl acetate and water and the layers separated. The ethyl acetate layer is washed successively with aqueous saturated NH$_4$Cl (2×), brine (1×), aqueous saturated sodium bicarbonate (2×), water (1×), and brine (1×), dried (MgSO$_4$) and concentrated under reduced pressure. The resulting solid is purified by FCC (eluting with 19:1 methylene chloride: methanol) to yield 0.013 g (42%) of the pure desired product. MS APCI (+) m/z 397, 399 (M+, Br pattern) detected; $^1$H NMR (400 MHz, DMSO-d6) δ 8.76 (broad s, 1H), 8.69 (m, 1H), 8.41 (s, 1H), 7.76 (s, 1H), 7.63 (d, 1H), 7.30 (dd, 1H), 6.50 (dd, 1H), 2.76 and 2.75 (s and s, 3H total, amide rotamers). $^{19}$F NMR (376 MHz, DMSO-d6) −132.69 (s).

Example 39

The following compounds are prepared using methods similar to that described above in Example 38 by using the appropriate carboxylic acid and amine. In those cases that contain two amine functionalities, the appropriate mono-Boc protected amine is used in the coupling reaction and the Boc group is later removed in a final step under standard TFA deprotection conditions.

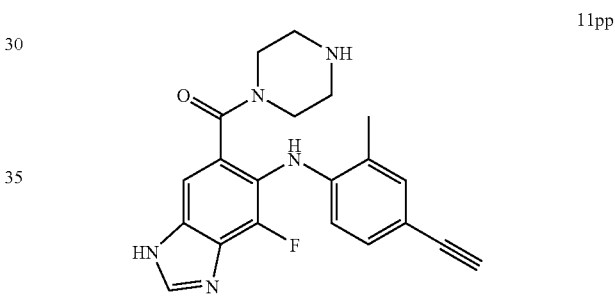

11pp

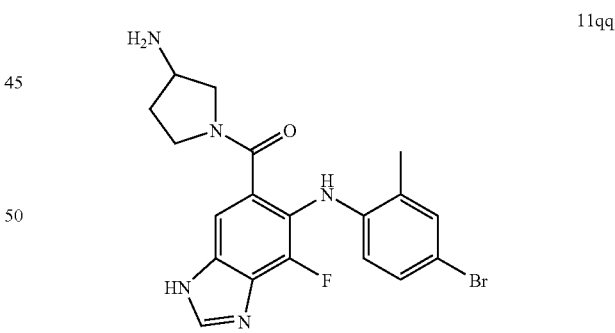

11qq

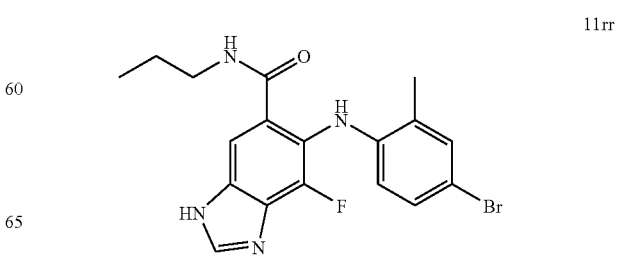

11rr

11ss 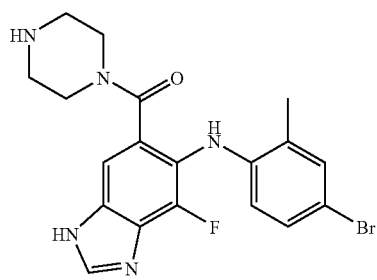

11tt 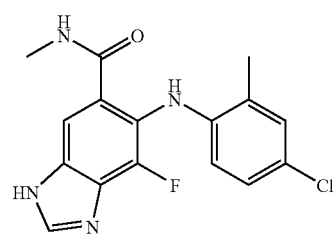

11uu 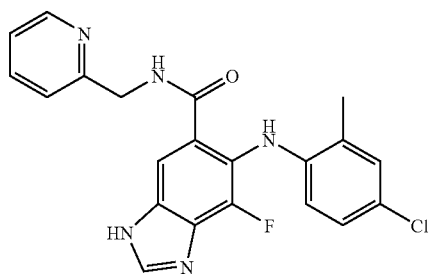

11vv 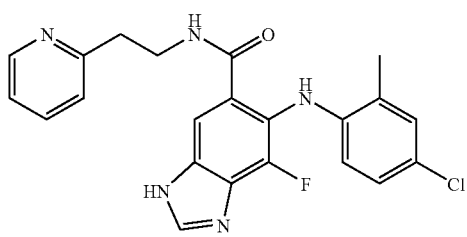

11ww 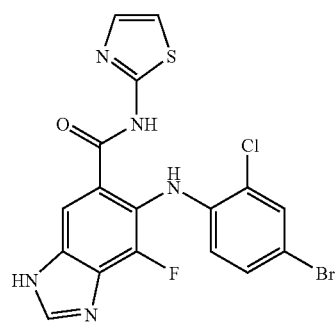

11xx 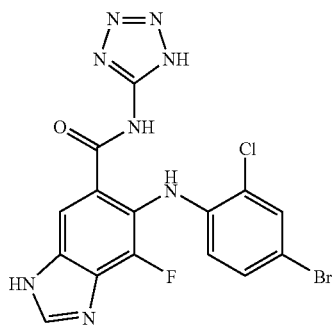

Example 40

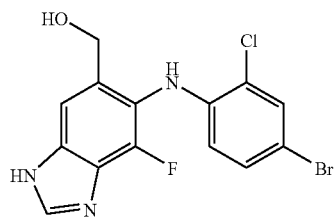

[6-(4-Bromo-2-chloro-phenylamino)-7-fluoro-3H-benzoimidazol-5-yl]-methanol (10e)

6-(4-Bromo-2-chloro-phenylamino)-7-fluoro-3H-benzoimidazole-5-carboxylic acid methyl ester 8b (1.06 g, 2.65 mmol) is suspended in tetrahydrofuran (25 mL) and cooled to −78° C. Lithium aluminum hydride (8.03 mL, 8.03 mmol, 1M solution in tetrahydrofuran) is added dropwise to the reaction mixture. After stirring for 10 minutes at −78° C., the reaction mixture is warmed to 0° C. and becomes a homogeneous solution. The reaction mixture is stirred for 5 minutes at 0° C. and then cooled again to −78° C. The reaction mixture is quenched with MeOH, diluted with Rochelle's salt, warmed to room temperature and stirred for 1 hour. The reaction mixture is then poured into a separatory funnel, diluted with ethyl acetate, and the layers separated. The aqueous phase is extracted with ethyl acetate. The combined ethyl acetate layers are dried ($Na_2SO_4$) and concentrated under reduced pressure to yield 0.98 g (100%) of the pure desired product as a pale yellow solid. MS ESI (+) m/z 370, 372 (M+, Br pattern) detected.

Example 41

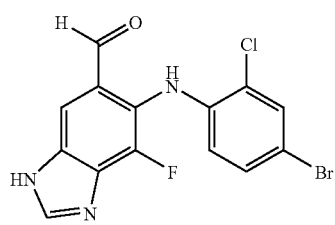

6-(4-Bromo-2-chloro-phenylamino)-7-fluoro-3H-benzoimidazole-5-carbaldehyde (10f)

[6-(4-Bromo-2-chloro-phenylamino)-7-fluoro-3H-benzoimidazol-5-yl]-methanol 10e (0.96 g, 2.58 mmol) is dissolved in tetrahydrofuran/acetone (1:1, 15 mL), and $MnO_2$ (2.24 g, 25.8 mmol) is added. The reaction mixture is stirred at 50° C. for 10 hours under $N_2$. The reaction mixture is filtered through silica gel and eluted with methylene chloride/methanol (10:1, 1 L). The filtrate is concentrated under reduced pressure to a small volume and then filtered through an Acrodisc syringe filter to remove small amounts of $MnO_2$ that passed through the silica gel. The filtrate is concentrated under reduced pressure and the residue is purified by flash column chromatography (eluting with 20:1 methylene chloride:methanol) to yield 0.81 g (85%) of the pure desired product as a bright yellow solid. MS ESI (+) m/z 368, 370 (M+, Br pattern) detected.

Example 42

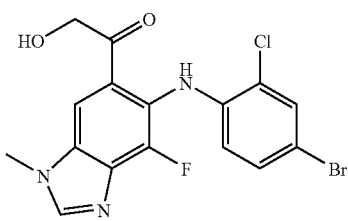

1-[6-(4-Bromo-2-chloro-phenylamino)-7-fluoro-3-methyl-3H-benzoimidazol-5-yl]-2-hydroxy-ethanone (10g)

Step A: 1-[6-(4-Bromo-2-chloro-phenylamino)-7-fluoro-3-methyl-3H-benzoimidazol-5-yl]-2-methoxymethoxy-ethanol 10i: To a solution of tributyl-methoxymethoxymethyl-stannane (864 mg, 2.37 mmol, prepared by the procedure reported in J. Org. Chem. 1988, 53, 4131) in THF (8 mL) at −78° C. is added n-BuLi (0.94 mL, 2.35 mmol, 2.5 M solution in hexane). After stirring for 3 minutes, a solution of 6-(4-bromo-2-chloro-phenylamino)-7-fluoro-3-methyl-3H-benzoimidazole-5-carb aldehyde 10h (59 mg, 0.15 mmol) in THF (2 mL) is added at −78° C. After stirring for 40 minutes at −78° C., the reaction is quenched with saturated aqueous $NH_4Cl$ at −78° C., warmed to room temperature, and diluted with EtOAc. The organic layer is washed with brine, dried over $MgSO_4$, filtered, concentrated, and purified by flash chromatography (1.5% MeOH in $CH_2Cl_2$) to give the desired product (45 mg, 64%): MS APCI (+) m/z 458, 460 (M+, Br pattern) detected.

Step B: 1-[6-(4-Bromo-2-chloro-phenylamino)-7-fluoro-3-methyl-3H-benzoimidazol-5-yl]-2-methoxymethoxy-ethanone 10j: A solution of 1-[6-(4-bromo-2-chloro-phenylamino)-7-fluoro-3-methyl-3H-benzoimidazol-5-yl]-2-methoxymethoxy-ethanol 10i (44 mg, 0.096 mmol) and the Dess-Martin periodinane (49 mg, 0.12 mmol) in $CH_2Cl_2$ (1.5 mL) is stirred for 1.5 hours at room temperature. The reaction mixture is diluted with ether (3 mL). Saturated aqueous $NaHCO_3$ (1 mL) containing sodium thiosulfate pentahydrate (74 mg) is added. The resulting mixture is stirred for 10 minutes and diluted with EtOAc. The organic layer is washed with saturated aqueous $NaHCO_3$ and brine, dried over $MgSO_4$, filtered, and concentrated in vacuo to give a crude material which is purified by flash chromatography (1.5% MeOH in $CH_2Cl_2$) to afford the desired product (31 mg, 71%): MS APCI (+) m/z 456, 458 (M+, Br pattern) detected.

Step C: 1-[6-(4-Bromo-2-chloro-phenylamino)-7-fluoro-3-methyl-3H-benzoimidazol-5-yl]-2-hydroxy-ethanone 10g: A mixture of 1-[6-(4-bromo-2-chloro-phenylamino)-7-fluoro-3-methyl-3H-benzoimidazol-5-yl]-2-methoxymethoxy-ethanone 10j (15 mg, 0.033 mmol), 10% aqueous HCl (0.3 mL), methanol (0.01 mL), and water (0.05 mL) is stirred for 3 days at room temperature. The reaction mixture is neutralized with saturated aqueous $NaHCO_3$, and diluted with EtOAc. The organic layer is washed with brine, dried over $MgSO_4$, filtered, concentrated in vacuo, and purified by flash chromatography (1.5% MeOH in $CH_2Cl_2$) to afford the desired product (7.3 mg, 54%): MS APCI (+) m/z 412, 414 (M+, Br pattern) detected; $^1H$ NMR (400 MHz, acetone-$d_6$) δ 8.64 (s, 1H), 8.34 (s, 1H), 8.16 (s, 1H), 7.58 (d, 1H), 7.31 (dd, 1H), 6.59 (dd, 1H), 4.94 (s, 2H), 4.06 (s, 3H); $^{19}F$ NMR (376 MHz, acetone-$d_6$) −132.45 (s, 1F).

Example 43

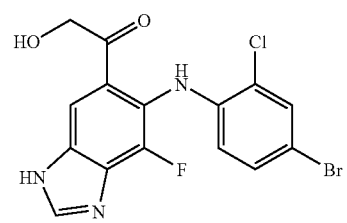

1-[6-(4-Bromo-2-chloro-phenylamino)-7-fluoro-3H-benzoimidazol-5-yl]-2-hydroxy-ethanone (10k)

Step A: 1-[6-(4-Bromo-2-chloro-phenylamino)-7-fluoro-3H-benzoimidazol-5-yl]-2-methoxymethoxy-ethanol 10l: 6-(4-Bromo-2-chloro-phenylamino)-7-fluoro-3H-benzoimidazole-5-carbaldehyde 10f is treated with tributyl-methoxymethoxymethyl-stannane according to the procedure described in Example 42, Step A to yield compound 10l. MS APCI (+) m/z 444, 446 (M+, Br pattern) detected.

Step B: 1-[6-(4-Bromo-2-chloro-phenylamino)-7-fluoro-3H-benzoimidazol-5-yl]-2-methoxymethoxy-ethanone 10m: To a solution of oxalyl chloride (0.11 mL, 0.22 mmol) in $CH_2Cl_2$ (1 mL) at −78° C. is added DMSO (0.016 mL, 0.22 mmol). After stirring for 3 minutes, a solution of 1-[6-(4-bromo-2-chloro-phenylamino)-7-fluoro-3H-benzoimidazol-5-yl]-2-methoxymethoxy-ethanol 10l (25 mg, 0.056 mmol) in methylene chloride (1 mL) is added. The resulting solution is stirred for 30 minutes at −78° C. TEA (0.1 mL, 0.71 mmol) is added. The reaction mixture is slowly warmed to room temperature, stirred for 5 minutes at room temperature, and diluted with water and $CH_2Cl_2$. The organic layer is separated, dried over $MgSO_4$, filtered, and concentrated to give the crude product which is directly used without further purification.

Step C: 1-[6-(4-Bromo-2-chloro-phenylamino)-7-fluoro-3H-benzoimidazol-5-yl]-2-hydroxy-ethanone 10k: 1-[6-(4-Bromo-2-chloro-phenylamino)-7-fluoro-3H-benzoimidazol-5-yl]-2-methoxymethoxy-ethanone 10m is deprotected according to the procedure described in Example 42, Step C to yield compound 10k. MS APCI (+) m/z 398, 400 (M+, Br pattern) detected; $^1H$ NMR (400 MHz, $CD_3OD$) δ 8.38 (s, 1H), 8.04 (s, 1H), 7.52 (d, 1H), 7.22 (dd, 1H), 6.53 (dd, 1H), 4.90 (m, 2H); $^{19}$F NMR (376 MHz, CD$_3$OD) −133.96 (s, 1F).

Example 44

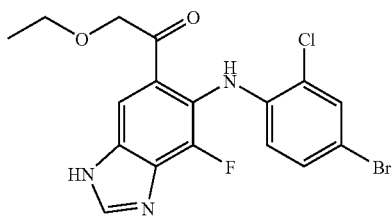

1-[6-(4-Bromo-2-chloro-phenylamino)-7-fluoro-3H-benzoimidazol-5-yl]-2-ethoxy-ethanone (10n)

Step A: 1-[6-(4-Bromo-2-chloro-phenylamino)-7-fluoro-3H-benzoimidazol-5-yl]-2-ethoxy-ethanol 10o: To a solution of lithiomethyl ethyl ether in THF (6 mL) (prepared from 4,4'-di-tert-butylbiphenyl (585 mg, 2.20 mmol), Li (18 mg, 2.59 mmol), and EtOCH$_2$Cl (0.20 mL, 2.05 mmol) by the procedure reported in Tetrahedron 1996, 52, 1643) is added a solution of 6-(4-bromo-2-chloro-phenylamino)-7-fluoro-3H-benzoimidazole-5-carbaldehyde 10f (29 mg, 0.080 mmol) in THF (1 mL) at −78° C. The resulting solution is stirred for 1 hour and then quenched with saturated aqueous NH$_4$Cl at −78° C., warmed to room temperature, and extracted with EtOAc. The organic layer is washed with brine, dried over MgSO$_4$, filtered, concentrated in vacuo, and purified by flash chromatography (100% CH$_2$Cl$_2$ to 3% to 5% MeOH in CH$_2$Cl$_2$) to give the desired product (15 mg, 44%): MS APCI (+) m/z 428, 430 (M+, Br pattern) detected.

Step B: 1-[6-(4-Bromo-2-chloro-phenylamino)-7-fluoro-3H-benzoimidazol-5-yl]-2-ethoxy-ethanone 10n: The title compound is prepared from 1-[6-(4-Bromo-2-chloro-phenylamino)-7-fluoro-3H-benzoimidazol-5-yl]-2-ethoxy-ethanol 10o according to the procedure described in Example 42, Step B except that the reaction mixture is not treated with saturated aqueous NaHCO$_3$ containing sodium thiosulfate pentahydrate. MS APCI (+) m/z 426, 428 (M+, Br pattern) detected; $^1$H NMR (400 MHz, CD$_3$OD) δ 8.36 (s, 1H), 8.04 (s, 1H), 7.51 (d, 1H), 7.21 (dd, 1H), 6.51 (dd, 1H), 4.76 (s, 2H), 3.57 (q, 2H), 1.19 (t, 3H); $^{19}$F NMR (376 MHz, CD$_3$OD) −133.96 (s).

Example 45

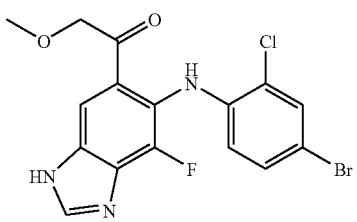

1-[6-(4-Bromo-2-chloro-phenylamino)-7-fluoro-3H-benzoimidazol-5-yl]-2-methoxy-ethanone (10p)

1-[6-(4-Bromo-2-chloro-phenylamino)-7-fluoro-3H-benzoimidazol-5-yl]-2-methoxy-ethanone 10p is prepared from 6-(4-bromo-2-chloro-phenylamino)-7-fluoro-3H-benzoimidazole-5-carbaldehyde 10f and lithiomethyl methyl ether by the procedures described in Example 44. MS APCI (+) m/z 412, 414 (M+, Br pattern) detected.

Example 46

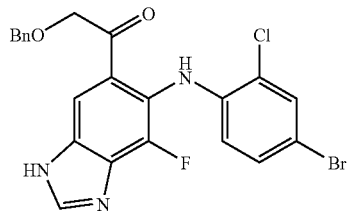

2-Benzyloxy-1-[6-(4-bromo-2-chloro-phenylamino)-7-fluoro-3H-benzoimidazol-5-yl]-ethanone (10q)

Step A: 2-Benzyloxy-1-[6-(4-bromo-2-chloro-phenylamino)-7-fluoro-3H-benzoimidazol-5-yl]-ethanol 10r: To a solution of benzyloxymethyllithium in THF (2 mL, prepared from n-Bu$_3$SnCH$_2$OBn (505 mg, 1.23 mmol) and n-BuLi (0.49 mL, 1.22 mmol, 2.5 M solution in hexane) by the procedure reported in J. Am. Chem. Soc. 1978, 100, 1481) is added a solution of 6-(4-bromo-2-chloro-phenylamino)-7-fluoro-3H-benzoimidazole-5-carbaldehyde 10f (51 mg, 0.14 mmol) in THF (3 mL) at −78° C. The resulting solution is stirred for 1 hour at −78° C. The reaction is quenched with saturated aqueous NH$_4$Cl, and extracted with EtOAc. The organic layer is dried over MgSO$_4$, filtered, concentrated in vacuo, and purified by flash chromatography (100% CH$_2$Cl$_2$ to 3% MeOH in CH$_2$Cl$_2$) to afford the desired product (46 mg, 68%): MS APCI (+) m/z 490, 492 (M+, Br pattern) detected.

Step B: 2-Benzyloxy-1-[6-(4-bromo-2-chloro-phenylamino)-7-fluoro-3H-benzoimidazol-5-yl]-ethanone 10q: The title compound is prepared from 2-benzyloxy-1-[6-(4-bromo-2-chloro-phenylamino)-7-fluoro-3H-benzoimidazol-5-yl]-ethanol 10r by the procedure described in Example 42, Step B except that the reaction mixture is not treated with saturated aqueous NaHCO$_3$ containing sodium thiosulfate pentahydrate: MS APCI (+) m/z 488, 490 (M+, Br pattern) detected; $^1$H NMR (400 MHz, CD$_3$OD) δ 8.37 (s, 1H), 8.02 (s, 1H), 7.51 (d, 1H), 7.26 (m, 5H), 7.19 (dd, 1H), 6.46 (dd, 1H), 4.77 (s, 2H), 4.58 (s, 2H); $^{19}$F NMR (376 MHz, CD$_3$OD) −134.52 (s).

Example 47

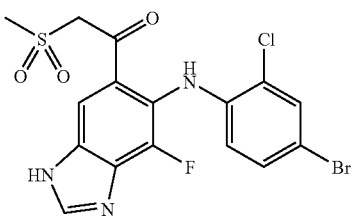

1-[6-(4-Bromo-2-chloro-phenylamino)-7-fluoro-3H-benzoimidazol-5-yl]-2-methanesulfonyl-ethanone (10s)

Step A: 1-[6-(4-Bromo-2-chloro-phenylamino)-7-fluoro-3H-benzoimidazol-5-yl]-2-methanesulfonyl-ethanol 10t: To a solution of methyl sulfone (65 mg, 0.68 mmol) in THF (1.5 mL) is added a solution of n-BuLi (0.27 mL, 0.68 mmol, 2.5 M solution in hexane) at −78° C. After stirring for 5 minutes, HMPA (0.1 mL) is added. After stirring for additional 10 minutes, a solution of 6-(4-bromo-2-chloro-phenylamino)-7-fluoro-3H-benzoimidazole-5-carbaldehyde 10f (26 mg, 0.069 mmol) in THF (1 mL) is added. The resulting solution is stirred for 1.5 hours at −78° C. The reaction is quenched with saturated aqueous NH$_4$Cl, warmed to room temperature, and diluted with EtOAc. The organic layer is washed with water, dried over MgSO$_4$, filtered, concentrated in vacuo, and purified by flash chromatography (3% MeOH in CH$_2$Cl$_2$) to give the crude desired product (31 mg, 96%) which is used directly without further purification: MS APCI (+) m/z 462, 464 (M+, Br pattern) detected.

Step B: 1-[6-(4-Bromo-2-chloro-phenylamino)-7-fluoro-3H-benzoimidazol-5-yl]-2-methanesulfonyl-ethanone 10s: The title compound is prepared from 1-[6-(4-bromo-2-chloro-phenylamino)-7-fluoro-3H-benzoimidazol-5-yl]-2-methanesulfonyl-ethanol 10t by the procedure described in Example 42, Step B except that the reaction mixture is not treated with saturated aqueous NaHCO$_3$ containing sodium thiosulfate pentahydrate: MS APCI (+) m/z 460, 462 (M+, Br pattern) detected; $^1$H NMR (400 MHz, acetone-d$_6$) δ 8.44 (s, 1H), 8.33 (s, 1H), 7.59 (s, 1H), 7.32 (d, 1H), 6.68 (dd, 1H), 5.00 (s, 1H), 3.15 (s, 3H); $^{19}$F NMR (376 MHz, acetone-d$_6$) −132.97 (s).

Example 48

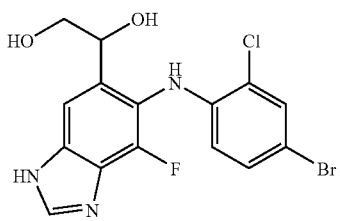

1-[6-(4-Bromo-2-chloro-phenylamino)-7-fluoro-3H-benzoimidazol-5-yl]-ethane-1,2-diol (10u)

Step A: 1-[6-(4-Bromo-2-chloro-phenylamino)-7-fluoro-3H-benzoimidazol-5-yl]-2-(isopropoxy-dimethyl-silanyl)-ethanol 10v: To a solution of the Grignard reagent prepared from Mg and chloromethyl dimethylisopropoxy silane (*Org. Synth.* 1992, 69, 96) [4.4 mL, 3.26 mmol, 0.74 M solution (based on 90% purity)] in THF, is added a solution of 6-(4-bromo-2-chloro-phenylamino)-7-fluoro-3H-benzoimidazole-5-carbaldehyde 10f (200 mg, 0.54 mmol) in THF (1 mL) at −78° C. After stirring for 1 hour at −78° C., the reaction is quenched with saturated aqueous NH$_4$Cl, and extracted with EtOAc. The organic layer is dried over MgSO$_4$, filtered, concentrated in vacuo to afford the crude desired product which is directly used without further purification.

Step B: 1-[6-(4-Bromo-2-chloro-phenylamino)-7-fluoro-3H-benzoimidazol-5-yl]-ethane-1,2-diol 10u: To the crude 1-[6-(4-bromo-2-chloro-phenylamino)-7-fluoro-3H-benzoimidazol-5-yl]-2-(isopropoxy-dimethyl-silanyl)-ethanol 10v in MeOH-THF (5 mL-5 mL) is added KHCO$_3$ (54 mg, 0.54 mmol), and KF (74 mg, 1.27 mmol), and 30% aqueous H$_2$O$_2$ (0.20 mL) at room temperature. After stirring for 3.5 hours at room temperature, the reaction mixture is diluted with water, and extracted with EtOAc. The organic layer is dried over MgSO$_4$, filtered, concentrated in vacuo, and purified by flash chromatography (8% to 10% MeOH in CH$_2$Cl$_2$) to give the desired product (74 mg, 34%): MS APCI (+) m/z 400, 402 (M+, Br pattern) detected; $^1$H NMR (400 MHz, CD$_3$OD) δ 8.20 (s, 1H), 7.62 (broad s, 1H), 7.47 (d, 1H), 7.14 (dd, 1H), 6.30 (d, 1H), 4.96 (t, 1H), 3.64 (m, 2H); $^{19}$F NMR (376 MHz, CD$_3$OD) −136.87 (s).

Example 49

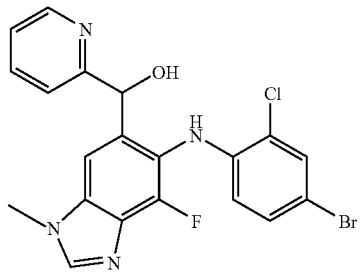

[6-(4-Bromo-2-chloro-phenylamino)-7-fluoro-3-methyl-3H-benzoimidazol-5-yl]-pyridin-2-yl-methanol (10w)

To a solution of 2-bromopyridine (0.10 mL, 1.04 mmol) in THF (3 mL) at −78° C. is added n-BuLi (0.39 mL, 0.98 mmol, 2.5 M solution in hexane). After stirring for 10 minutes at −78° C., a solution of 6-(4-bromo-2-chloro-phenylamino)-7-fluoro-3-methyl-3H-benzoimidazole-5-carbaldehyde 10h (25 mg, 0.064 mmol) in THF (1 mL) is added. The resulting reaction mixture is stirred for 1.5 hours at −78° C., quenched with saturated aqueous NH$_4$Cl, and extracted with EtOAc. The organic layer is dried over MgSO$_4$, filtered, concentrated in vacuo, and purified by flash chromatography (2.5% MeOH in CH$_2$Cl$_2$) to afford the desired product (18 mg, 62%): MS APCI (+) m/z 461, 463 (M+, Br pattern) detected; $^1$H NMR (400 MHz, CD$_3$OD) δ 8.31 (d, 1H), 8.16 (s, 1H), 7.65 (m, 3H), 7.38 (d, 1H), 7.10 (m, 1H), 7.00 (dd, 1H), 6.11 (dd, 1H), 6.05 (s, 1H), 3.94 (s, 3H); $^{19}$F NMR (376 MHz, CD$_3$OD) −135.79 (s).

Example 50

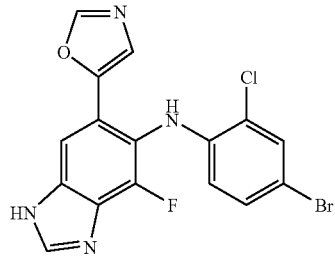

(4-Bromo-2-chloro-phenyl)-(4-fluoro-6-oxazol-5-yl-1H-benzoimidazol-5-yl)-amine (10x)

Step A: [6-(4-Bromo-2-chloro-phenylamino)-7-fluoro-3-(2-methanesulfonyl-ethyl)-3H-benzoimidazol-5-yl]-methanol 10y: 6-(4-Bromo-2-chloro-phenylamino)-7-fluoro-3-(2- methanesulfonyl-ethyl)-3H-benzoimidazole-5-carboxylic acid methyl ester 11cc (0.300 g, 0.594 mmol) is suspended in a mixture of EtOH (6 mL) and THF (4 mL) under $N_2$. $NaBH_4$ (0.112 g, 2.97 mmol) is added. After approximately 4 days stirring, reaction mixture is quenched by the addition of AcOH until the reaction mixture reaches pH 7. The reaction mixture is concentrated to dryness under reduced pressure and the residue partitioned between ethyl acetate and water. The layers are separated and the organic layer is washed with water (3×), brine, and dried ($Na_2SO_4$). The organic layer is concentrated under reduced pressure until a white precipitate forms which is collected by filtration to give 0.225 g (79%) clean desired product: LC/MS ESI (+) m/z 478, 476 (M+ Br pattern) detected.

Step B: 6-(4-Bromo-2-chloro-phenylamino)-7-fluoro-3-(2-methanesulfonyl-ethyl)-3H-benzoimidazole-5-carb aldehyde 10z: [6-(4-Bromo-2-chloro-phenylamino)-7-fluoro-3-(2-methanesulfonyl-ethyl)-3H-benzoimidazol-5-yl]-methanol 10y (0.050, 0.105 mmol) is dissolved in 1:1 THF:acetone (2 mL) under $N_2$ and $MnO_2$ (0.046 g, 0.524 mmol) is added. The reaction mixture is stirred at room temperature for 16 hours, and then at 55° C. for 5 hours. Additional $MnO_2$ (0.046 g, 0.524 mmol) is added and the reaction mixture stirred at 55° C. for 2 hours. The reaction mixture is concentrated to dryness and the residue dissolved in 10:1 methylene chloride:MeOH. The solution is filtered through a silica gel plug eluted with 10:1 methylene chloride:MeOH. The resulting filtrate is concentrated under reduced pressure to give 41 mg (82%) desired product as a bright yellow solid.

Step C: (4-Bromo-2-chloro-phenyl)-(4-fluoro-6-oxazol-5-yl-1H-benzoimidazol-5-yl)-amine 10x: 6-(4-Bromo-2-chloro-phenylamino)-7-fluoro-3-(2-methanesulfonyl-ethyl)-3H-benzoimidazole-5-carbaldehyde 10z (0.025 g, 0.053 mmol) is suspended in MeOH (2 mL) and $K_2CO_3$ (0.015 g, 0.105 mmol) is added followed by tosylmethyl isocyanide (0.011 g, 0.058 mmol). The reaction mixture is heated to reflux under $N_2$ for 16 hours. After cooling, additional tosylmethyl isocyanide (0.011 g, 0.058 mmol) is added and the reaction mixture heated to reflux under $N_2$ for 16 hours. The reaction mixture is cooled to room temperature, concentrated under reduced pressure and dissolved in ethyl acetate. The organic solution is washed with water and brine. The combined aqueous washes are extracted with ethyl acetate. The combined organic extracts are dried ($Na_2SO_4$) and concentrated under reduced pressure. Purification by flash column chromatography eluted with 20:1 methylene chloride:MeOH provides 4 mg (18%) desired product 10x and 1 mg (4%) (4-bromo-2-chloro-phenyl)-[4-fluoro-1-(2-methanesulfonyl-ethyl)-6-oxazol-5-yl-1H-benzoimidazol-5-yl]-amine.

(4-Bromo-2-chloro-phenyl)-(4-fluoro-6-oxazol-5-yl-1H-benzoimidazol-5-yl)-amine 10x. LC/MS ESI (+) m/z 409, 407 (M+ Br pattern) detected; $^1$H NMR (400 MHz, MeOH-$d_4$) δ 8.33 (s, 1H), 8.24 (s, 1H), 7.94 (bs, 1H), 7.51 (d, 1H), 7.33 (s, 1H), 7.07 (dd, 1H), 6.14 (dd, 1H).

(4-Bromo-2-chloro-phenyl)-[4-fluoro-1-(2-methanesulfonyl-ethyl)-6-oxazol-5-yl-1H-benzoimidazol-5-yl]-amine. LC/MS ESI (+) m/z 515, 513 (M+ Br pattern) detected; $^1$H NMR (400 MHz, MeOH-$d_4$) δ 8.39 (s, 1H), 8.28 (s, 1H), 8.03 (s, 1H), 7.52 (d, 1H), 7.37 (s, 1H), 7.07 (m, 1H), 6.14 (dd, 1H), 3.83 (t, 2H), 2.99 (s, 3H), 1.18 (t, 2H).

Example 51

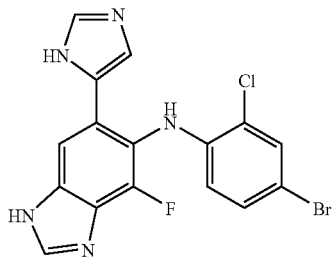

(4-Bromo-2-chloro-phenyl)-[4-fluoro-6-(3H-imidazol-4-yl)-1H-benzoimidazol-5-yl]-amine (10aa)

Step A: (4-Bromo-2-chloro-phenyl)-{4-fluoro-1-(2-methanesulfonyl-ethyl)-6-[4-(toluene-4-sulfonyl)-4,5-dihydro-oxazol-5-yl]-1H-benzoimidazol-5-yl}-amine 10bb: 6-(4-Bromo-2-chloro-phenylamino)-7-fluoro-3-(2-methanesulfonyl-ethyl)-3H-benzoimidazole-5-carbaldehyde 10z (0.050 g, 0.107 mmol) is suspended in EtOH (0.5 mL) under $N_2$ and tosylmethyl isocyanide (0.020 g, 0.105 mmol) is added followed by catalytic NaCN (~1 mg). After 2 hours, 2 mL THF is added to assist with solubility. After stirring for 16 hours at room temperature, a second equivalent of tosylmethyl isocyanide (0.020 g, 0.105 mmol) is added. After 8 hours, the reaction mixture is concentrated under reduced pressure and used as is in the next reaction: LC/MS ESI (+) m/z 671, 669 (M+ Br pattern) detected.

Step B: (4-Bromo-2-chloro-phenyl)-[4-fluoro-6-(3H-imidazol-4-yl)-1H-benzoimidazol-5-yl]-amine 10aa: (4-Bromo-2-chloro-phenyl)-{4-fluoro-1-(2-methanesulfonyl-ethyl)-6-[4-(toluene-4-sulfonyl)-4,5-dihydro-oxazol-5-yl]-1H-benzoimidazol-5-yl}-amine 10bb (0.072 g, 0.107 mmol) is treated with 2.4 mL of a 2.0 M $NH_3$ in MeOH solution in a sealed pressure tube. The reaction mixture is then heated to 90° C. with stirring for 20 hours and furthered stirred at room temperature for 3 days. The reaction mixture is transferred to a round bottom flask and concentrated under reduced pressure. Purification by flash column chromatography, twice, eluted with 10:1 methylene chloride:MeOH, followed by successive triturations with methylene chloride and then diethyl ether provides 3 mg (7%) desired product: LC/MS ESI (+) m/z 408, 406 (M+ Br pattern) detected; $^1$H NMR (400 MHz, MeOH-$d_4$) δ 8.23 (s, 1H), 7.87 (s, 1H), 7.74 (s, 1H), 7.46 (m, 1H), 7.32 (d, 1H), 7.05 (m, 1H), 6.20 (dd, 1H).

EXample 52

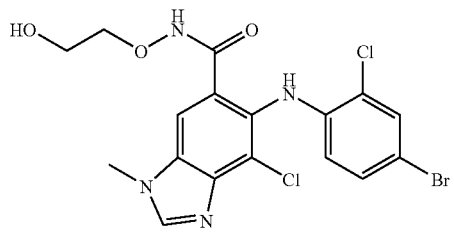

6-(4-Bromo-2-chloro-phenylamino)-7-chloro-3-methyl-3H-benzoimidazole-5-carboxylic acid (2-hydroxy-ethoxy)-amide (10cc)

Step A: 3-Chloro-2,4-difluoro-5-nitro-benzoic acid 2a: 3-Chloro-2,4-difluoro-benzoic acid 1a (3.00 g, 15.6 mmol) is added to a stirred solution of concentrated $H_2SO_4$ (16 mL) and fuming nitric acid (0.85 mL, 20.3 mmol). After 3 hours a precipitate forms. The yellow slurry is poured onto ice water (100 mL). The aqueous mixture is extracted with diethyl ether (3×). The organic extracts are dried ($Na_2SO_4$) and concentrated under reduced pressure to give 3.50 g (95%) of clean desired product as a pale yellow solid.

Step B: 4-Amino-3-chloro-2-fluoro-5-nitro-benzoic acid 3a: Ammonium hydroxide solution (6.88 g, ~30% in water, 58.9 mmol) is added to a solution of 3-chloro-2,4-difluoro-5-nitro-benzoic acid 2a (3.5 g, 14.7 mmol) in water (16 mL) at 0° C. with stirring. Upon completion of the ammonium hydroxide addition the reaction mixture is warmed to room temperature. After 5 hours the reaction mixture is cooled to 0° C. and concentrated HCl is carefully added until the pH of the reaction mixture is near zero. The solid is collected by filtration and washed with water and diethyl ether. The solids are transferred to a round bottom flask as a solution in MeOH and EtOAc and concentrated under reduced pressure to give 2.96 g of a yellow solid. The filtrate is partitioned between diethyl ether and water and the organic layer is washed with brine. The combined organic extracts are dried ($Na_2SO_4$) and concentrated under reduced pressure to give 0.65 g of product. Recovered a total of 3.61 g (104%) of pure desired product that is carried forward without further purification.

Step C: 4-Amino-3-chloro-2-fluoro-5-nitro-benzoic acid methyl ester 4a: To a stirred solution of 4-amino-3-chloro-2-fluoro-5-nitro-benzoic acid 3a (3.61 g, 15.4 mmol) in THF (30 mL) and MeOH (10 mL), TMS diazomethane (9.23 mL, 2.0 M solution in hexanes, 18.5 mmol) is added. After completion of reaction, the reaction mixture is concentrated via rotary evaporation with acetic acid in the trap. The recovered oily solid is triturated with diethyl ether to provide 1.51 g of a yellow solid. The filtrate is concentrated and triturated with diethyl ether to give an additional 0.69 g of yellow solid. A total of 2.20 g (57%) of pure desired product is recovered.

Step D: 4-Amino-3-chloro-5-nitro-2-phenylamino-benzoic acid methyl ester 5c: 4-Amino-3-chloro-2-fluoro-5-nitro-benzoic acid methyl ester 4a (2.20 g, 8.84 mmol) is suspended in MeOH (9.4 mL) and aniline (3.22 mL, 35.4 mmol) is added. The reaction mixture is heated to reflux with stirring under a nitrogen atmosphere. After 19 hours, the reaction is complete. Distilled water (3.22 mL) is added to the reaction mixture and refluxing is continued for one hour. The reaction mixture is cooled to 0° C. in an ice bath for 20 minutes. The reaction mixture is filtered and washed with 3:10 distilled water/MeOH (65 mL total) and then with MeOH. The solid is dissolved with $CH_2Cl_2$ and concentrated under reduced pressure to give 2.40 g (84%) of pure desired product. MS APCI (−) m/z 320.3 (M−1) detected.

Step E: 4,5-Diamino-3-chloro-2-phenylamino-benzoic acid methyl ester 6b: 4-Amino-3-chloro-5-nitro-2-phenylamino-benzoic acid methyl ester 5c (0.50 g, 1.55 mmol) is dissolved into 2:1 EtOH/MeOH (15.5 mL). Saturated aqueous $NH_4Cl$ (15 mL), Zn powder (1.02 g, 15.6 mmol), and THF (10 mL) are added. After stirring for 20 hours, the reaction mixture is diluted with $CH_2Cl_2$/THF and water. The organic layer is washed with water (3×). The combined organic extracts are dried ($Na_2SO_4$) and concentrated under reduced pressure. The solids are triturated with ether to give 0.32 g (70%) clean desired product.

Step F: 7-Chloro-6-phenylamino-3H-benzoimidazole-5-carboxylic acid methyl ester 7c: 4,5-Diamino-3-chloro-2-phenylamino-benzoic acid methyl ester 6b (0.32 g, 1.09 mmol) and formamidine acetate (72 mg, 1.64 mmol) in EtOH (36 mL) are heated, with stirring, to 80° C. After 44 hours, the reaction mixture is cooled to room temperature and diluted with EtOAc and washed with water (3×), saturated $NaHCO_3$, and brine. The combined organic extracts are dried ($Na_2SO_4$) and concentrated under reduced pressure to give 0.33 g (99%) clean desired product as a solid. MS APCI (+) m/z 302.3 (M+1) detected.

Step G: 6-(4-Bromo-phenylamino)-7-chloro-3H-benzoimidazole-5-carboxylic acid methyl ester 8g: 7-Chloro-6-phenylamino-3H-benzoimidazole-5-carboxylic acid methyl ester 7c (0.327 g, 1.08 mmol) is dissolved into DMF (16 mL) and NBS (0.193 g, 1.08 mmol) is added. After one hour, the reaction mixture is quenched by the addition of saturated aqueous $NaHSO_3$. The reaction mixture is then partitioned between EtOAc/THF and water. The organic layer is washed with water and brine. The combined organic extracts are dried ($Na_2SO_4$) and concentrated under reduced pressure. The recovered solid is triturated with ether to give 0.225 g (54%) pure desired product. MS ESI (+) m/z 382, 384 (M+, Br pattern) detected.

Step H: 6-(4-Bromo-2-chloro-phenylamino)-7-chloro-3H-benzoimidazole-5-carboxylic acid methyl ester 10dd: 6-(4-Bromo-phenylamino)-7-chloro-3H-benzoimidazole-5-carboxylic acid methyl ester 8g (0.225 g, 0.591 mmol) is dissolved in DMF (2 mL) and NCS (79 mg, 0.591 mmol) is added. After the NCS is in solution concentrated HCl (0.005 mL, 0.059 mmol) is added. After 2 hours, sodium bicarbonate, water and $NaHSO_3$ are added to the reaction mixture. Solids are filtered and washed with water and ether to give 0.141 g (57%) of clean desired product as a tan solid. MS APCI (−) m/z 414, 416 (M−, Br pattern) detected.

Step I: 6-(4-Bromo-2-chloro-phenylamino)-7-chloro-3-methyl-3H-benzoimidazole-5-carboxylic acid methyl ester 10ee: 6-(4-Bromo-2-chloro-phenylamino)-7-chloro-3H-benzoimidazole-5-carboxylic acid methyl ester 10dd (0.141 g, 0.34 mmol), potassium carbonate (0.141 g, 1.02 mmol), and iodomethane (0.063 mL, 1.02 mmol) are dissolved in dimethylformamide (3 mL). After 20 hours, the reaction mixture is diluted with EtOAc and washed with water (3×), potassium carbonate, and brine. The organic layer is dried ($Na_2SO_4$) and concentrated to a brown oil. The N3 and N1 alkylated regioisomers are separated by flash chromatography (EtOAc). The recovery of the N3 alkylated regioisomer is 20.4 mg (28%). MS ESI (+) m/z 428, 430 (M+, Br pattern) detected.

Step J: 6-(4-Bromo-2-chloro-phenylamino)-7-chloro-3-methyl-3H-benzoimidazole-5-carboxylic acid 10ff: 6-(4-Bromo-2-chloro-phenylamino)-7-chloro-3-methyl-3H-benzoimidazole-5-carboxylic acid methyl ester 10ee (21 mg, 0.048 mmol) is dissolved into 2:1 THF/water (1.2 mL) and NaOH (0.190 mL, 1.0 M aqueous solution, 0.190 mmol) is added. After stirring for 4 hours the reaction is diluted with water and acidified to pH 2 by addition of 1.0 M HCl. The mixture is then extracted with 3:1 EtOAc/THF (3×), dried ($Na_2SO_4$) and concentrated to give quantitative yield of desired product as a white solid. MS APCI (+) m/z 414, 416 (M+, Br pattern) detected.

Step K: 6-(4-Bromo-2-chloro-phenylamino)-7-chloro-3-methyl-3H-benzoimidazole-5-carboxylic acid (2-vinyloxy-ethoxy)-amide 10gg: 6-(4-Bromo-2-chloro-phenylamino)-7-chloro-3-methyl-3H-benzoimidazole-5-carboxylic acid 10ff (32 mg, 0.077 mmol), O-(2-vinyloxy-ethyl)-hydroxylamine (0.010 mL, 0.092 mmol), HOBt (13 mg, 0.093 mmol), triethylamine (0.011 mL, 0.077 mmol), and EDCI (19 mg, 0.10 mmol) are dissolved into dimethylformamide (1.0 mL) and allowed to stir under a nitrogen atmosphere at room temperature for 24 hours. The reaction mixture is diluted with EtOAc, washed with water (3×), 10% potassium carbonate (2×), saturated ammonium chloride, brine, dried (Na$_2$SO$_4$), and concentrated under reduced pressure to give 39 mg of 85% pure material. MS APCI (−) m/z 497, 501 (M−, Br pattern) detected.

Step L: 6-(4-Bromo-2-chloro-phenylamino)-7-chloro-3-methyl-3H-benzoimidazole-5-carboxylic acid (2-hydroxy-ethoxy)-amide 10cc: Hydrochloric acid (0.78 mL, 1.0 M aqueous solution, 0.78 mmol) is added to a suspension of 6-(4-bromo-2-chloro-phenylamino)-7-chloro-3-methyl-3H-benzoimidazole-5-carboxylic acid 10gg (2-vinyloxy-ethoxy)-amide (39 mg, 0.078 mmol) in MeOH (1 mL). After one hour, the reaction mixture is neutralized to pH 7 and concentrated under reduced pressure. The solids are dissolved in EtOAc, washed with brine, dried (Na$_2$SO$_4$), and concentrated under reduced pressure. Flash chromatography (20:1 CH$_2$Cl$_2$/MeOH) provided 9 mg (23%) of pure product: MS APCI (+) m/z 473, 475 (M+, Br pattern) detected; $^1$H NMR (400 MHz, CDCl$_3$) δ 8.30 (s, 1H), 8.08 (s, 1H), 7.57 (d, 1H), 7.15 (dd, 1H), 6.21 (d, 1H), 3.97 (s, 3H), 3.86 (m, 2H), 3.57 (m, 2H).

Example 53

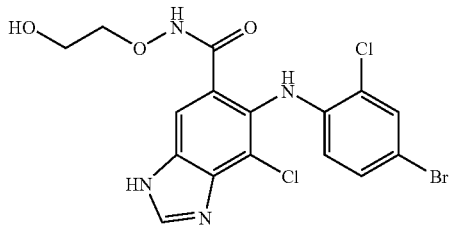

6-(4-Bromo-2-chloro-phenylamino)-3H-benzoimidazole-5-carboxylic acid (2-hydroxy-ethoxy)-amide (10hh)

The above compound is prepared in an analogous fashion to Example 52 except that Step 1 is eliminated. MS APCI (−) m/z 457, 461 (M−, Br pattern) detected; $^1$H NMR (400 MHz, CD$_3$OD) δ 8.40 (s, 1H), 7.85 (s, 1H), 7.50 (d, 1H), 7.14 (dd, 1H), 6.21 (d, 1H), 3.84 (m, 2H), 3.61 (m, 2H).

Example 54

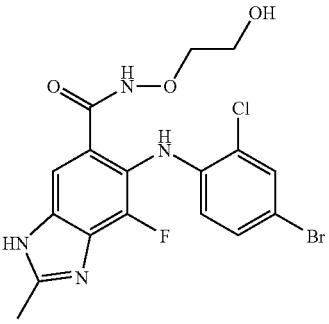

6-(4-Bromo-2-chloro-phenylamino)-7-fluoro-2-methyl-3H-benzoimidazole-5-carboxylic acid (2-hydroxy-ethoxy)-amide (10ii)

Step A: 4,5-Diamino-3-fluoro-2-phenylamino-benzoic acid methyl ester 6c: 4-Amino-3-fluoro-5-nitro-2-phenylamino-benzoic acid methyl ester 26a (11.44 g, 37.48 mmol) is suspended in ethanol (400 mL) and ammonium formate (11.80 g, 187.0 mmol) and 20% Pd(OH)$_2$/C (10.00 g, 18.79 mmol) are added. The reaction mixture is stirred at 95° C. under N$_2$ for 30 minutes. The reaction mixture is cooled to room temperature and then filtered through celite, rinsing with ethanol. The filtrate is concentrated under reduced pressure to give 9.63 g (93%) of the pure desired product as a purple/red solid. MS ESI (+) m/z 276 (M+1) detected.

Step B: 7-Fluoro-2-methyl-6-phenylamino-3H-benzoimidazole-5-carboxylic acid methyl ester 31a: 4,5-Diamino-3-fluoro-2-phenylamino-benzoic acid methyl ester 6c (0.20 g, 0.73 mmol) is suspended in ethanol (3 mL) and 5 M aqueous HCl (1 mL., 5.00 mmol) is added. The reaction mixture is brought to reflux under N$_2$ and then 2,4-pentanedione (0.150 mL, 1.45 mmol) is added. The reaction mixture is stirred at reflux for 60 minutes. The reaction mixture is cooled to room temperature and treated with saturated aqueous NaHCO$_3$ until the pH of the reaction mixture is pH 7 and is then concentrated under reduced pressure to dryness. The residue is diluted with ethyl acetate and water, poured into a separatory funnel and the layers separated. The ethyl acetate layer is washed with brine, dried (Na$_2$SO$_4$) and concentrated under reduced pressure. The red solid residue is triturated with diethyl ether to yield a light brown solid and a red filtrate. The solid is collected and washed with diethyl ether to yield 0.20 g (91%) of the pure desired product as a light brown solid. MS ESI (+) m/z 300 (M+1) detected.

Step C: 644-Bromo-2-chloro-phenylamino)-7-fluoro-2-methyl-3H-benzoimidazole-5-carboxylic acid (2-hydroxy-ethoxy)-amide 10ii: 7-Fluoro-2-methyl-6-phenylamino-3H-benzoimidazole-5-carboxylic acid methyl ester 31a is converted by the bromination, chlorination, hydrolysis, coupling, and hydrolysis procedures already described to yield the pure desired product as an off-white solid. MS ESI (+) m/z 457, 459 (M+, Br pattern) detected; $^1$H NMR (400 MHz, CD$_3$OD) δ 7.58 (s, 1H), 7.49 (d, 1H), 7.18 (dd, 1H), 6.41 (m, 1H), 3.91 (t, 2H), 3.65 (t, 2H), 2.61 (s, 3H); $^{19}$F NMR (376 MHz, CD$_3$OD) −135.84 (s).

Example 55

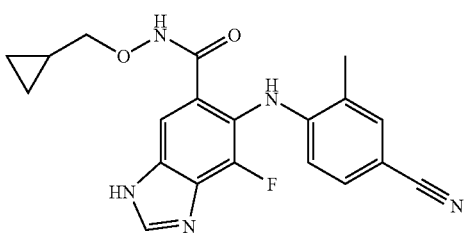

6-(4-Cyano-2-methyl-phenylamino)-7-fluoro-3H-benzoimidazole-5-carboxylic acid cyclopropylmethyoxy-amide (11yy)

Step A: 7-Fluoro-6-(4-iodo-2-methyl-phenylamino)-1H-benzoimidazole-5-carboxylic acid methyl ester 10jj:

7-Fluoro-6-o-tolylamino-1H-benzoimidazole-5-carboxylic acid methyl ester 7a (1.47 g, 4.92 mmol) is suspended in 1:1 THF:MeOH mixture (44 mL) and cooled to −78° C. under a nitrogen atmosphere. A solution of NIS (1.66 g, 7.39 mmol) in THF (2 mL) is added followed by a MeOH (2 mL) solution of TsOH.H₂O (1.87 g, 9.84 mmol). After 30 minutes, the reaction mixture is warmed to 0° C. and 1 mL methylene chloride is added. The reaction is slowly allowed to warm to room temperature with stirring over 16 hours. The reaction mixture is quenched by the addition of 10% Na₂S₂O₄ solution. The reaction mixture is then diluted with water and ethyl acetate and the layers separated. The aqueous layer is extracted with ethyl acetate. The combined organic extracts are dried (Na₂SO₄) and concentrated under reduced pressure. The recovered solid is triturated with MeOH to give 1.45 g (69%) pure desired product: MS ESI (+) m/z 426 (M+1) detected; MS ESI (−) m/z 424 (M−1) detected.

Step B: 7-Fluoro-6-(4-iodo-2-methyl-phenylamino)-(2-trimethylsilanyl-ethoxymethyl)-benzoimidazole-5-carboxylic acid methyl ester 10kk: 7-Fluoro-6-(4-iodo-2-methyl-phenylamino)-1H-benzoimidazole-5-carboxylic acid methyl ester 10jj (0.200 g, 0.470 mmol) is suspended in DMF (2 mL) under N₂ and cooled to 0° C. in an ice-water bath. NaH (60% dispersion in oil, 0.018 g, 0.470 mmol) is added. After 10 minutes, the reaction mixture is warmed to room temperature and stirred for 30 minutes. After cooling to 0° C., SEMCl (0.087 mL, 0.494 mmol) is added and the reaction is allowed to warm to room temperature with stirring overnight. The reaction mixture is quenched by the addition of water and brine. The reaction mixture is extracted with ethyl acetate. The combined organic extracts are washed with water and brine, and dried (MgSO₄) and concentrated under reduced pressure. Purification by flash column chromatography eluted with 1:1 hexanes:ethyl acetate provides 0.182 g (70%) of desired product as a 1:1 mixture of N1 and N3 isomers as a white foam.

Step C: 6-(4-Cyano-2-methyl-phenylamino)-7-fluoro-(2-trimethylsilanyl-ethoxymethyl)-benzoimidazole-5-carboxylic acid methyl ester 10ll: To a stirred solution of a 1:1 mixture of N1:N3 isomers of 7-fluoro-6-(4-iodo-2-methyl-phenylamino)-(2-trimethylsilanyl-ethoxymethyl)-benzoimidazole-5-carboxylic acid methyl ester 10jj (0.060 g, 0.108 mmol) in 1 mL DMF at room temperature under N₂ is added dppf (2 mg, 0.004 mmol) followed by Pd₂ dba₃ (2 mg, 0.002 mmol) and Zn(CN)₂ (8 mg, 0.065 mmol) (Tetrahedron Lett. 1999, 40, 8193-8195). The reaction mixture is heated to 120° C. for 45 minutes. The reaction mixture is cooled to room temperature and quenched by the addition of 5 mL of a 4:1:5 mixture of sat NH₄Cl:conc NH₄OH:water. The aqueous layer is extracted with ethyl acetate. The combined organic extracts are washed with water (3×), brine, and dried (MgSO₄) and concentrated under reduced pressure. Purification by flash column chromatography eluted with 1:1 hexanes:ethyl acetate provides 38 mg (77%) of desired product as a 1:1 mixture of N1 and N3 isomers: APCI MS (+) m/z 455 (M+1) detected.

Step D: 6-(4-Cyano-2-methyl-phenylamino)-7-fluoro-(2-trimethylsilanyl-ethoxymethyl)-benzoimidazole-5-carboxylic acid 10mm: A 1:1 mixture of N1:N3 isomers of 6-(4-cyano-2-methyl-phenylamino)-7-fluoro-(2-trimethylsilanyl-ethoxymethyl)-benzoimidazole-5-carboxylic acid methyl ester 10ll (31 mg, 0.068 mmol) is hydrolyzed with aqueous sodium hydroxide as described previously to give 26 mg (87%) of desired product.

Step E: 6-(4-Cyano-2-methyl-phenylamino)-7-fluoro-(2-trimethylsilanyl-ethoxymethyl)-benzoimidazole-5-carboxylic acid cyclopropylmethyoxy-amide 11zz: A 1:1 mixture of N1:N3 isomers of 6-(4-cyano-2-methyl-phenylamino)-7-fluoro-(2-trimethylsilanyl-ethoxymethyl)-benzoimidazole-5-carboxylic acid 10mm (26 mg, 0.059 mmol) is coupled with EDCI and cyclopropyl methyl hydroxylamine hydrochloride as described previously to give 28 mg (93%) of desired product: APCI MS (+) m/z 510 (M+1) detected.

Step F: 6-(4-Cyano-2-methyl-phenylamino)-7-fluoro-3H-benzoimidazole-5-carboxylic acid cyclopropylmethyoxy-amide 11yy: To a slurry of a 1:1 mixture of N1:N3 isomers 6-(4-cyano-2-methyl-phenylamino)-7-fluoro-(2-trimethylsilanyl-ethoxymethyl)-benzoimidazole-5-carboxylic acid cyclopropylmethyoxy-amide 11zz (28 mg, 0.055 mmol) in 0.5 mL EtOH is added 0.5 mL 10% HCl. The reaction mixture is heated to 50° C. with stirring overnight (Whitten et al., *J. Org. Chem.*, 1986, 51, 1891-1894). An additional 0.5 mL 10% HCl is added and the reaction mixture stirred at 70° C. overnight. The reaction mixture is cooled to room temperature and neutralized to pH ~8 with 1.5 mL 1N NaOH. The reaction mixture is extracted with ethyl acetate, dried (MgSO₄) and concentrated under reduced pressure to give 14 mg (60%) of 90% pure product as a mixture of rotatomers: MS APCI (+) m/z 380 (M+1) detected; MS APCI (−) m/z 378 (M−1) detected; ¹H NMR (400 MHz, MeOH-d₄) δ 8.41 (bs, 1H), 7.75 (m, 1H), 7.50 (s, 1H), 7.38 (d, 1H), 6.51 (m, 1H), 3.72 (d, 0.5H), 3.65 (d, 1.5H), 2.41 (s, 3H), 0.98 (1H, m), 0.58 (d, 1.5H), 0.40 (d, 0.5H), 0.25 (d, 1.5H), 0.19 (d, 0.5H).

Example 56

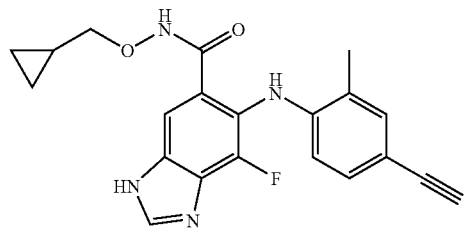

6-(4-Ethynyl-2-methyl-phenylamino)-7-fluoro-3H-benzoimidazole-5-carboxylic acid cyclopropyl-methoxy-amide 11aaa Step A: 7-Fluoro-6-(2-methyl-4-trimethylsilanylethynyl-phenylamino)-3H-benzoimidazole-5-carboxylic acid cyclopropylmethoxy-amide 11bbb: 7-Fluoro-6-(4-iodo-2-methyl-phenylamino)-3H-benzoimidazole-5-carboxylic acid cyclopropylmethoxy-amide 11ccc (0.025 g, 0.052 mmol) is dissolved in 1:1 acetonitrile/triethylamine (0.50 mL). Ethynyl-trimethylsilane (0.013 mL, 0.092 mmol), Pd(PPh₃)₂Cl₂ (0.004 g, 0.006 mmol), and CuI (0.002 g, 0.011 mmol) are added consecutively and the reaction mixture is stirred at 60° C. for 1 hour under N₂. The reaction mixture is cooled to room temperature and concentrated under reduced pressure. The residue is purified by FCC (eluting with 20:1 methylene chloride:methanol) to yield 0.020 g (87%) of the desired product.

Step B: 6-(4-Ethynyl-2-methyl-phenylamino)-7-fluoro-3H-benzoimidazole-5-carboxylic acid cyclopropylmethoxy-amide 11aaa: 7-Fluoro-6-(2-methyl-4-trimethylsilanylethynyl-phenylamino)-3H-benzoimidazole-5-carboxylic acid cyclopropylmethoxy-amide 11bbb (0.020 g, 0.044 mmol) is dissolved in tetrahydrofuran (0.50 mL) and the reaction solution is cooled to 0° C. TBAF (50 uL, 0.050 mmol, 1 M solution in tetrahydrofuran) is added. The reaction mixture is warmed to room temperature and additional TBAF (25 uL, 0.025 mmol, 1 M solution in tetrahydrofuran) is added. The reaction mixture is stirred at 50° C. for 2 hours under $N_2$. The reaction mixture is cooled to room temperature, a few drops of $H_2O$ are added and then it is concentrated under reduced pressure. The residue is purified by FCC (eluting with 20:1 methylene chloride:methanol) to yield 0.011 g (65%) of the pure desired product. MS APCI (−) m/z 377 (M−1) detected; $^1$H NMR (400 MHz, $CDCl_3$) δ 10.56 (broad s, 1H), 8.12 (s, 1H), 7.99 (s, 1H), 7.28 (s, 1H), 7.11 (d, 1H), 6.42 (broad, 1H), 3.70 (br s, 2H), 2.96 (d, 1H), 2.37 (s, 3H), 0.85 (m, 1H), 0.50 (m, 2H), 0.22 (m, 2H).

The invention and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

What is claimed is:

1. A pharmaceutical composition which comprises an amount of a compound which is 6-(4-bromo-2-fluorophenylamino)-7-fluoro-3-methyl-3H-benzoimidazole-5-carboxylic acid (2-hydroxyethoxy)-amide, or a pharmaceutically acceptable salt thereof, in combination with an amount of a chemotherapeutic.

2. A pharmaceutical composition according to claim 1, wherein the chemotherapeutic is selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, angiogenesis inhibitors and anti-androgens.

3. A pharmaceutical composition comprising an amount of 6-(4-bromo-2-fluorophenylamino)-7-fluoro-3-methyl-3H-benzoimidazole-5-carboxylic acid (2-hydroxyethoxy)-amide, or a pharmaceutically acceptable salt thereof, in combination with an amount of an anti-tumour agent selected from the group consisting of mitotic inhibitors, alkylating agents, anti-metabolites, intercalating antibiotics, growth factor inhibitors, cell cycle inhibitors, enzyme inhibitors, topoisomerase inhibitors, biological response modifiers, anti-hormones, angiogenesis inhibitors and anti-androgens.

4. A pharmaceutical composition according to claim 2, wherein the chemotherapeutic is selected from the group comprising vinblastine, cis-platin, carboplatin, cyclophosphamide, 5-fluorouracil, cytosine arabinside, hydroxyurea, N-(5-[N-3,4-dihydro-2-methyl-4-oxoquinazolin-6-ylmethyl)-N-methylamino]-2-thenoyl)-L-glutamic acid, adriamycin, bleomycin, interferon, Nolvadex™ (tamoxifen) and Casodex™ (4'-cyano-3-(4-fluorophenylsulphonyl)-2-hydroxy-2-methyl-3'-(trifluoromethyl)propionanilide.

* * * * *